United States Patent
Hah et al.

(10) Patent No.: US 10,781,201 B2
(45) Date of Patent: Sep. 22, 2020

(54) BENZIMIDAZOLE DERIVATIVE HAVING JNK INHIBITORY ACTIVITY AND USE THEREOF

(71) Applicant: INDUSTRY-UNIVERSITY COOPERATION FOUNDATION HANYANG UNIVERSITY ERICA CAMPUS, Ansan-si, Gyeonggi-do (KR)

(72) Inventors: Jung Mi Hah, Seoul (KR); Song I Yang, Geoje-si (KR)

(73) Assignee: INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 0 days.

(21) Appl. No.: 16/544,029

(22) Filed: Aug. 19, 2019

(65) Prior Publication Data

US 2020/0039959 A1    Feb. 6, 2020

Related U.S. Application Data

(63) Continuation of application No. PCT/KR2018/001999, filed on Feb. 19, 2018.

(30) Foreign Application Priority Data

Feb. 20, 2017 (KR) .................. 10-2017-0022188

(51) Int. Cl.
*C07D 403/04* (2006.01)
*C07D 403/14* (2006.01)
*C07D 405/14* (2006.01)
*C07D 401/14* (2006.01)

(52) U.S. Cl.
CPC ......... *C07D 401/14* (2013.01); *C07D 403/04* (2013.01); *C07D 403/14* (2013.01); *C07D 405/14* (2013.01)

(58) Field of Classification Search
CPC ... C07D 403/04; C07D 403/14; C07D 405/14
See application file for complete search history.

(56) References Cited

FOREIGN PATENT DOCUMENTS

| KR | 10-2001-0029352 A | 4/2001 |
|---|---|---|
| KR | 10-2008-0015475 A | 2/2008 |
| KR | 10-2014-0111521 A | 9/2014 |
| WO | 03/000682 A1 | 1/2003 |

OTHER PUBLICATIONS

International Search Report issued in PCT/KR2018/001999; dated Oct. 29, 2018.
Mi Hyun Kim et al.; "3D-QSAR studies of 1,2-diaryl-1H-benzimidazole derivatives as JNK3 inhibitors with protective effects in neuronal cells"; Bioorganic & Medicinal Chemistry Letters; 2013; pp. 1639-1642; vol. 23, No. 6.
Mi Hyun Kim et al.; "Syntheses and biological evaluation of 1-heteroaryl-2-aryl-1H-benzimidazole derivatives as c-Jun N-terminal kinase inhibitors with neuroprotective effects"; Bioorganic & Medicinal Chemistry Letters; 2013; pp. 2271-2285; vol. 21, No. 8.

*Primary Examiner* — Laura L Stockton
(74) *Attorney, Agent, or Firm* — Studebaker & Brackett PC

(57) ABSTRACT

The present invention relates to a novel benzimidazole derivative having JNK (C-Jun N-terminal kinase) inhibitory activity and use thereof. The novel benzimidazole derivative or a pharmaceutically acceptable salt thereof according to the present invention exhibits excellent inhibitory activity against c-Jun N-terminal kinase 3(JNK 3), and thus it is expected that target therapy can be attained through a more fundamental approach in the prevention or treatment of degenerative brain-nerve system disease.

5 Claims, 1 Drawing Sheet

BENZIMIDAZOLE DERIVATIVE HAVING JNK INHIBITORY ACTIVITY AND USE THEREOF

CROSS-REFERENCE TO RELATED APPLICATIONS

This application is a continuation of International Application No. PCT/KR2018/001999 filed Feb. 19, 2018, which claims benefit of priority to Korean Patent Application No. 10-2017-0022188 filed Feb. 20, 2017. The entire contents of the above applications are incorporated herein by reference.

TECHNICAL FIELD

The present invention relates to a novel benzimidazole derivative having C-Jun N-terminal kinase (JNK) inhibitory activity and a use thereof.

BACKGROUND ART

Recently, the number of patients suffering from neurodegenerative brain diseases is rapidly increasing with an increase in the elderly population. Neurodegenerative brain diseases may be caused by adult disease-derived secondary symptoms such as aging-induced structural degeneration of neurons, circulatory disorders, and the like, or physical and mechanical factors such as traffic accidents, industrial accidents, carbon monoxide poisoning, and the like, and as related diseases, Alzheimer' disease, Parkinson' disease, Huntington's disease, multiple sclerosis, stroke, and the like are known.

Meanwhile, c-Jun N-terminal kinase (JNK), which is classified as a serine/threonine kinase, is one of the three subfamilies of mitogen-activated protein kinases and is also referred to as stress activated protein kinase (SAPK). It is known that JNK is activated in response to a variety of stimuli such as cytokines, mitogens, osmotic stress, ultraviolet irradiation, and the like, and the activated JNK promotes the phosphorylation of a variety of transcription factors including c-Jun of AP-1 and intracellular proteins related to apoptosis, such as Bcl2, p53, and the like. In addition, JNK genes form different types of isoforms by splicing. Among them, the distribution of JNK3 is concentrated in brain tissue unlike the same kind of isoforms, the number of which is about 10, and thus various studies have been conducted on the relationship between JNK3 and neurodegenerative brain disease.

In particular, it has been reported that JNK3 phosphorylates and activates amyloid precursor protein (APP), which is the main cause of Alzheimer's disease, to thus allow the APP to be located in a cell membrane, promotes the conversion of APP to beta-amyloid, and in a case in which, after beta-amyloid is formed, the apoptosis of neurons is induced by toxicity thereof, the activation of JNK3 acts as a main cause. In addition, a dramatic decrease in oligomeric beta-amyloid and an increase in cognitive ability, caused by the removal of JNK3, are observed in mice with familial Alzheimer's disease (FAD), and resistance to MPTP, which is a Parkinson's disease-inducing material, is acquired in mice from which the JNK3 gene is removed, and an effect of inhibiting side effects of glutamate analogs, which are neurotoxic substances, has been found in the mice.

Under these circumstances, research on the discovery of a JNK3 inhibitor as a novel substance for the treatment of neurodegenerative brain diseases has been actively conducted (Korean Patent Publication No. 2001-0029352), and it is still not adequate.

Technical Problem

The present invention has been made to address the above-described problems, and as a result of having conducted intensive research to discover a novel material having the possibility of being developed as a therapeutic agent for neurodegenerative brain diseases, the inventors of the present invention identified a novel benzimidazole derivative having JNK inhibitory activity, and thus completed the present invention based on these findings.

Therefore, an object of the present invention is to provide a novel benzimidazole derivative having JNK inhibitory activity or a pharmaceutically acceptable salt thereof.

Another object of the present invention is to provide a novel benzimidazole derivative having JNK inhibitory activity.

Another object of the present invention is to provide a pharmaceutical composition for preventing or treating a neurodegenerative brain disease, which includes, as an active ingredient, the benzimidazole derivative or a pharmaceutically acceptable salt thereof.

However, technical problems to be solved by the present invention are not limited to the above-described technical problems, and other unmentioned technical problems will become apparent from the following description to those of ordinary skill in the art.

Technical Solution

To achieve the above objectives of the present invention, there is provided a benzimidazole derivative represented by Formula 1 below or a pharmaceutically acceptable salt thereof.

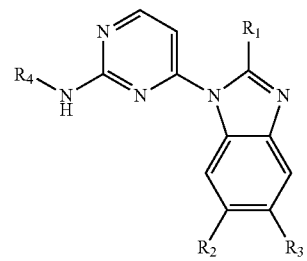

[Formula 1]

wherein, in Formula 1, $R_1$ is selected from the group consisting of benzooxazolyl, benzodioxazolyl, 1,3-benzodioxolyl, 1,4-benzodioxinyl, dihydrobenzodioxinyl, benzothiazolyl, benzothiophenyl, quinolinyl, isoquinolinyl, indolyl, benzofuranyl, purinyl, and indolizinyl;

$R_2$ and $R_3$ are each independently hydrogen or hydroxy;

$R_4$ represents a $C_3$-$C_{10}$ cycloalkyl or a $C_4$-$C_{10}$ heterocycloalkyl wherein the $C_4$-$C_{10}$ heterocycloalkyl is selected from the group consisting of tetrahydrofuranyl, tetrahydrothiophenyl, pyrrolidinyl, tetrahydropyranyl, tetrahydrothiopyranyl, and piperidinyl; and $R_4$ may be substituted or unsubstituted with a $C_4$-$C_{10}$ cycloalkylcarbonyl.

The present invention also provides a pharmaceutical composition for preventing or treating a neurodegenerative brain disease, which includes, as an active ingredient, the derivative of Formula 1 or a pharmaceutically acceptable salt thereof.

In one embodiment of the present invention, the neurodegenerative brain disease may be selected from the group consisting of Alzheimer' disease, Parkinson' disease, Huntington's disease, multiple sclerosis, and stroke.

In another embodiment of the present invention, the composition may inhibit the activity of C-Jun N-terminal kinase 3 (JNK 3).

The present invention also provides a method of treating a neurodegenerative brain disease, including administering, to an individual, the derivative of Formula 1 or a pharmaceutically acceptable salt thereof.

The present invention also provides a use of the derivative of Formula 1 or a pharmaceutically acceptable salt thereof for the treatment of a neurodegenerative brain disease.

Advantageous Effects of Invention

A novel benzimidazole derivative or a pharmaceutically acceptable salt thereof according to the present invention exhibits excellent inhibitory activity against c-Jun N-terminal kinase 3 (JNK 3), and thus a pharmaceutical composition including the derivative is expected to be effectively used for the prevention and treatment of neurodegenerative brain diseases.

DETAILED DESCRIPTION

Figure 1:
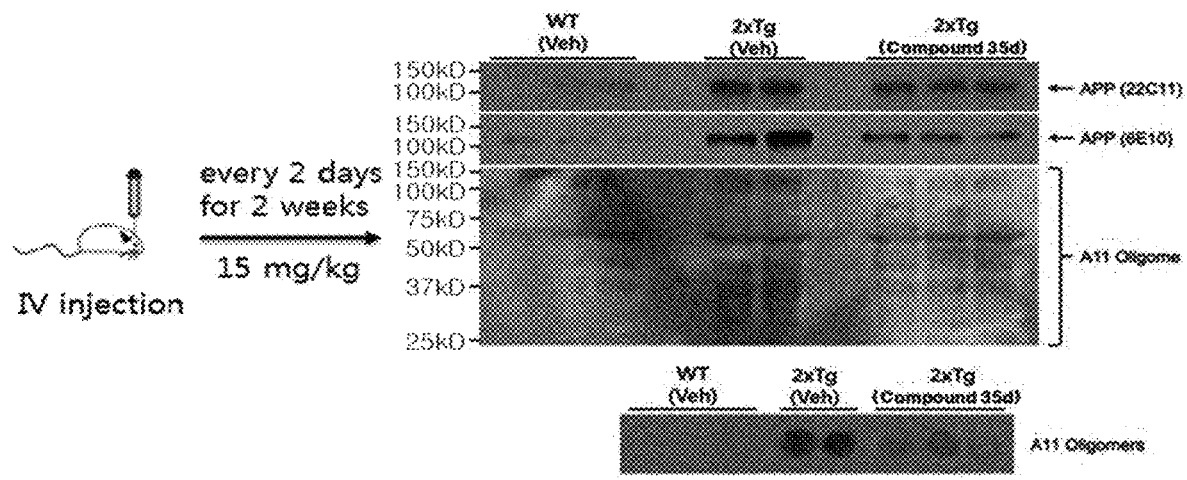
FIG. 1 illustrates western blotting results of confirming changes in the concentration of APP and beta-amyloid oligomer in the frontal lobe cortex according to treatment with a derivative of the present invention.

Hereinafter, the present invention will be described in detail.

To achieve the above objectives of the present invention, there is provided a benzimidazole derivative represented by Formula 1 below or a pharmaceutically acceptable salt thereof.

[Formula 1]

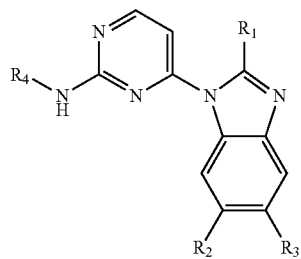

wherein, in Formula 1, $R_1$ is selected from the group consisting of benzooxazolyl, benzodioxazolyl, 1,3-benzodioxolyl, 1,4-benzodioxinyl, dihydrobenzodioxinyl, benzothiazolyl, benzothiophenyl, quinolinyl, isoquinolinyl, indolyl, benzofuranyl, purinyl, and indolizinyl; $R_2$ and $R_3$ are each independently hydrogen or hydroxy; $R_4$ represents a $C_3$-$C_{10}$ cycloalkyl or a $C_4$-$C_{10}$ heterocycloalkyl wherein the $C_4$-$C_{10}$ heterocycloalkyl is selected from the group consisting of tetrahydrofuranyl, tetrahydrothiophenyl, pyrrolidinyl, tetrahydropyranyl, tetrahydrothiopyranyl, and piperidinyl; and $R_4$ may be substituted or unsubstituted with a $C_4$-$C_{10}$ cycloalkylcarbonyl.

As used herein, the "substituted" group indicates that one or more hydrogen atoms of the corresponding group is substituted with one or more non-hydrogen atoms, wherein valence requirements must be satisfied and a chemically stable compound must be generated from substitution. Unless the term "unsubstituted" is stated explicitly in the present specification, all substituents should be construed as being able to be substituted or unsubstituted. The substituent of $R_4$ of the benzimidazole derivative according to the present invention may be substituted again with one or more selected from the substituents defined above.

The term "cycloalkyl" refers to a saturated monocyclic or polycyclic hydrocarbon ring which generally contains a ring and has the indicated number of carbon atoms (i.e., a $C_{3-10}$ cycloalkyl refers to a cyclic ring having 3, 4, 5, 6, 7, 8, 9, or 10 carbon atoms as ring members). The term "heterocycloalkyl" refers to a monocyclic or polycyclic heterocycle group containing 1 to 4 heteroatoms each independently selected from nitrogen, oxygen, and sulfur, and non-limiting examples of the heterocycloalkyl include tetrahydrofuranyl, tetrahydrothiophenyl, pyrrolidinyl, tetrahydropyranyl, tetrahydrothiopyranyl, piperidinyl, and dihydrobenzodioxinyl. A cycloalkyl and a heterocycloalkyl may be linked to a parent group or a substrate in an arbitrary ring atom as long as the linkage satisfies valence requirements. Similarly, a cycloalkyl and a heterocycloalkyl may include one or more non-hydrogen substituents as long as the linkage satisfies valence requirements.

The term "carbonyl" refers to —C(O)R'. As used herein, (0) refers to a state in which oxygen is bound via a double bond to an atom such as carbon or sulfur. In this regard, R' refers to a non-hydrogen substituent such as a lower alkyl, a lower alkoxy, or the like. Non-limiting examples of the carbonyl group include 2-methoxyoxoethyl and 3-methoxyoxopropyl. A carbonyl may be linked to a parent group or a substrate in an arbitrary ring atom as long as the linkage satisfies valence requirements. Similarly, a carbonyl group may include one or more non-hydrogen substituent as long as the linkage satisfies valence requirements.

In addition, the benzimidazole derivative of Formula 1 may include a compound in the form of a racemate or isomer thereof.

In the benzimidazole derivative of Formula 1 of the present invention, $R_1$ represents 1,3-benzodioxolyl, 2,3-dihydro-1,4-benzodioxinyl, quinolinyl, or benzofuranyl; $R_2$ and $R_3$ are each independently hydrogen or hydroxy; $R_4$ is cyclohexyl, tetrahydropyranyl, or piperidinyl; and $R_4$ may be substituted or unsubstituted with a $C_4$-$C_{10}$ cycloalkylcarbonyl.

In another embodiment of the present invention, $R_1$ represents 1,3-benzodioxolyl, 2,3-dihydro-1,4-benzodioxinyl, quinolinyl, or benzofuranyl; $R_2$ and $R_3$ are each independently hydrogen or hydroxyl; and $R_4$ may be cyclohexyl, tetrahydropyranyl, or cyclopropyl methanone piperidinyl.

In another embodiment of the present invention, the benzimidazole derivative of Formula 1 may be 2-(quinoline-2-yl)-1-(2-((tetrahydro-2H-pyran-4-yl)amino)pyrimidin-4-yl)-1H-benzo[d]imidazole-5-ol; 2-(2,3-dihydrobenzo[b][1,4]dioxin-6-yl)-1-(2-((tetrahydro-2H-pyran-4-yl)amino)pyrimidin-4-yl)-1H-benzo[d]imidazole-5-ol; 2-(benzofuran-5-yl)-1-(2-((tetrahydro-2H-pyran-4-yl)amino)pyrimidin-4-yl)-1H-benzo[d]imidazole-5-ol; 1-(2-(cyclohexylamino)pyrimidin-4-yl)-2-(2,3-dihydrobenzo[b]

[1,4]dioxin-6-yl)-1H-benzo[d]imidazole-5-ol;
2-(benzofuran-5-yl)-1-(2-(cyclohexylamine)pyrimidien-4-yl)-1H-benzo[d]imidazole-5-ol; (S)-cyclopropyl(3-((4-(5-hydroxy-2-(quinoline-2-yl)-1H-benzo[d]imidazole-1-yl)pyrimidin-2-yl)amino)piperidine-1-yl)methanone; (S)-cyclopropyl(3-((4-(2-(2,3-dihydrobenzo[b][1,4]dioxin-6-yl)-5-hydroxy-1H-benzo[d]imidazole-1-yl)pyrimidin-2-yl)amino)piperidine-1-yl)methanone; (S)-(3-(4-(2-(benzofuran-5-yl)-5-hydroxy-1H-benz[d]imidazole-1-yl)pyrimidin-2-ylamino)piperidine-1-yl)(cyclopropyl)methanone; (S)-(3-(4-(2-(benzo[d][1,3]dioxol-5-yl)-5-hydroxy-1H-benz[d]imidazole-1-yl)pyrimidin-2-ylamino)piperidine-1-yl)(cyclopropyl)methanone; 2-(quinoline-2-yl)-1-(2-((tetrahydro-2H-pyran-4-yl)amino)pyrimidin-4-yl)-1H-benzo[d]imidazole-6-ol; 2-(2,3-dihydrobenzo[b][1,4]dioxin-6-yl)-1-(2-((tetrahydro-2H-pyran-4-ylamino)pyriidine-4-yl)-1H-benzo[d]imidazole-6-ol; 2-(benzofuran-5-yl)-1-(2-((tetrahydro-2H-pyran-4-yl)amino)pyrimidin-4-yl)-1H-benzo[d]imidazole-6-ol; 3-(2-(cyclohexylamino)pyrimidin-4-yl)-2-(quinoline-2-yl)-3H-benz[d]imidazole-5-ol; 1-(2-(cyclohexylamino)pyrimidin-4-yl)-2-(2,3-dihydrobenzo[b][1,4]dioxin-6-yl)-1H-benzo[d]imidazole-6-ol; 2-(benzofuran-5-yl)-1-(2-(cyclohexyl amino)pyrimidin-4-yl)-1H-benzo[d]imidazole-6-ol; (S)-cyclopropyl(3-(4-(6-hydroxy-2-(quinoline-2-yl)-1H-benzo[d]imidazole-1-yl)pyrimidin-2-ylamino)piperidine-1-yl)methanone; (S)-cyclopropyl(3-((4-(2-(2,3-dihydrobenzo[b][1,4]dioxin-6-yl)-6-hydroxy-1H-benzo[d]imidazole-1-yl)pyrimidin-2-yl)amino)piperidine-1-yl)methanone; (S)-(3-((4-(2-(benzofuran-5-yl)-6-hydroxy-1H-benzo[d]imidazole-1-yl)pyrimidin-2-yl)amino)piperidine-1-yl)(cyclopropyl)methanone; (R)-cyclopropyl(3-(4-(2-(2,3-dihydrobenzo[b][1,4]dioxin-6-yl)-5,6-dihydroxy-1H-benzo[d]imidazole-1-yl)pyrimidin-2-ylamino)piperidine-1-yl)methanone; or (R)-(3-(4-(2-(benzofuran-5-yl)-5,6-dihydroxy-1H-benzo[d]imidazole-1-yl)pyrimidin-2-ylamino)piperidine-1-yl)(cyclopropyl)methanone.

In particular, the benzimidazole derivative of Formula 1 may exhibit, as effects due to hetero-substituents introduced into the $R_1$ group, not only higher BBB permeability than that of conventional derivatives, but also enhanced liposolubility for the preparation of a drug according to the introduction of a hydroxy group, and thus may be expected to exhibit a stronger brain disease treatment effect.

Meanwhile, the compound of the present invention may be used in the form of a pharmaceutically acceptable salt, and as the salt, an acid addition salt formed by a pharmaceutically acceptable free acid is useful.

The term "salt" as used herein refers to an acid addition salt formed by a pharmaceutically acceptable free acid. The acid addition salt is obtained from: inorganic acids such as hydrochloric acid, nitric acid, phosphoric acid, sulfuric acid, hydrobromic acid, hydriodic acid, nitrous acid, and phosphorous acid; or nontoxic organic acids such as aliphatic mono- and dicarboxylates, phenyl-substituted alkanoates, hydroxy alkanoates and alkandioates, aromatic acids, and aliphatic and aromatic sulfonic acids. Examples of these pharmaceutically nontoxic salts include sulfates, pyrosulfates, bisulfates, sulfites, bisulfites, nitrates, phosphates, monohydrogen phosphates, dihydrogen phosphates, metaphosphates, pyrophosphate chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butyne-1,4-dioates, hexane-1,6-dioates, benzoates, chlorobenzoates, methylbenzoates, dinitro benzoates, hydroxybenzoates, methoxybenzoates, phthalates, terephthalates, benzenesulfonates, toluenesulfonates, chlorobenzene sulfonates, xylenesulfonates, phenylacetates, phenylpropionates, phenylbutyrates, citrates, lactates, β-hydroxybutyrates, glycolates, maleates, tartrates, methanesulfonates, propanesulfonates, naphthalene-1-sulfonates, naphthalene-2-sulfonates, and mandelates.

Acid addition salts according to the present invention may be prepared using a conventional method, for example, by dissolving the compounds of Formula 1 in an excess aqueous acid solution and precipitating the salt using a water-miscible organic solvent, e.g., methanol, ethanol, acetone, or acetonitrile. The acid addition salts may also be prepared by evaporating and drying the solvent or an excess acid in the resulting mixture or suction-filtering the precipitated salt.

In addition, pharmaceutically acceptable metallic salts may be prepared using bases. Alkali metal or alkaline earth metal salts are obtained by, for example, dissolving a compound in an excess alkali metal hydroxide or alkaline earth metal hydroxide solution, filtering a non-soluble compound salt, and evaporating and drying the filtrate. At this time, it is pharmaceutically preferable that a sodium salt, a potassium salt, or a calcium salt is prepared as a metal salt. In addition, silver salts corresponding thereto are obtained by reacting an alkali metal or an alkaline earth metal salt with a suitable silver salt (e.g., silver nitrate).

Moreover, the compound of the present invention includes not only pharmaceutically acceptable salts thereof, but also all salts, isomers, hydrates, and solvates that may be prepared using general methods.

Meanwhile, the benzimidazole derivative of Formula 1 according to the present invention may be prepared using several methods.

In one embodiment, as shown in Reaction Scheme 1 below, 60% NaH and a DMF solution were added to Compound 1a, Compound 14a, followed by stirring, a hydrogenation reaction, benzoimidazole formation using substituents ($R_1$), and an oxidation reaction using oxone to thereby synthesize Compounds 15a-g, Compounds 18a-g, and then each compound is subjected to a series of aromatic nucleophilic substitution reactions, thereby completing the synthesis of Compounds 9a-g, Compounds 10a-g, and Compounds 11a-g or Compounds 22a-g, Compounds 23a-g, and Compounds 25a-g, which are benzimidazole derivatives of the present invention.

[Reaction Scheme 1]

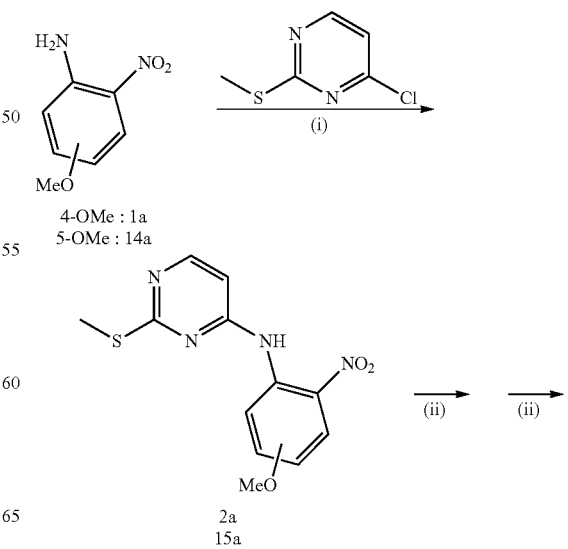

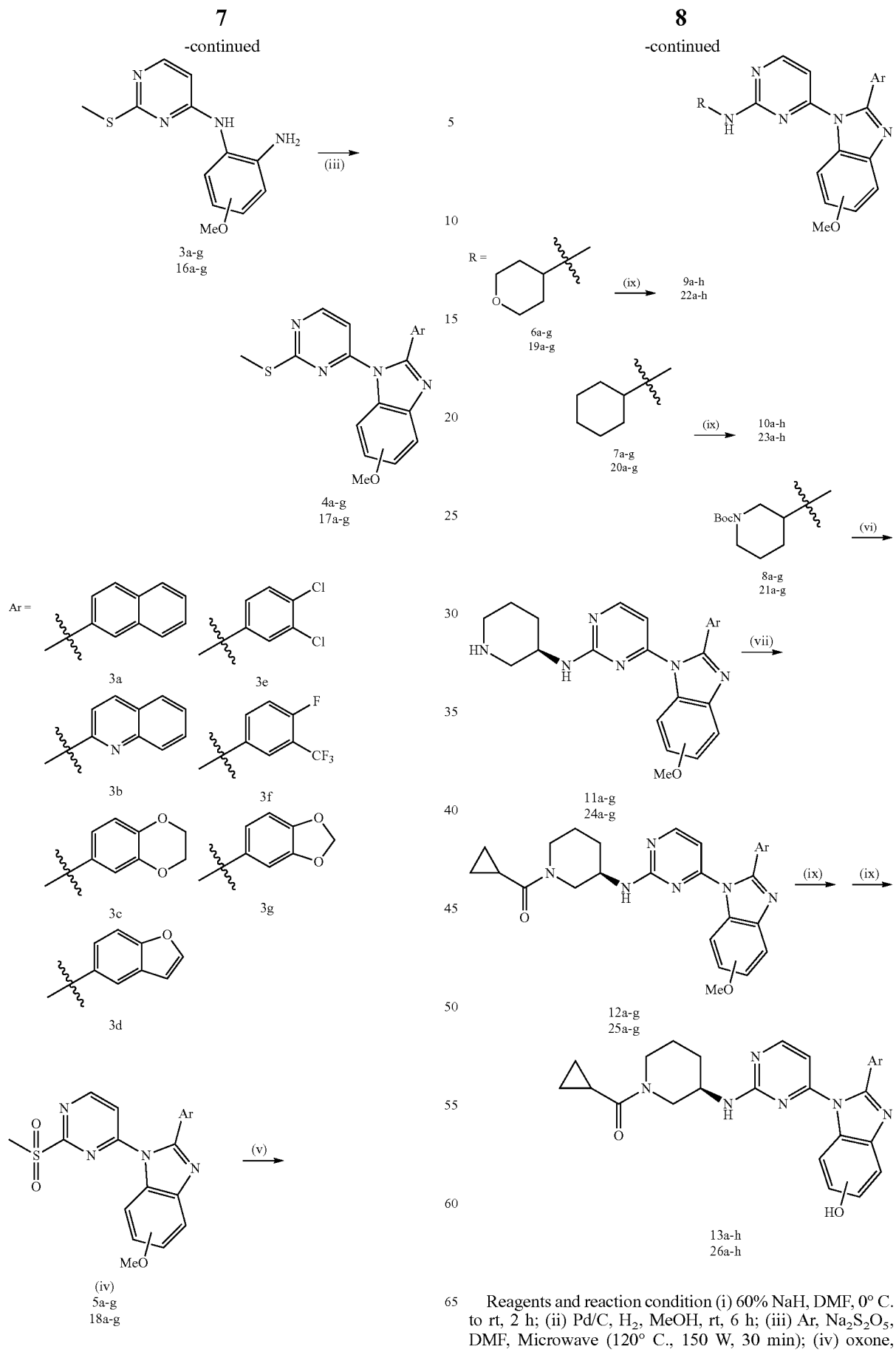
Reagents and reaction condition (i) 60% NaH, DMF, 0° C. to rt, 2 h; (ii) Pd/C, H₂, MeOH, rt, 6 h; (iii) Ar, Na₂S₂O₅, DMF, Microwave (120° C., 150 W, 30 min); (iv) oxone, MeOH:H₂O=1:1, rt, 1 h; (v) NH₂R, THF, 60° C., 5 h; (vi) 4N—HCl in 1,4-dioxane, rt, 20 min; (vii) cyclopropanecarbonyl chloride, TEA, THF, 0° C. to rt, 1 h; (ix) BBr₃, DCM, −78° C. to rt, 2 h In another embodiment, as shown in Reaction Scheme 2 below, Compounds 35a-g, which are benzimidazole derivatives of the present invention, were synthesized.

[Reaction Scheme 2]

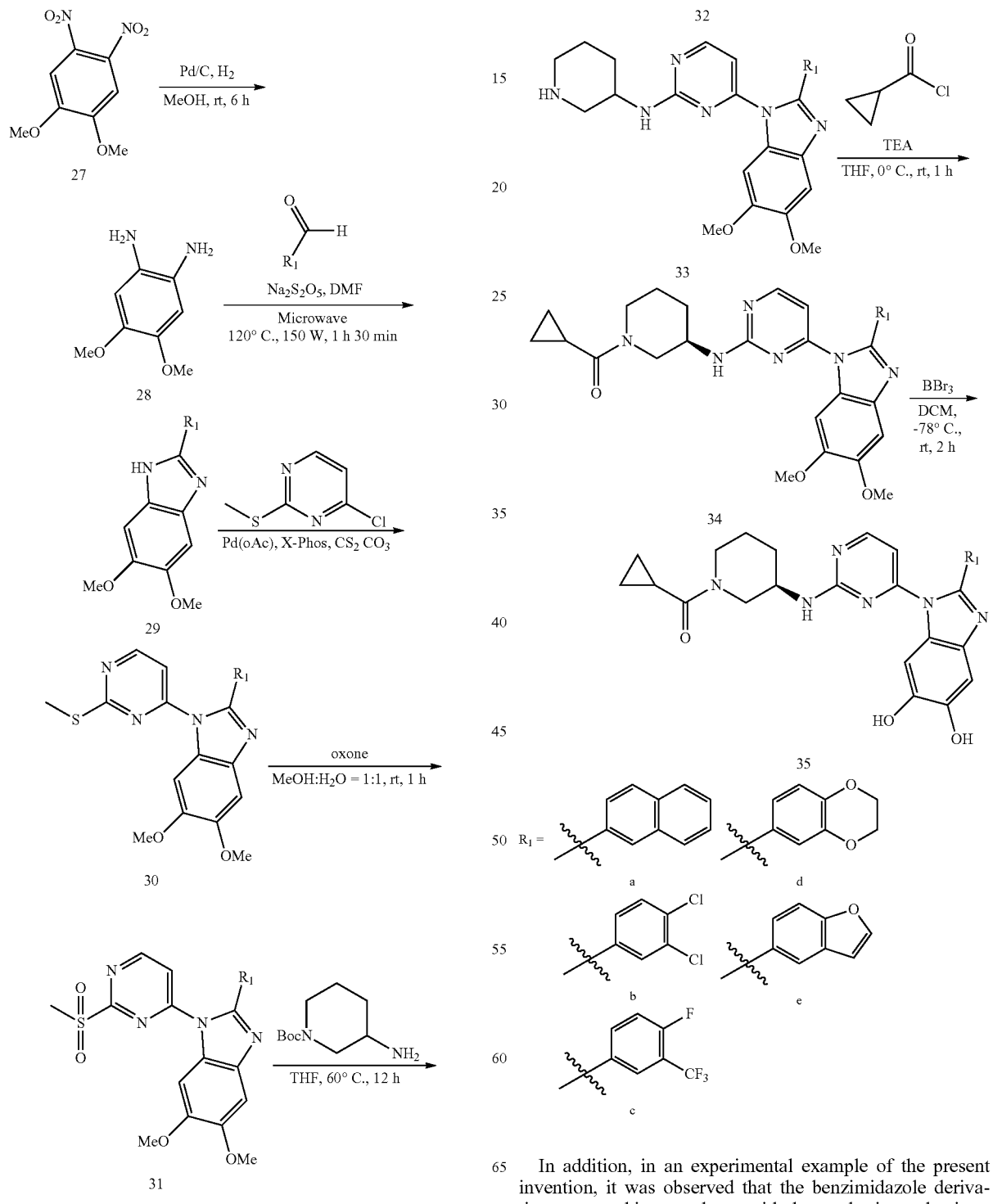

In addition, in an experimental example of the present invention, it was observed that the benzimidazole derivatives prepared in accordance with the synthesis mechanisms of Reaction Schemes 1 and 2 exhibited excellent JNK3 inhibitory activity and a consequent effect of reducing the concentration of beta-amyloid oligomer in brain tissue, and effectively permeated the blood-brain barrier compared to other drugs. Thus, through these experimental results, it was confirmed that the derivatives of the present invention could be effectively used as an active ingredient for the treatment of neurodegenerative brain diseases (see Experimental Examples 1 to 3).

Therefore, the present invention provides a pharmaceutical composition for the prevention or treatment of a neurodegenerative brain disease, which includes, as an active ingredient, the benzimidazole derivative of Formula 1 or a pharmaceutically acceptable salt thereof, a use of the benzimidazole derivative of Formula 1 or a pharmaceutically acceptable salt thereof for treating the above disease, and a method of treating the above disease, including administering, to an individual, a therapeutically effective amount of the compound of Formula 1 or a pharmaceutically acceptable salt thereof.

The term "prevention" as used herein means all actions that inhibit neurodegenerative brain diseases or delay the onset thereof via administration of the pharmaceutical composition according to the present invention.

The term "treatment" as used herein means all actions that alleviate or beneficially change symptoms due to neurodegenerative brain diseases via administration of the pharmaceutical composition according to the present invention.

The term "neurodegenerative brain disease", which is a disease to be prevented or treated by the composition of the present invention, may include diseases occurring due to brain damage without limitation, but preferably, the disease may be Alzheimer' disease, Parkinson' disease, Huntington's disease, multiple sclerosis, or stroke.

The pharmaceutical composition of the present invention includes a pharmaceutically acceptable carrier, in addition to the active ingredient. At this time, the pharmaceutically acceptable carrier, which is commonly used in formulation, may be lactose, dextrose, sucrose, sorbitol, mannitol, starch, acacia gum, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but the present invention is not limited thereto. In addition, the pharmaceutical composition may further include, in addition to the above-described components, a lubricant, a wetting agent, a sweetener, a flavor enhancer, an emulsifying agent, a suspension agent, a preservative, or the like.

The pharmaceutical composition of the present invention may be administered orally or parenterally (for example, intravenous administration, subcutaneous administration, intraperitoneal administration, or topical administration) according to a desired method, and a dose thereof may vary depending on the condition and body weight of a patient, the severity of diseases, drug form, administration route, and administration time, but may be appropriately selected by those of ordinary skill in the art.

The pharmaceutical composition of the present invention is administered in a pharmaceutically effective amount. The term "pharmaceutically effective amount" as used herein refers to an amount sufficient to treat diseases at a reasonable benefit/risk ratio applicable to medical treatment, and an effective dosage level may be determined according to factors including type of diseases of patients, the severity of disease, the activity of drugs, sensitivity to drugs, administration time, administration route, excretion rate, treatment period, and simultaneously used drugs, and other factors well known in the medical field. The pharmaceutical composition according to the present invention may be administered as an individual therapeutic agent or in combination with other therapeutic agents, sequentially or simultaneously with conventional therapeutic agents, and may be administered in a single dose or multiple doses. It is important to administer the pharmaceutical composition in the minimum amount that enables achievement of the maximum effects without side effects in consideration of all the above-described factors, and this may be easily determined by those of ordinary skill in the art.

In particular, an effective amount of the pharmaceutical composition of the present invention may vary according to the age, gender, condition, and body weight of a patient, the absorption, inactivity, and excretion rate of active ingredients in the body, the type of disease, and simultaneously used drugs, and the pharmaceutical composition may generally be administered in an amount of 0.001 mg/lkg (body weight) to 150 mg/kg, preferably 0.01 mg/kg to 100 mg/kg daily or every second day, or may be administered one to three times per day. However, the dosage may be increased or decreased according to administration route, the severity of obesity, gender, body weight, age, and the like, and thus the dosage is not intended to limit the scope of the present invention in any way.

The term "individual" as used herein refers to a subject with a disease requiring treatment and, more particularly, includes mammals such as humans, non-human primates, mice, rats, dogs, cats, horses, cows, and the like.

I. Synthesis of Benzimidazol-5-ol Derivatives

<Preparation Example 1-1> N-(4-methoxy-2-nitrophenyl)-2-(methylthio)pyrimidine-4-amine (2)

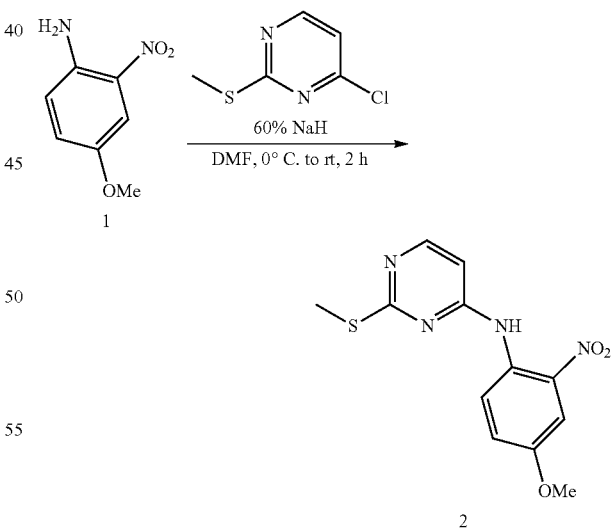

4-methoxy 2-nitrobenzene amine (Compound 1; 3 g, 17.85 mmol) was dissolved in DMF (89 ml), and 60% NaH (893 mg) was slowly added thereto at 0° C. Subsequently, the resulting solution was stirred for about 1 hour, 4-chloro-2-(methylthio)pyrimidine (5.73 g, 17.85 mmol) was added thereto, followed by stirring for about 2 hours. Thereafter, the mixed solvent was poured into iced water to be precipitated, and the precipitated reaction product was filtered to thereby obtain compound 2 (4 g, 78%).

$^1$H NMR (400 MHz, CDCl$_3$) δ 9.78 (s, 1H), 8.58 (d, J=9.3 Hz, 1H), 8.19 (d, J=5.8 Hz, 1H), 7.65 (d, J=3.0 Hz, 1H), 7.24 (dd, J=9.3, 3.0 Hz, 1H), 6.47 (d, J=5.8 Hz, 1H), 3.86 (s, 3H), 2.52 (s, 3H).

<Preparation Example 1-2> 4-methoxy-N-(2-(methylthio)pyrimidin-4-yl)benzene-1,2-diamine (3)

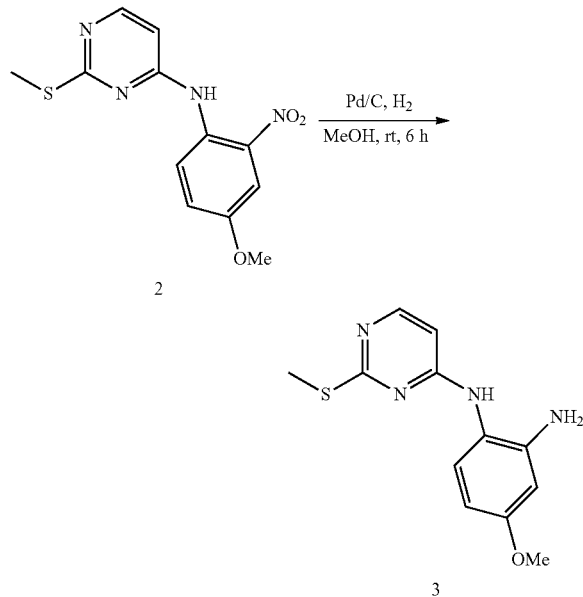

Compound 2 (1433 mg, 4.9 mmol) was dissolved in methanol (33 ml), 10% Pd/C (143 mg) was added thereto, and the resulting solution was stirred in the presence of hydrogen gas at room temperature for 5 hours. After the reaction was completed, the reaction product was filtered with Celite and the filtrate was distilled under reduced pressure. Compound 3 (1280 mg, 99%) was obtained from the residue without any purification.

$^1$H NMR (400 MHz, DMSO) δ 8.54 (s, 1H), 7.95 (d, J=5.9 Hz, 1H), 6.93 (d, J=5.9 Hz, 1H), 6.33 (d, J=2.8 Hz, 1H), 6.15 (dd, J=8.6, 2.8 Hz, 1H), 5.98 (s, 1H), 4.94 (s, 2H), 3.67 (s, 3H), 2.39 (s, 3H).

<Preparation Example 1-3> 5-methoxy-1-(2-(methylthio)pyrimidin-4-yl)-2-(naphthalene-2-yl)-1H-benzo[d]imidazole (4a)

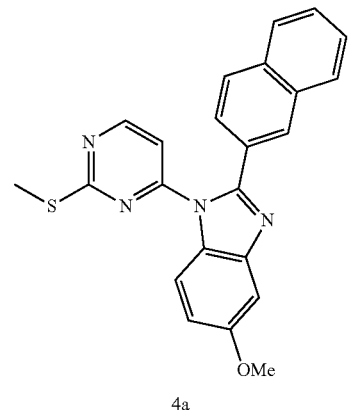

4a

Compound 3 (400 mg, 1.52 mmol), 2-naphthaldehyde (260 mg, 1.67 mmol), and Na$_2$S$_2$O$_5$ (1.45 g) were dissolved in DMF (3 ml), and the resulting solution was stirred in a microwave at 120° C. and 150 W for 1.5 hours. After confirming that the reaction was completed, the solvent was poured into iced water to be precipitated. The precipitated reaction product was filtered, and the filtrate was distilled under reduced pressure, and the residue was purified with column chromatography (silica gel, n-hexane:ethyl acetate=3:1), thereby obtaining compound 4a (370 mg, 50%).

$^1$H NMR (400 MHz, CDCl$_3$) δ 8.35 (d, J=5.4 Hz, 1H), 8.21 (d, J=1.3 Hz, 1H), 7.88 (d, J=1.8 Hz, 1H), 7.86-7.84 (m, 2H), 7.83 (s, 1H), 7.59-7.49 (m, 3H), 7.37 (d, J=2.5 Hz, 1H), 7.02 (dd, J=9.0, 2.5 Hz, 1H), 6.53 (d, J=5.4 Hz, 1H), 3.90 (s, 3H), 2.48 (s, 3H).

Compounds prepared according to Preparation Examples 1-4 to 1-9 were obtained in the same manner as in Preparation Example 1-3 (Compound 4b (360 mg, 59%), Compound 4c (403 mg, 59%), Compound 4d (325 mg, 64%), Compound 4e (588 mg, 86%), Compound 4f (370 mg, 56%), and Compound 4g (210 mg, 34%)).

<Preparation Example 1-4> 2-(5-methoxy-1-(2-(methylthio)pyrimidin-4-yl)-1H-benzo[d]imidazole-2-yl)quinolone (4b)

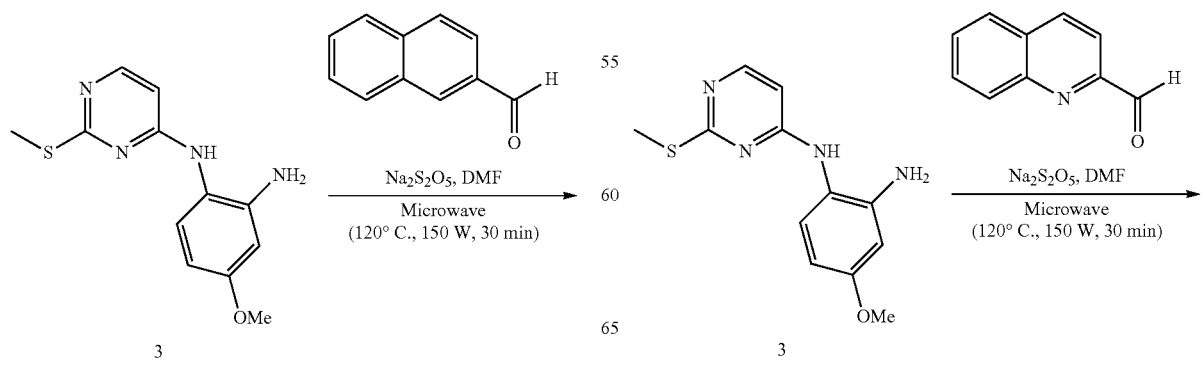

-continued

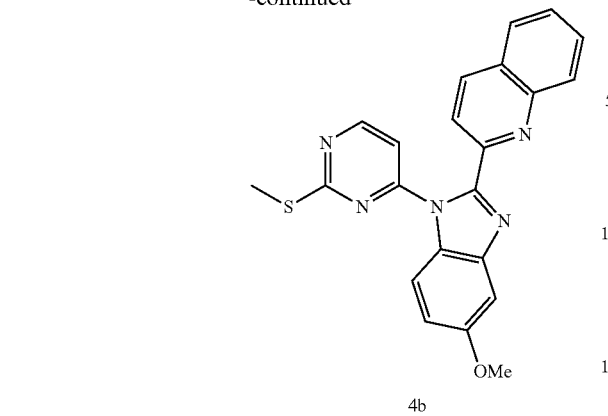

4b

¹H NMR (400 MHz, CDCl₃) δ 8.50 (d, J=5.3 Hz, 1H), 8.32 (d, J=8.5 Hz, 1H), 8.23 (d, J=8.5 Hz, 1H), 7.78 (d, J=8.1 Hz, 1H), 7.60 (dd, J=4.6, 2.0 Hz, 2H), 7.55 (d, J=9.0 Hz, 1H), 7.50 (m, 1H), 7.35 (d, J=2.4 Hz, 1H), 7.00 (dd, J=9.0, 2.4 Hz, 1H), 6.83 (d, J=5.3 Hz, 1H), 3.86 (s, 3H), 2.36 (s, 3H).

<Preparation Example 1-5> 2-(2,3-dihydrobenzo[b][1,4]dioxin-6-yl)-5-methoxy-1-(2-(methylthio)pyrimidin-4-yl)-1H-benzo[d]imidazole (4c)

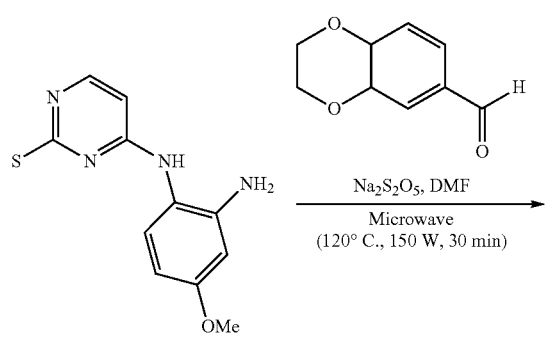

¹H NMR (400 MHz, CDCl₃) δ 8.42 (d, J=5.4 Hz, 1H), 7.76 (d, J=8.9 Hz, 1H), 7.30 (d, J=2.3 Hz, 1H), 7.13 (d, J=2.1 Hz, 1H), 7.00-6.93 (m, 2H), 6.86 (d, J=8.4 Hz, 1H), 6.56 (d, J=5.4 Hz, 1H), 4.28 (m, 2H), 4.27-4.23 (m, 2H), 3.87 (s, 3H), 2.54 (s, 3H).

<Preparation Example 1-6> 2-(benzofuran-5-yl)-5-methoxy-1-(2-(methylthio)pyrimidin-4-yl)-1H-benzo[d]imidazole (4d)

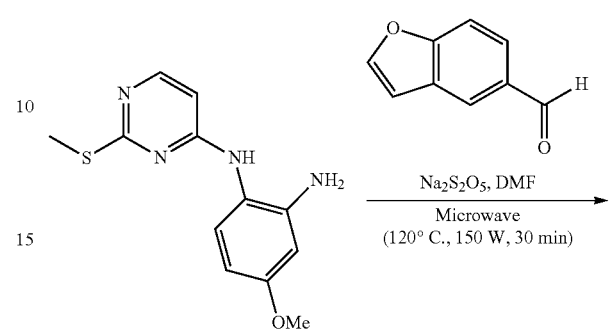

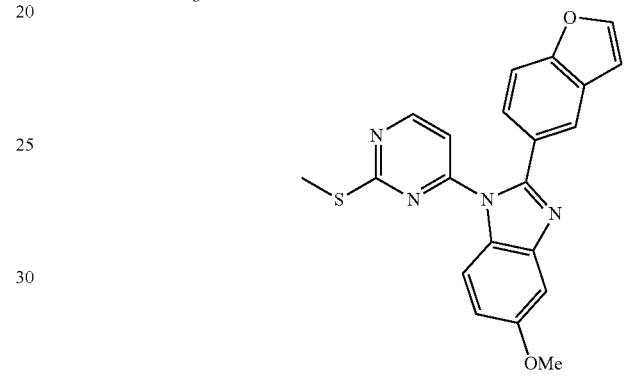

4d

¹H NMR (400 MHz, CDCl₃) δ 8.24 (d, J=5.4 Hz, 1H), 7.77 (d, J=1.4 Hz, 1H), 7.70 (d, J=8.9 Hz, 1H), 7.59 (d, J=2.2 Hz, 1H), 7.43 (d, J=8.6 Hz, 1H), 7.35 (dd, J=8.6, 1.7 Hz, 1H), 7.25 (d, J=2.4 Hz, 1H), 6.88 (dd, J=8.9, 2.5 Hz, 1H), 6.70 (dd, J=2.2, 0.8 Hz, 1H), 6.37 (d, J=5.4 Hz, 1H), 3.79 (s, 3H), 2.39 (s, 3H).

<Preparation Example 1-7> 2-(3,4-dichlorophenyl)-5-methoxy-1-(2-(methylthio)pyrimidin-4-yl)-1H-benzo[d]imidazole (4e)

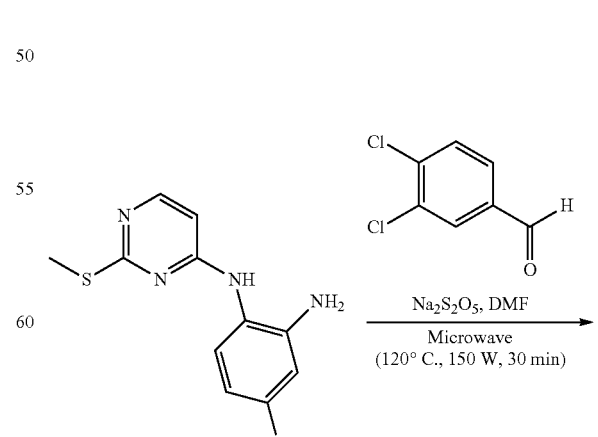

-continued

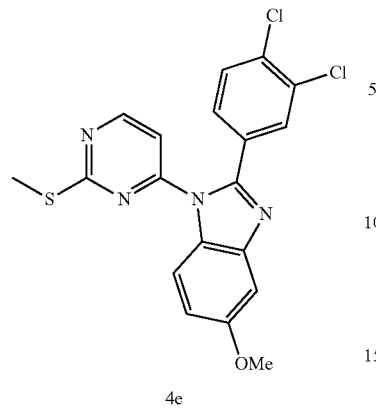

4e

¹H NMR (400 MHz, CDCl₃) δ 8.45 (d, J=5.3 Hz, 1H), 7.74 (d, J=2.3 Hz, 1H), 7.66 (d, J=9.0 Hz, 1H), 7.40 (d, J=8.3 Hz, 1H), 7.27-7.20 (m, 2H), 6.95 (dd, J=9.0, 2.3 Hz, 1H), 6.59 (d, J=5.3 Hz, 1H), 3.83 (s, 3H), 2.41 (s, 3H).

<Preparation Example 1-8> 2-(4-fluoro-3-(trifluoromethyl)phenyl)-5-methoxy-1-(2-(methylthio)pyrimidin-4-yl)-1H-benzo[d]imidazole (4f)

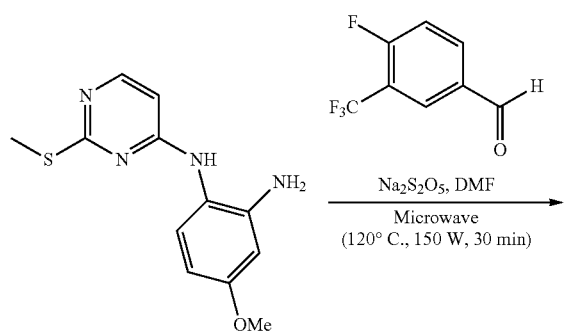

4f

¹H NMR (400 MHz, CDCl₃) δ 8.48 (d, J=5.3 Hz, 1H), 7.94 (dd, J=6.5, 1.5 Hz, 1H), 7.60 (d, J=9.0 Hz, 1H), 7.58-7.54 (m, 1H), 7.24 (d, J=2.2 Hz, 1H), 7.17 (m, 1H), 6.93 (dd, J=9.0, 2.2 Hz, 1H), 6.67 (d, J=5.3 Hz, 1H), 3.81 (s, 3H), 2.34 (s, 3H).

<Preparation Example 1-9> 2-(benzo[d][1,3]dioxole-5-yl)-5-methoxy-1-(2-(methylthio)pyrimidin-4-yl)-1H-benzo[d]imidazole (4g)

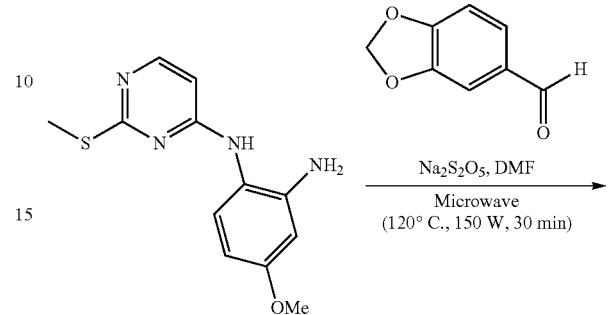

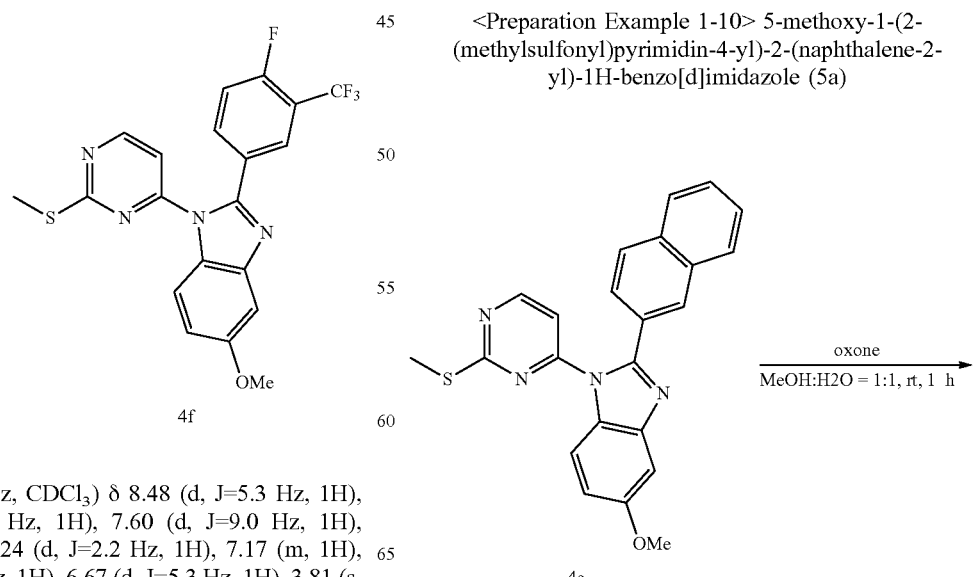

4g

¹H NMR (400 MHz, CDCl₃) δ 8.43 (d, J=5.4 Hz, 1H), 7.78 (d, J=8.9 Hz, 1H), 7.30 (d, J=2.4 Hz, 1H), 7.04 (d, J=1.4 Hz, 1H), 7.02 (dd, J=8.0, 1.7 Hz, 1H), 6.97 (dd, J=9.0, 2.5 Hz, 1H), 6.82 (d, J=8.0 Hz, 1H), 6.56 (d, J=5.4 Hz, 1H), 6.02 (s, 2H), 3.88 (s, 3H), 2.55 (s, 3H).

<Preparation Example 1-10> 5-methoxy-1-(2-(methylsulfonyl)pyrimidin-4-yl)-2-(naphthalene-2-yl)-1H-benzo[d]imidazole (5a)

4a

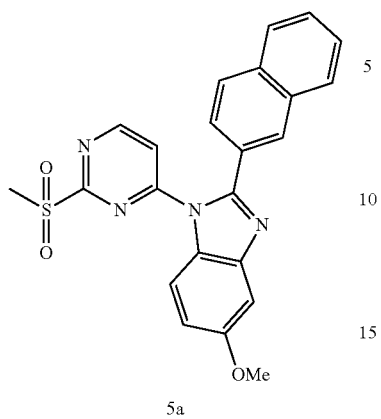

5a

Compound 4a (500 mg, 1.25 mg) and Potassium peroxomonosulfate (3.8 g) were dissolved in MeOH:H2O=1:1 mixed solvent (7 ml) and stirred at room temperature for 1 hour. After confirming the reaction, methanol was distilled off under reduced pressure. To the distilled mixture was diluted by addition of water and stirred until the product separated to a solid. The solid product was filtered off and washed with water and then the crude product was crystallized to obtain Compound 5a (530 mg, 98%).

$^1$H NMR (400 MHz, DMSO) δ 9.00 (d, J=5.6 Hz, 1H), 8.30 (s, 1H), 8.02 (d, J=8.9 Hz, 4H), 7.68-7.58 (m, 3H), 7.44 (d, J=5.6 Hz, 1H), 7.41 (t, J=3.5 Hz, 1H), 7.10 (dd, J=9.1, 2.4 Hz, 1H), 3.87 (s, 3H), 3.31 (s, 3H).

In the same manner as in Preparation Example 1-10, the compounds of Preparation Examples 1-12 to 1-16 were obtained. (Compound 5b (305 mg, 99%), 5c (315 mg, 90%), 5d (356 mg, 89%), 5e (220 mg, 95%), 5f (348 mg, 94%), 5g (200 mg, 87%)).

<Preparation Example 1-11> 2-(5-methoxy-1-(2-(methylsulfonyl)pyrimidin-4-yl)-1H-benzo[d]imidazole-2-yl)quinolone (5b)

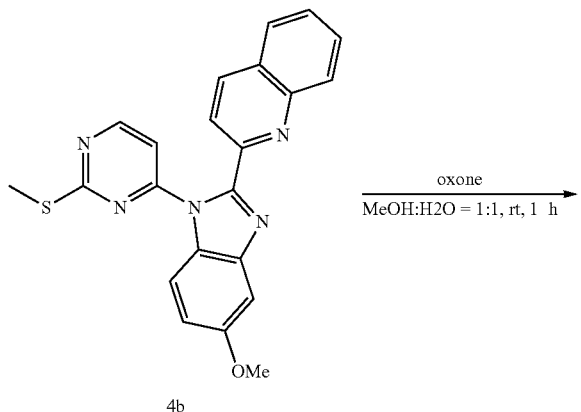

4b

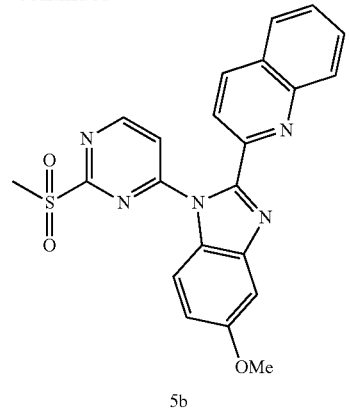

5b $^1$H NMR (400 MHz, DMSO) δ 9.17 (s, 1H), 8.59 (d, J=7.7 Hz, 1H), 8.39 (d, J=7.5 Hz, 1H), 8.04 (d, J=6.9 Hz, 1H), 7.94 (s, 1H), 7.71 (m, 2H), 7.64 (s, 1H), 7.45 (s, 1H), 7.38 (d, J=7.2 Hz, 1H), 7.10 (d, J=7.7 Hz, 1H), 3.86 (s, 3H), 3.35 (s, 3H).

<Preparation Example 1-12> 2-(2,3-dihydrobenzo[b][1,4]dioxin-6-yl)-5-methoxy-1-(2-(methylsulfonyl)pyrimidin-4-yl)-1H-benzo[d]imidazole (5c)

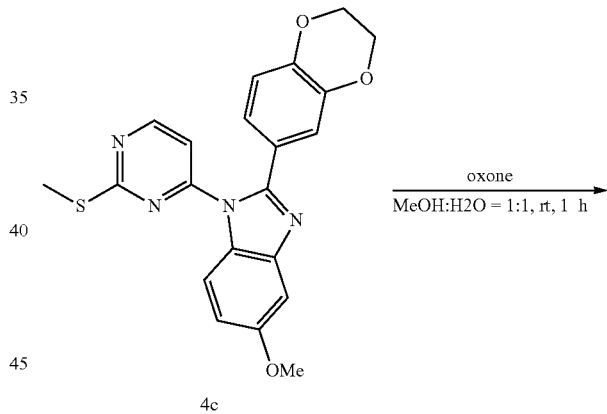

4c

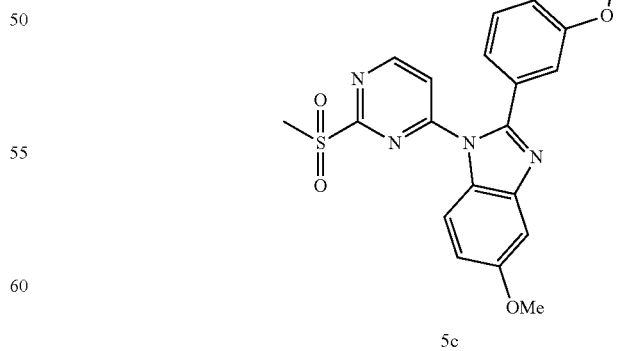

5c $^1$H NMR (400 MHz, DMSO) δ 9.12 (d, J=5.5 Hz, 1H), 7.93 (d, J=9.0 Hz, 1H), 7.51 (d, J=5.5 Hz, 1H), 7.37 (d, J=2.4 Hz, 1H), 7.19 (d, J=2.0 Hz, 1H), 7.10 (dd, J=9.0, 2.4 Hz,

1H), 7.02 (dd, J=8.4, 2.0 Hz, 1H), 6.97 (d, J=8.4 Hz, 1H), 4.33 (d, J=4.7 Hz, 2H), 4.30 (d, J=4.7 Hz, 2H), 3.86 (s, 3H), 3.41 (s, 3H).

<Preparation Example 1-13> 2-(benzofuran-5-yl)-5-methoxy-1-(2-(methylsulfonyl)pyrimidin-4-yl)-1H-benzo[d]imidazole (5d)

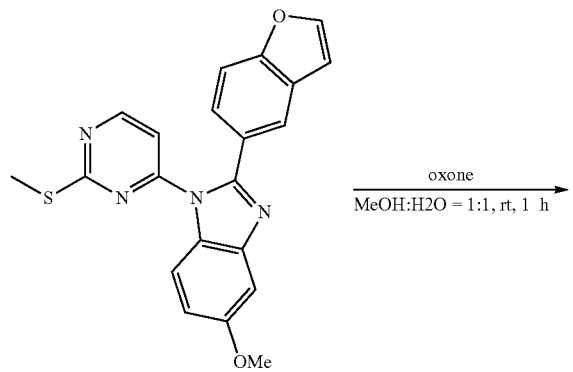

$^1$H NMR (400 MHz, DMSO) δ 9.07 (d, J=5.5 Hz, 1H), 8.15 (d, J=2.4 Hz, 1H), 8.03 (d, J=1.7 Hz, 1H), 8.01 (d, J=9.1 Hz, 1H), 7.76 (d, J=8.6 Hz, 1H), 7.56 (dd, J=8.6, 1.7 Hz, 1H), 7.43 (m, 2H), 7.16 (dd, J=9.1, 2.4 Hz, 1H), 7.09 (d, J=1.5 Hz, 1H), 3.88 (s, 3H), 3.36 (s, 3H).

<Preparation Example 1-14> 2-(3,4-dichlorophenyl)-5-methoxy-1-(2-(methylsulfonyl)pyrimidin-4-yl)-1H-benzo[d]imidazole (5e)

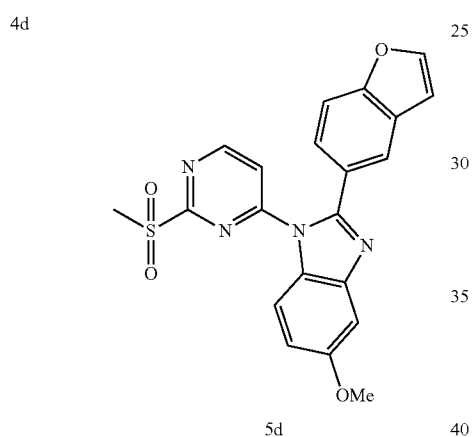

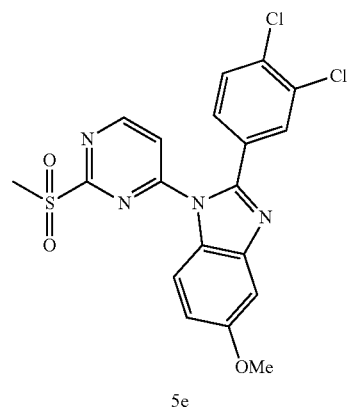

$^1$H NMR (400 MHz, DMSO) δ 9.10 (d, J=5.5 Hz, 1H), 7.97-7.94 (m, 2H), 7.71 (d, J=8.4 Hz, 1H), 7.60 (d, J=5.5 Hz, 1H), 7.52 (dd, J=8.4, 1.9 Hz, 1H), 7.38 (d, J=2.3 Hz, 1H), 7.09 (dd, J=9.0, 2.3 Hz, 1H), 3.85 (s, 3H), 3.35 (s, 3H).

<Preparation Example 1-15> 2-(4-fluoro-3-(trifluoromethyl)phenyl)-5-methoxy-1-(2-(methylsulfonyl)pyrimidin-4-yl)-1H-benzo[d]imidazole (5f)

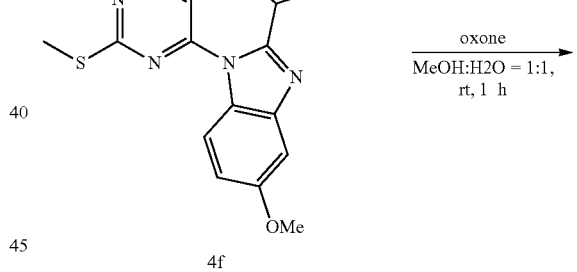

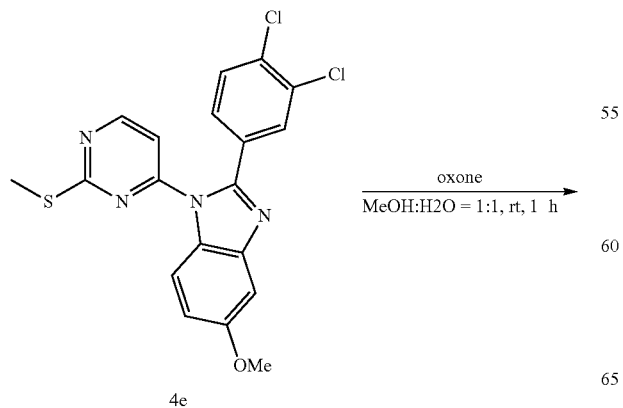

$^1$H NMR (400 MHz, DMSO) δ 9.12 (d, J=5.5 Hz, 1H), 8.10 (d, J=5.9 Hz, 1H), 7.96-7.88 (m, 2H), 7.66 (d, J=5.5 Hz, 1H), 7.61 (d, J=9.7 Hz, 1H), 7.39 (d, J=2.1 Hz, 1H), 7.08 (dd, J=9.0, 2.1 Hz, 1H), 3.85 (s, 3H), 3.33 (s, 3H).

<Preparation Example 1-16> 2-(benzo[d][1,3]diox-ole-5-yl)-5-methoxy-1-(2-(methylsulfonyl)pyrimi-din-4-yl)-1H-benzo[d]imidazole (5g)

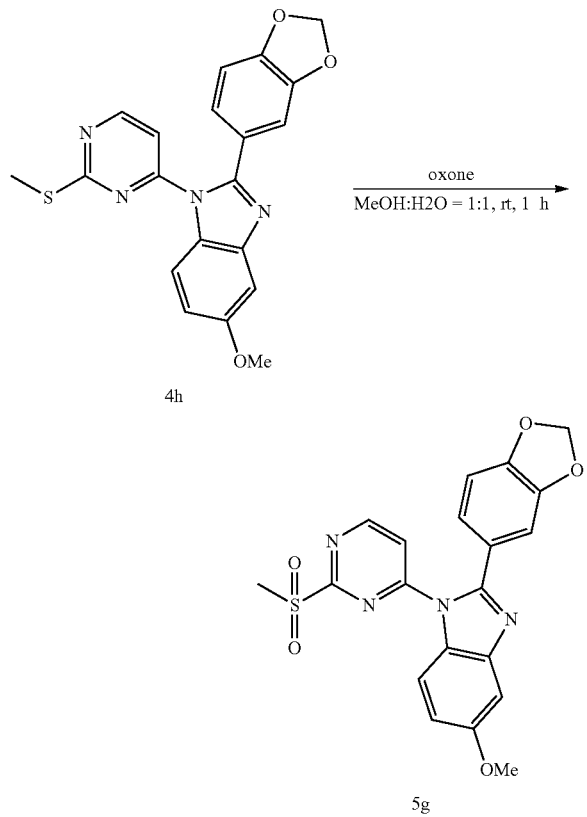

¹H NMR (400 MHz, DMSO) δ 9.11 (d, J=5.5 Hz, 1H), 7.96 (d, J=8.1 Hz, 1H), 7.49 (d, J=5.5 Hz, 1H), 7.37 (d, J=2.3 Hz, 1H), 7.21 (d, J=1.5 Hz, 1H), 7.13-7.08 (m, 2H), 7.05 (d, J=8.1 Hz, 1H), 6.15 (s, 2H), 3.86 (s, 3H), 3.42 (s, 3H).

<Preparation Example 1-17> 4-(5-methoxy-2-(naphthalene-2-yl)-1H-benzo[d]imidazole-1-yl)-N-(tetrahydro-2H-pyran-4-yl)pyrimidin-2-amine (6a)

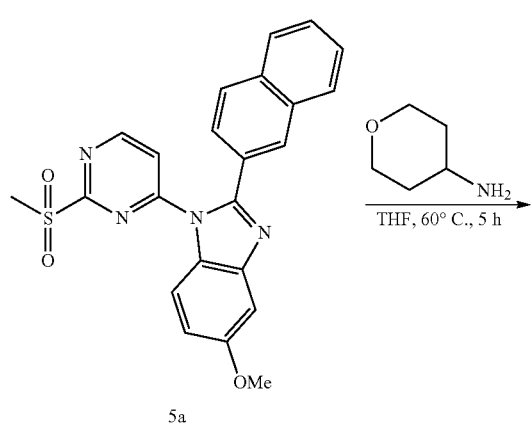

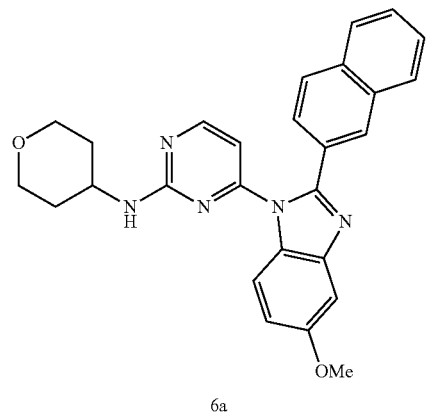

Compound 5a (43 mg, 0.1 mmol) and tetrahydro-2H-pyran-4-amine (21 ul) were dissolved in THF (1 ml) and stirred at 60° C. for 5 hours. After confirming that the reaction was completed, the reaction mixture was cooled to ambient temperature and the filtrate was distilled under reduced pressure, and the residue was purified by column chromatography (silica gel, n-hexane:ethyl acetate=2:1) to obtain Compound 6a (31 mg, 68%).

¹H NMR (400 MHz, CDCl₃) δ 8.27 (s, 1H), 8.23 (s, 1H), 7.92.7.76 (m, 3H), 7.67 (s, 1H), 7.56-7.45 (m, 3H), 7.38 (d, J=1.9 Hz, 1H), 6.99 (dd, J=8.9, 2.4 Hz, 1H), 6.38 (d, J=160.1 Hz, 1H), 5.47 (s, 1H), 3.90 (s, 3H), 3.50 (m, 2H), 3.39-3.21 (m, 1H), 2.93 (m, 1H), 1.58-1.30 (m, 2H), 1.24 (m, 2H), 1.15-0.81 (m, 1H).

In the same manner as in Preparation Example 1-17, the compounds of Preparation Examples 1-18 to 1-23 were obtained (Compound 6b (37 mg, 81%), 6c (44 mg, 83%), 6d (36 mg, 66%), 6e (33 mg, 51%), 6f (39 mg, 74%), 6g (27 mg, 55%)).

<Preparation Example 1-18> 4-(5-methoxy-2-(Quinoline-2-yl)-1H-benzo[d]imidazole-1-yl)-N-(tetrahydro-2H-pyran-4-yl)pyrimidine-2-amine (6b)

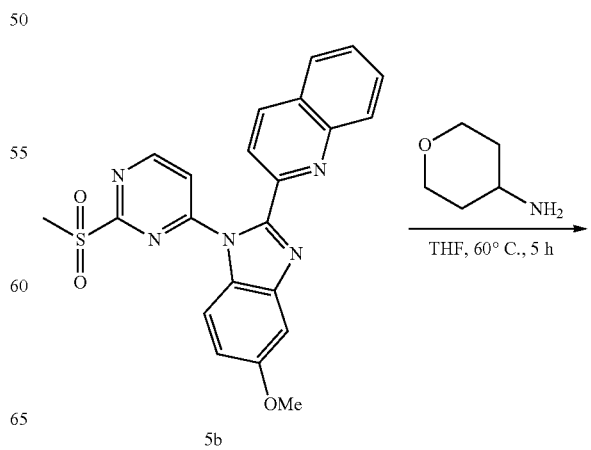

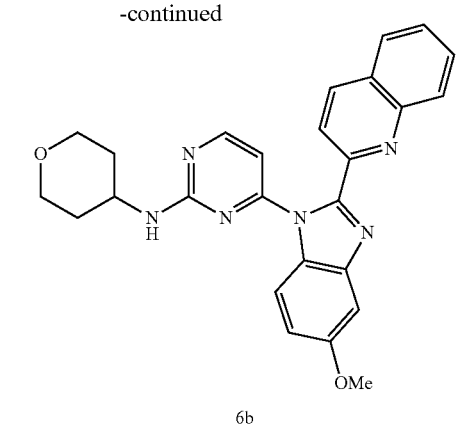

6b

¹H NMR (400 MHz, CDCl₃) δ 8.33 (d, J=5.3 Hz, 1H), 8.27 (d, J=7.9 Hz, 2H), 7.82 (d, J=7.9 Hz, 1H), 7.72 (d, J=8.1 Hz, 1H), 7.65 (m, 1H), 7.56-7.51 (m, 2H), 7.38 (d, J=2.3 Hz, 1H), 7.02 (dd, J=8.9, 2.3 Hz, 1H), 6.63 (s, 1H), 3.89 (s, 3H), 3.76 (m, 2H), 3.44 (s, 1H), 3.32-2.91 (m, 2H), 1.24 (m, 4H), 1.09-0.73 (m, 1H).

<Preparation Example 1-19> 4-(2-(2,3-dihydrobenzo[b][1,4]dioxin-6-yl)-5-methoxy-1H-benzo[d]imidazole-1-yl)-N-(tetrahydro-2H-pyran-4-yl)pyrimidin-2-amine (6c)

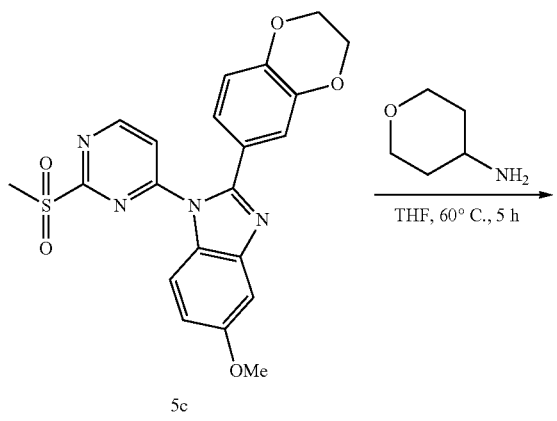

¹H NMR (400 MHz, CDCl₃) δ 8.26 (d, J=4.5 Hz, 1H), 7.59 (s, 1H), 7.31 (d, J=2.0 Hz, 1H), 7.13 (s, 1H), 7.04 (dd, J=8.4, 2.0 Hz, 1H), 6.92 (dd, J=8.9, 2.3 Hz, 1H), 6.85 (d, J=8.4 Hz, 1H), 6.40 (s, 1H), 4.25 (dd, J=11.3, 4.9 Hz, 4H), 3.95 (s, 1H), 3.86 (s, 3H), 3.49-3.31 (m, 2H), 1.76 (m, 2H), 1.50 (m, 3H), 1.30-1.18 (m, 1H), 1.01-0.78 (m, 1H).

<Preparation Example 1-20> 4-(2-(benzofuran-5-yl)-5-methoxy-1H-benzo[d]imidazole-1-yl)-N-(tetrahydro-2H-pyran-4-yl)pyrimidin-2-amine (6d)

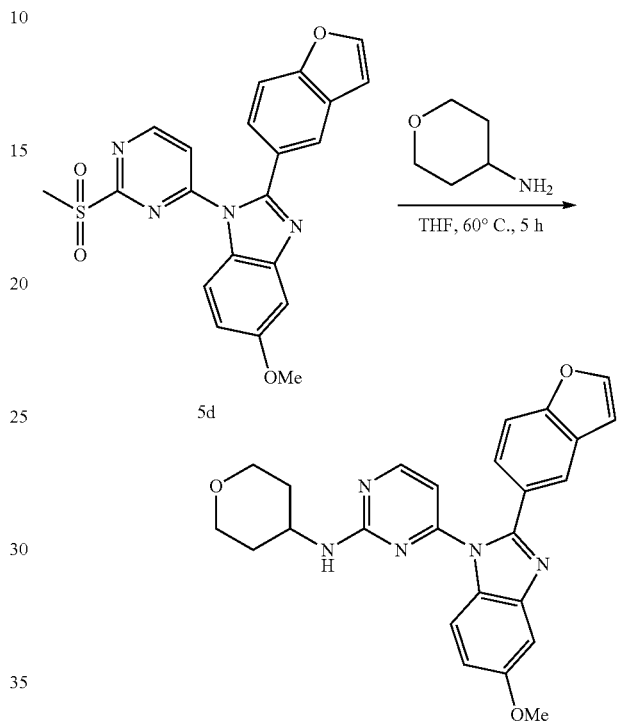

¹H NMR (400 MHz, CDCl₃) δ 8.24 (s, 1H), 7.91 (d, J=1.0 Hz, 1H), 7.67 (d, J=2.2 Hz, 1H), 7.66-7.55 (s, 1H), 7.50 (d, J=8.6 Hz, 1H), 7.44 (d, J=8.4 Hz, 1H), 7.36 (d, J=2.2 Hz, 1H), 6.97 (dd, J=8.9, 2.4 Hz, 1H), 6.80 (dd, J=2.1, 1.0 Hz, 1H), 6.45 (s, 1H), 3.88 (s, 3H), 3.76 (m, 1H), 3.52 (s, 1H), 3.17 (m, 1H), 2.13-1.84 (m, 1H), 1.56 (m, 2H), 1.48-1.28 (m, 2H), 1.27-1.20 (m, 1H), 1.03-0.74 (m, 1H).

<Preparation Example 1-21> 4-(2-(3,4-dichlorophenyl)-5-methoxy-1H-benzo[d]imidazole-1-yl)-N-(tetrahydro-2H-pyran-4-yl)pyrimidin-2-amine (6e)

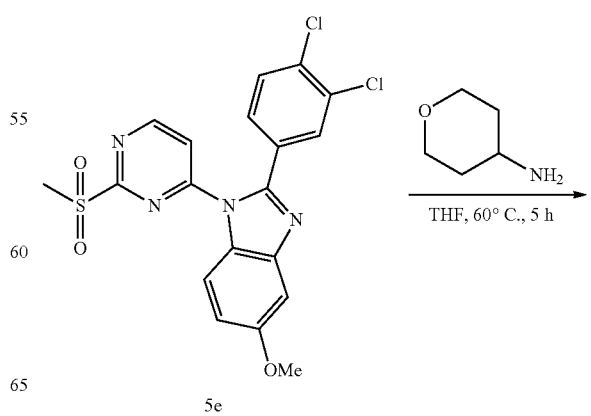

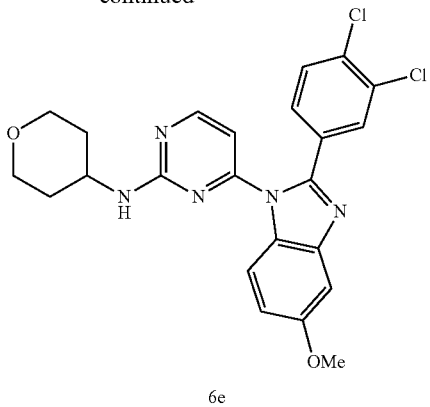

6e

¹H NMR (400 MHz, CDCl₃) δ 8.35 (d, J=3.8 Hz, 1H), 7.79 (s, 1H), 7.57 (s, 1H), 7.45 (d, J=8.3 Hz, 1H), 7.32 (m, 2H), 6.99 (dd, J=8.9, 2.0 Hz, 1H), 6.58 (s, 1H), 3.93 (s, 1H), 3.88 (s, 3H), 3.61-3.16 (m, 3H), 1.83-1.35 (m, 4H), 1.24 (m, 1H), 1.19-0.74 (m, 1H).

<Preparation Example 1-22> 4-(2-(4-fluoro-3-(trifluoromethyl)phenyl)-5-methoxy-1H-benzo[d]imidazole-1-yl)-N-(tetrahydro-2H-pyran-4-yl)pyrimidin-2-amine (6f)

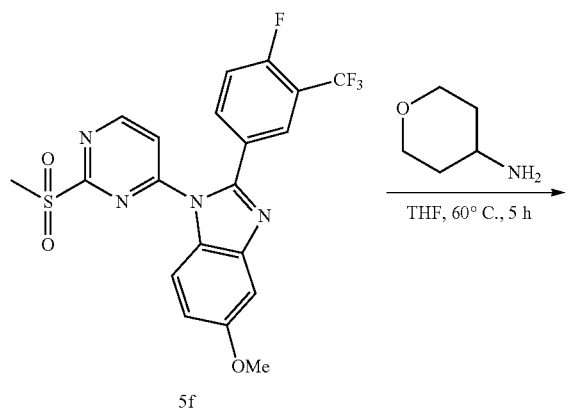

¹H NMR (400 MHz, CDCl₃) δ 8.37 (s, 1H), 7.95 (d, J=6.3 Hz, 1H), 7.71 (s, 1H), 7.57 (d, J=6.9 Hz, 1H), 7.33 (s, 1H), 7.22 (d, J=8.4 Hz, 1H), 7.00 (d, J=8.0 Hz, 1H), 6.56 (s, 1H), 3.88 (s, 3H), 3.52 (s, 1H), 3.45-3.21 (m, 2H), 2.24-1.82 (m, 1H), 1.61 (m, 2H), 1.55-1.39 (m, 2H), 1.33-1.17 (m, 1H), 0.98 (m, 1H).

<Preparation Example 1-23> 4-(2-(benzo[d][1,3]dioxole-5-yl)-5-methoxy-1H-benzo[d]imidazole-1-yl)-N-(tetrahydro-2H-pyran-4-yl)pyrimidin-2-amine (6g)

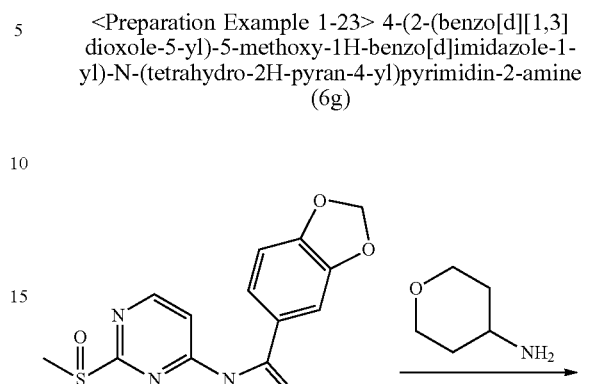

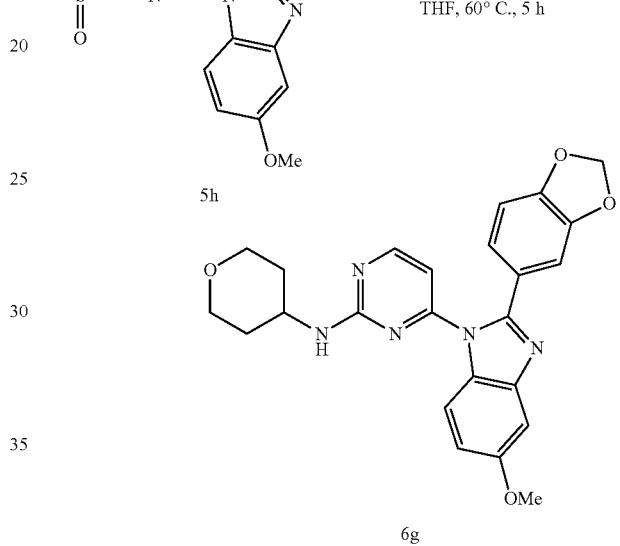

6g

¹H NMR (400 MHz, CDCl₃) δ 8.26 (d, J=5.1 Hz, 1H), 7.62 (s, 1H), 7.30 (d, J=1.8 Hz, 1H), 7.12-7.02 (m, 2H), 6.94 (dd, J=8.9, 2.4 Hz, 1H), 6.82 (d, J=8.3 Hz, 1H), 6.39 (s, 1H), 6.00 (s, 2H), 3.94 (m, 2H), 3.83-3.61 (br, 1H), 3.58-3.33 (m, 2H), 1.95-1.67 (m, 2H), 1.66-1.48 (m, 2H), 1.02-0.81 (m, 1H).

<Preparation Example 1-24> N-cyclohexyl-4-(5-methoxy-2-(naphthalene-2-yl)-1H-benzo[d]imidazole-1-yl)pyrimidin-2-amine (7a)

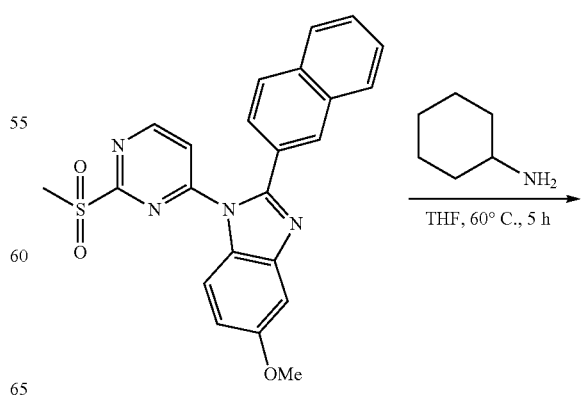

5a

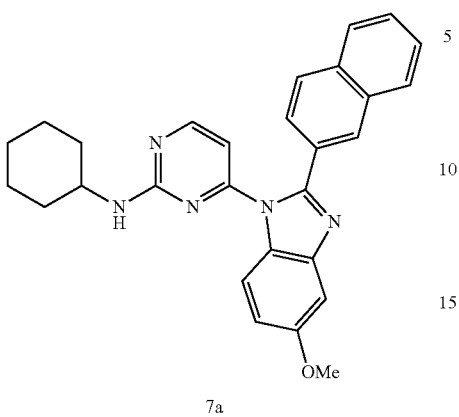

7a

Compound 5a (46 mg, 0.11 mmol) and cyclohexanamine (25 µl) were dissolved in THF (1.1 ml) and stirred at 60° C. for 5 hours. After completion of the reaction, the reaction mixture was cooled to ambient temperature and the filtrate was distilled under reduced pressure, and the residue was purified by column chromatography (silica gel, n-hexane: ethyl acetate=1:1) to obtain Compound 7a (37 mg, 75%).

$^1$H NMR (400 MHz, CDCl$_3$) δ 8.22 (s, 1H), 8.19 (d, J=5.1 Hz, 1H), 7.86-7.77 (m, 3H), 7.77-7.68 (m, 1H), 7.58-7.47 (m, 3H), 7.36 (d, J=2.5 Hz, 1H), 6.99 (dd, J=8.9, 2.5 Hz, 1H), 6.47-5.97 (m, 1H), 5.43 (s, 1H), 3.89 (s, 3H), 3.32 (m, 1H), 1.66 (m, 2H), 1.43 (m, 3H), 1.30-1.15 (m, 2H), 1.09-0.90 (m, 3H).

In the same manner as in Preparation Example 1-24, the compounds of Preparation Examples 1-25 to 1-30 were obtained (Compound 7b (35 mg, 67%), 7c (28 mg, 53%), 7d (35 mg, 53%), 7e (37 mg, 54%), 7f (34 mg, 65%), 7g (27 mg, 43%)).

<Preparation Example 1-25> N-cyclohexyl-4-(5-methoxy-2-(Quinoline-2-yl)-1H-benzo[d]imidazole-1-yl)pyrimidin-2-amine (7b)

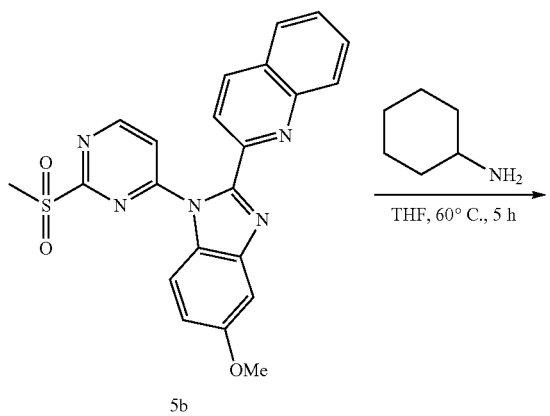

5b

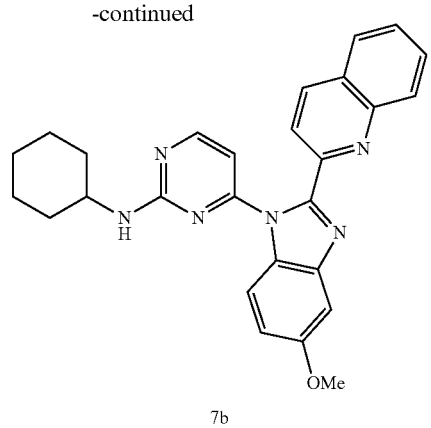

7b $^1$H NMR (400 MHz, CDCl$_3$) δ 8.25 (m, 3H), 7.82 (d, J=8.1 Hz, 1H), 7.74 (d, J=8.1 Hz, 1H), 7.68-7.62 (m, 1H), 7.60-7.51 (m, 2H), 7.38 (d, J=2.4 Hz, 1H), 7.02 (dd, J=8.9, 2.4 Hz, 1H), 6.52 (s, 1H), 3.89 (s, 3H), 3.68-3.17 (s, 1H), 1.45 (m, 5H), 1.26 (m, 2H), 1.18-0.90 (m, 4H).

<Preparation Example 1-26> N-cyclohexyl-4-(2-(2,3-dihydrobenzo[b][1,4]dioxin-6-yl)-5-methoxy-1H-benzo[d]imidazole-1-yl)pyrimidin-2-amine (7c)

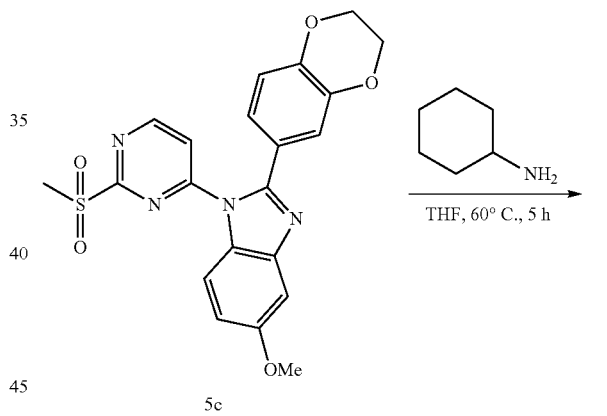

5c

7c $^1$H NMR (400 MHz, CDCl$_3$) δ 8.21 (d, J=5.3 Hz, 1H), 7.67 (d, J=9.0 Hz, 1H), 7.33 (d, J=1.8 Hz, 1H), 7.14 (s, 1H), 7.08-7.04 (m, 1H), 6.94 (dd, J=9.0, 2.4 Hz, 1H), 6.87 (d, J=8.4 Hz, 1H), 6.30 (s, 1H), 4.28 (d, J=5.1 Hz, 2H), 4.25 (d,

J=5.1 Hz, 2H), 3.87 (s, 3H), 3.74-3.57 (m, 1H), 1.87 (m, 1H), 1.71 (m, 2H), 1.61 (m, 1H), 1.35 (m, 3H), 1.19 (m, 4H).

<Preparation Example 1-27> 4-(2-(benzofuran-5-yl)-5-methoxy-1H-benzo[d]imidazole-1-yl)-N-cyclohexylpyrimidin-2-amine (7d)

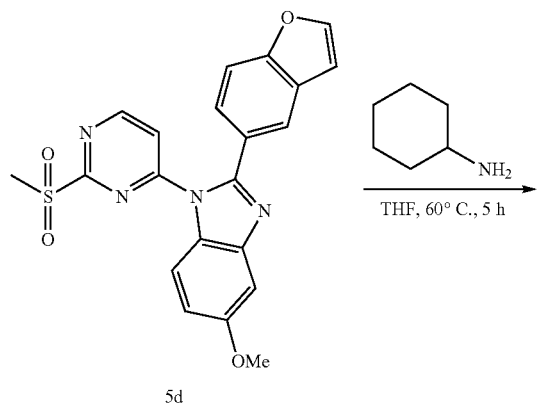

5d

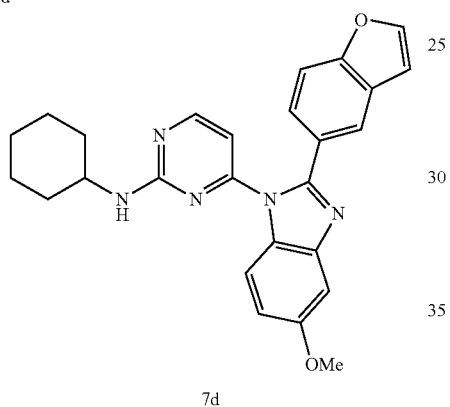

7d

¹H NMR (400 MHz, CD₃OD) δ 8.27 (d, J=1.6 Hz, 1H), 7.99 (dd, J=8.7, 1.6 Hz, 1H), 7.84 (d, J=4.5 Hz, 1H), 7.83 (d, J=2.3 Hz, 1H), 7.61 (d, J=8.7 Hz, 1H), 7.40 (d, J=8.6 Hz, 1H), 6.98-6.93 (m, 2H), 6.78 (dd, J=8.6, 2.3 Hz, 1H), 6.29 (d, J=7.2 Hz, 1H), 4.17-4.04 (m, 2H), 3.96 (s, 2H), 3.84-3.77 (m, 1H), 3.72 (m, 2H), 2.24 (m, 1H), 1.98-1.84 (m, 2H), 1.80-1.70 (m, 1H).

<Preparation Example 1-28> N-cyclohexyl-4-(2-(3,4-dichlorophenyl)-5-methoxy-1H-benzo[d]imidazole-1-yl)pyrimidin-2-amine (7e)

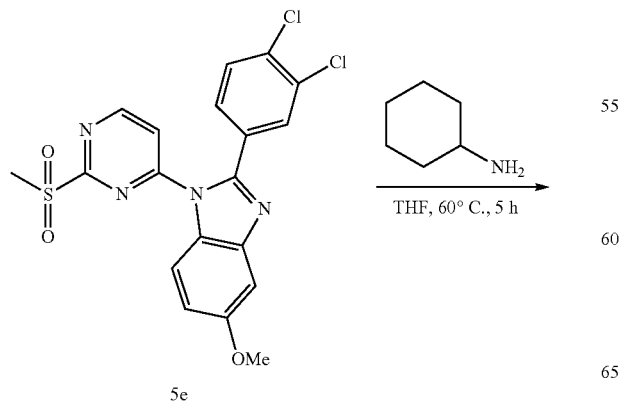

5e

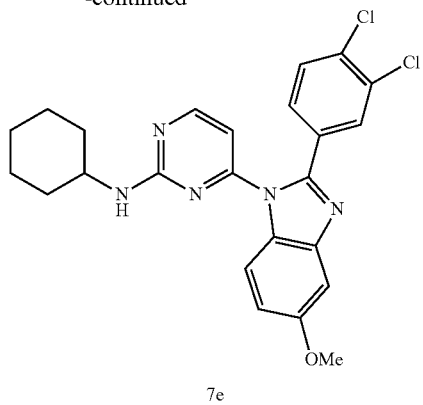

7e

¹H NMR (400 MHz, CDCl₃) δ 8.30 (d, J=5.3 Hz, 1H), 7.79 (s, 1H), 7.60 (d, J=9.0 Hz, 1H), 7.44 (d, J=8.3 Hz, 1H), 7.35-7.29 (m, 2H), 6.98 (dd, J=9.0, 2.4 Hz, 1H), 6.56-6.19 (s, br, 1H), 6.17-5.61 (s, br, 1H), 3.88 (s, 3H), 1.77-1.56 (m, 5H), 1.26-1.01 (m, 6H).

<Preparation Example 1-29> N-cyclohexyl-4-(2-(4-fluoro-3-(trifluoromethyl)phenyl)-5-methoxy-1H-benzo[d]imidazole-1-yl)pyrimidin-2-amine (7f)

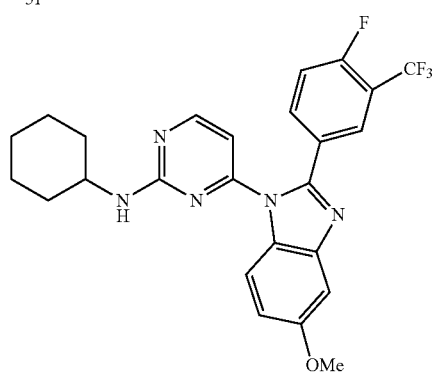

5f

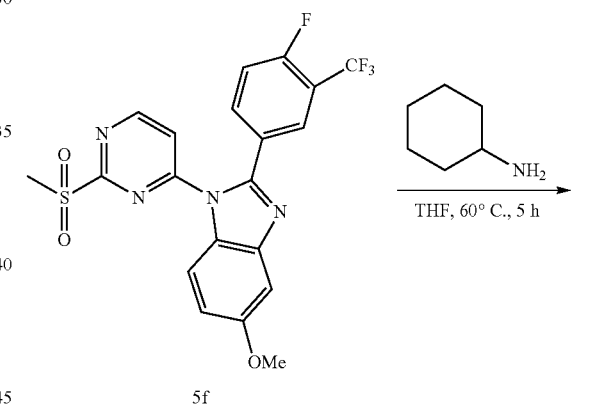

7f

¹H NMR (400 MHz, CDCl₃) δ 8.33 (d, J=4.8 Hz, 1H), 7.97 (d, J=5.3 Hz, 1H), 7.69 (s, 1H), 7.60 (d, J=9.0 Hz, 1H), 7.33 (d, J=2.0 Hz, 1H), 7.22 (m, 1H), 6.99 (dd, J=7.0, 2.0 Hz, 1H), 6.49 (s, 1H), 3.89 (s, 3H), 3.36 (s, 1H), 2.03 (m, 1H), 1.67 (m, 4H), 1.58 (m, 1H), 1.31 (m, 1H), 1.15 (m, 4H).

<Preparation Example 1-30> 4-(2-(benzo[d][1,3]dioxole-5-yl)-5-methoxy-1H-benzo[d]imidazole-1-yl)-N-cyclohexylpyrimidin-2-amine (7g)

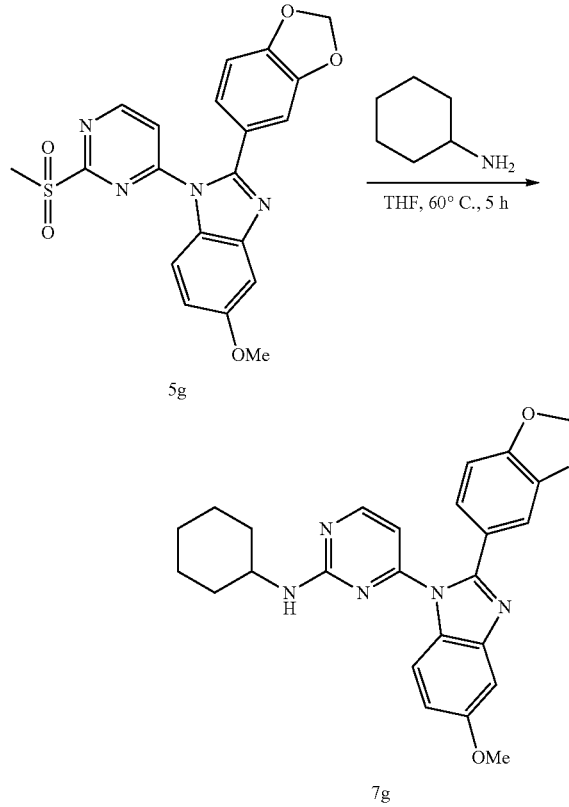

$^1$H NMR (400 MHz, CDCl$_3$) δ 8.24 (d, J=5.3 Hz, 1H), 7.67 (d, J=8.6 Hz, 1H), 7.56-7.40 (m, 1H), 7.28 (d, J=Hz, 1H), 5.99 (s, 2H), 3.86 (s, 3H), 3.73-3.40 (s, 1H), 2.16-1.84 (m, 2H), 1.81-1.57 (m, 3H), 1.26 (s, 6H). 2.3 Hz, 1H), 7.09-7.04 (m, 2H), 6.94 (dd, J=8.6, 2.3 Hz, 1H), 6.80 (d, J=8.1)

<Preparation Example 1-31> (S)-tert-butyl 3-((4-(5-methoxy-2-(naphthalene-2-yl)-1H-benzo[d]imidazole-1-yl)pyrimidin-2-yl)amino)piperidine-1-carboxylate (8a)

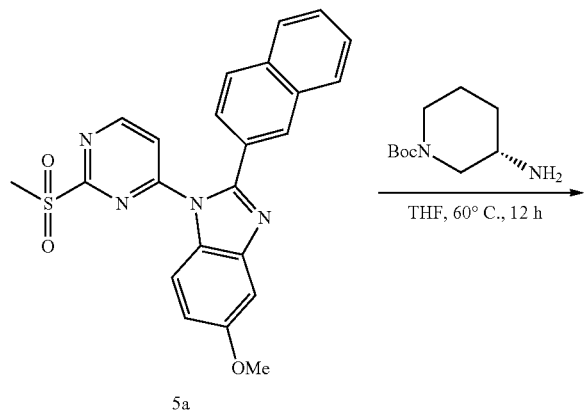

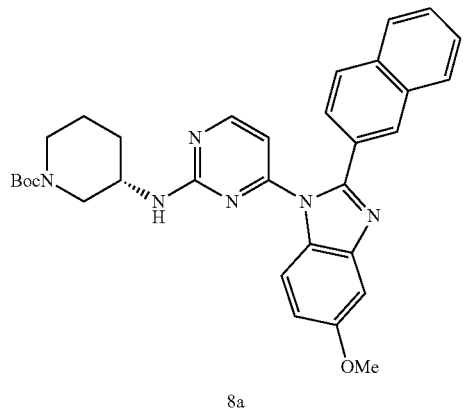

Compound 5a (218 mg, 0.506 mmol) and (S)-tert-butyl 3-aminopiperidine-1-carboxylate (199 μl) were dissolved in THF (3.4 ml) and stirred at 60° C. for 12 hours. After confirming the completion of the reaction, the reaction mixture was cooled to ambient temperature and the filtrate was distilled under reduced pressure, and the residue was purified by column chromatography (silica gel, n-hexane:ethyl acetate=1:1) to obtain Compound 8a (138 mg, 50%).

$^1$H NMR (400 MHz, CDCl$_3$) δ 8.24 (s, 1H), 8.18 (d, J=5.0 Hz, 1H), 7.85 (dd, J=18.9, 9.1 Hz, 3H), 7.78 (d, J=7.4 Hz, 1H), 7.58-7.49 (m, 3H), 7.38 (d, J=2.3 Hz, 1H), 7.01 (d, J=8.6 Hz, 1H), 6.22 (d, J=60.2 Hz, 1H), 3.90 (s, 3H), 3.75-3.50 (m, 2H), 3.39 (s, 1H), 3.31-3.13 (m, 2H), 2.16-1.89 (m, 1H), 1.43 (s, 9H), 1.32-1.22 (m, 3H), 0.97-0.79 (m, 1H).

In the same manner as in Preparation Example 1-31, the compounds of Preparation Examples 1-32 to 1-37 were obtained. (Compound 8b (100 mg, 50%), 8c (142 mg, 74%), 8d (130 mg, 66%), 8e (121 mg, 73%), 8f (143 mg, 73%), 8g (69 mg, 50%)).

<Preparation Example 1-32> (S)-tert-butyl 3-((4-(5-methoxy-2-(Quinoline-2-yl)-1H-benzo[d]imidazole-1-yl)pyrimidin-2-yl)amino)piperidine-1-carboxylate (8b)

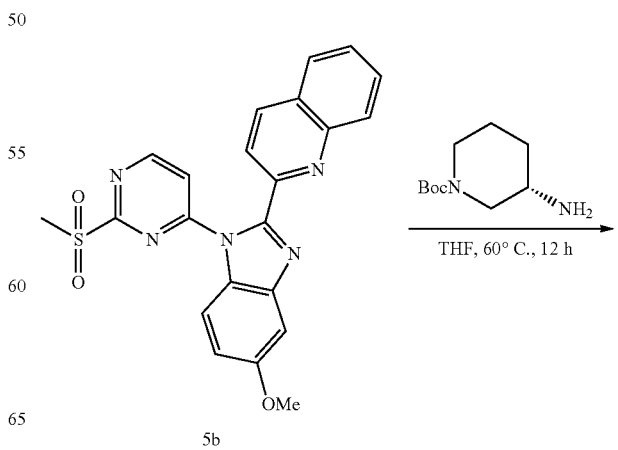

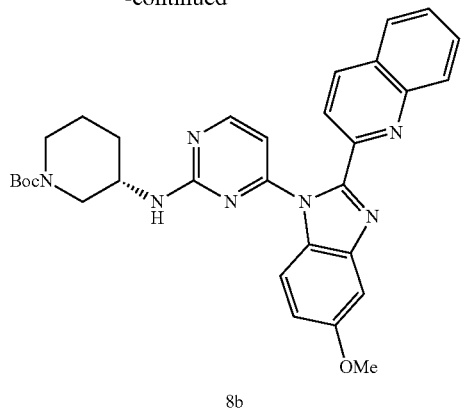

8b

¹H NMR (400 MHz, CDCl₃) δ 8.28 (m, J=8.4 Hz, 3H), 7.82 (d, J=8.0 Hz, 1H), 7.70 (s, 1H), 7.66 (d, J=7.5 Hz, 1H), 7.64-7.52 (m, 2H), 7.37 (d, J=2.3 Hz, 1H), 7.03 (d, J=8.0 Hz, 1H), 6.49 (d, J=5.4 Hz, 1H), 3.89 (s, 3H), 3.70 (s, 1H), 3.60-3.31 (m, 2H), 3.15 (m, 2H), 1.52 (m, 2H), 1.50-1.43 (m, 3H), 1.42-1.26 (s, 9H).

<Preparation Example 1-33> (S)-tert-butyl 3-((4-(2-(2,3-dihydrobenzo[b][1,4]dioxin-6-yl)-5-methoxy-1H-benzo[d]imidazol-1-yl)pyrimidin-2-yl)amino)piperidine-1-carboxylate (8c)

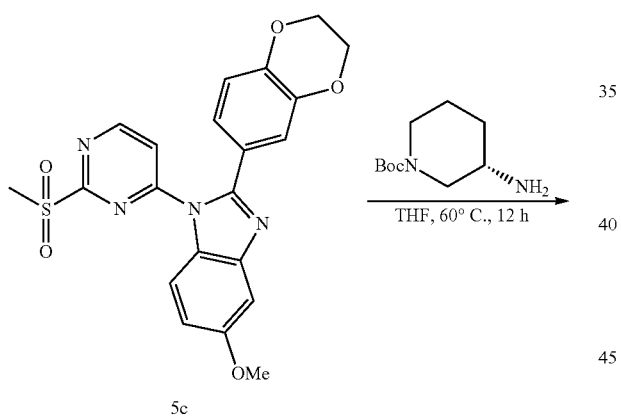

5c

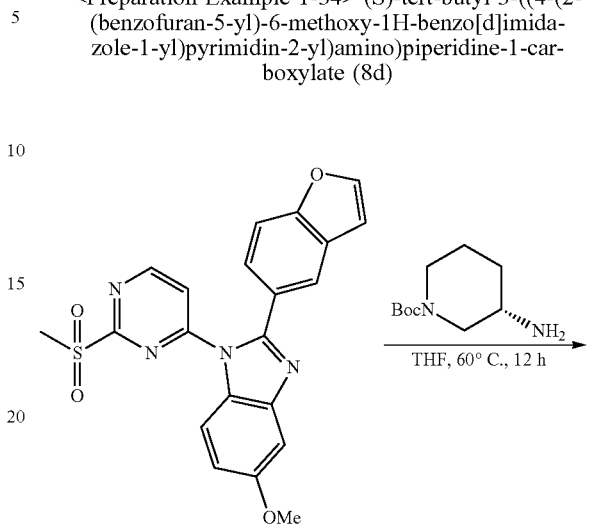

8c

¹H NMR (400 MHz, CDCl₃) δ 8.23 (d, J=5.0 Hz, 1H), 7.69 (d, J=8.5 Hz, 1H), 7.31 (s, 1H), 7.14 (s, 1H), 7.04 (d, J=7.9 Hz, 1H), 6.96 (d, J=2.0 Hz, 1H), 6.85 (d, J=8.4 Hz, 1H), 6.23 (s, 1H), 4.28 (d, J=4.9 Hz, 2H), 4.24 (d, J=4.9 Hz, 2H), 3.86 (s, 3H), 3.78 (s, 1H), 3.45 (m, 2H), 3.37 (m, 1H), 1.66 (m, 2H), 1.53 (m, 2H), 1.43 (s, 9H), 1.23 (m, 2H).

<Preparation Example 1-34> (S)-tert-butyl 3-((4-(2-(benzofuran-5-yl)-6-methoxy-1H-benzo[d]imidazol-1-yl)pyrimidin-2-yl)amino)piperidine-1-carboxylate (8d)

5d

8d

¹H NMR (400 MHz, CDCl₃) δ 8.12 (m, 2H), 7.71 (dd, J=7.2, 3.4 Hz, 2H), 7.61-7.48 (m, 3H), 7.03 (m, 1H), 6.87 (d, J=1.6 Hz, 1H), 6.29 (s, 1H), 3.91 (s, 3H), 3.85-3.42 (m, 3H), 3.27 (s, 2H), 1.73 (m, 3H), 1.44 (m, 9H), 1.12-0.78 (m, 1H).

<Preparation Example 1-35> (S)-tert-butyl 3-((4-(2-(3,4-dichlorophenyl)-5-methoxy-1H-benzo[d]imidazol-1-yl)pyrimidin-2-yl)amino)piperidine-1-carboxylate (8e)

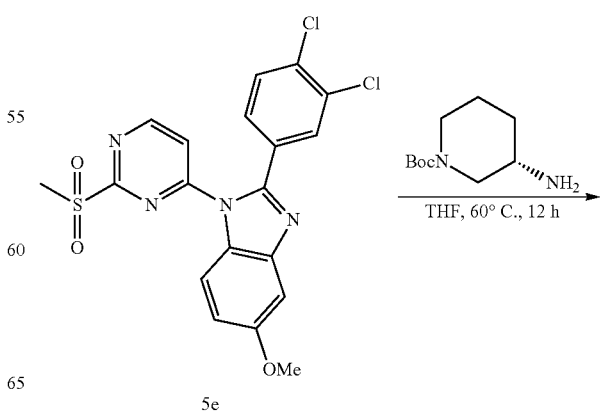

5e

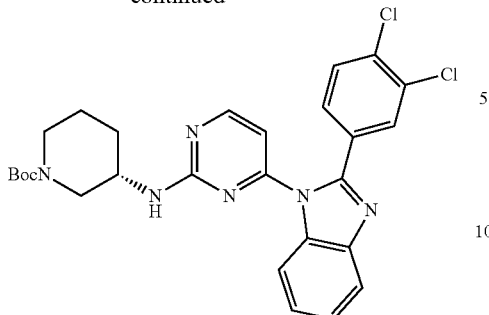

8e

¹H NMR (400 MHz, CDCl₃) δ 8.27 (d, J=5.2 Hz, 1H), 7.77 (d, J=2.0 Hz, 1H), 7.60 (d, J=8.8 Hz, 1H), 7.39 (d, J=8.3 Hz, 1H), 7.27-7.24 (m, 2H), 6.94 (d, J=2.5 Hz, 1H), 6.40-6.14 (m, 1H), 3.83 (s, 3H), 3.68-3.52 (s, 1H), 3.45 (m, 1H), 3.30 (s, 1H), 3.25 (m, 2H), 1.63 (m, 2H), 1.41 (s, 9H), 1.32-1.23 (m, 2H).

<Preparation Example 1-36> (S)-tert-butyl 3-((4-(2-(4-fluoro-3-(trifluoromethyl)phenyl)-5-methoxy-1H-benzo[d]imidazole-1-yl)pyrimidin-2-yl)amino)piperidine-1-carboxylate (8f)

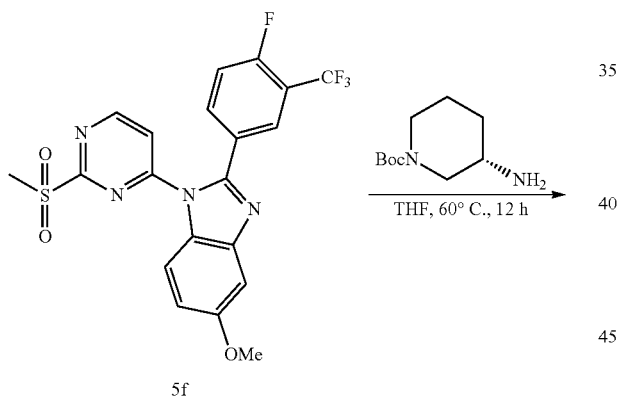

5f

8f

¹H NMR (400 MHz, CDCl₃) δ 8.31 (s, 1H), 7.95 (d, J=9.0 Hz, 1H), 7.69 (s, 1H), 7.63 (s, 1H), 7.31 (d, J=2.1 Hz, 1H), 7.22 (m, 1H), 7.06-6.95 (m, 1H), 6.32 (s, 1H), 3.87 (s, 3H), 3.63 (m, 1H), 3.45 (s, 1H), 3.26 (m, 2H), 2.01-1.81 (m, 1H), 1.68 (m, 2H), 1.52-1.34 (s, 9H), 1.25 (m, 2H), 0.85 (m, 1H).

<Preparation Example 1-37> (S)-tert-butyl 3-((4-(2-(benzo[d][1,3]dioxole-5-yl)-5-methoxy-1H-benzo[d]imidazole-1-yl)pyrimidin-2-yl)amino)piperidine-1-carboxylate (8g)

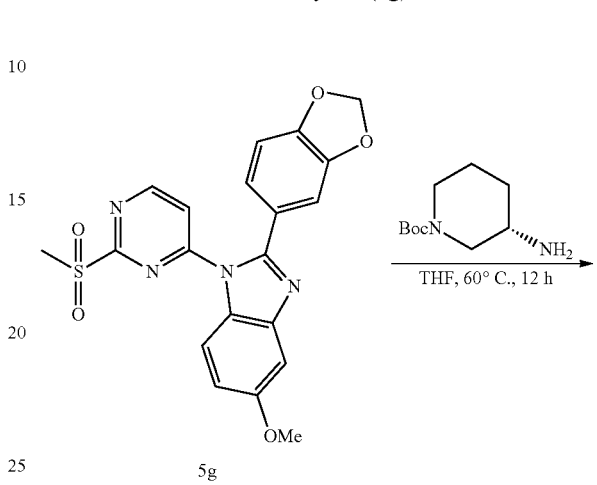

5g

8g

¹H NMR (400 MHz, CD₃OD) δ 8.40 (s, 1H), 7.61 (s, 1H), 7.30 (s, 1H), 7.00 (m, 3H), 6.87 (s, 1H), 6.45 (s, 1H), 6.02 (s, 2H), 4.08 (s, 1H), 3.85 (s, 3H), 3.62 (s, 1H), 3.35 (m, 1H), 2.99 (m, 2H), 2.00 (m, 2H), 1.71 (m, 3H), 1.23 (m, 1H).

<Example 1-1> 2-(naphthalene-2-yl)-1-(2-((tetrahydro-2H-pyran-4-yl)amino)pyrimidin-4-yl)-1H-benzo[d]imidazole-5-ol (9a)

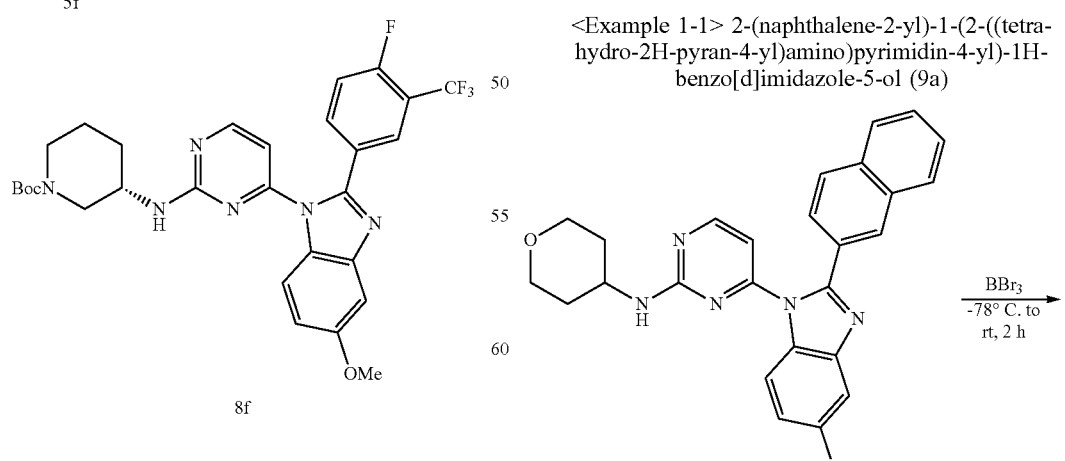

6a

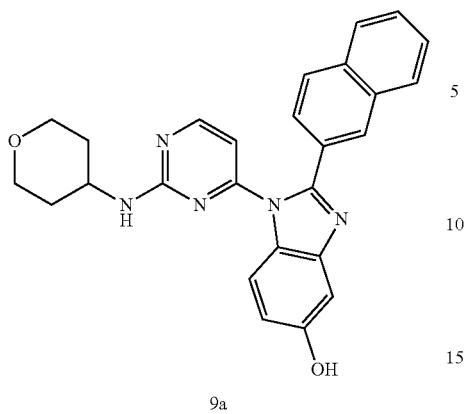

9a

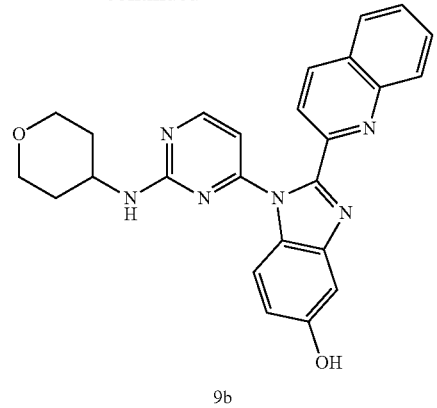

9b

Compound 6a (24 mg, 0.053 mmol) was dissolved in methylene chloride (0.5 ml), BBr$_3$ (25 µl) was added at −78° C., stirred for about 1 hour, and then stirred at room temperature for about 2 hours. After confirming the completion of the reaction, methanol was added and quenched. The organic solvent was distilled under reduced pressure, extracted with methylene chloride, and washed with a saturated NaHCO$_3$ aqueous solution. The extracted organic layer was dried over magnesium sulfateanhydrous, filtered, and the filtrate was distilled under reduced pressure, and the residue was purified by column chromatography (silica gel, methylene chloride:MeOH=20:1) to obtain Compound 9a (20 mg, 86%).

$^1$H NMR (400 MHz, CDCl$_3$) δ 8.26 (s, 1H), 8.20 (d, J=1.6 Hz, 1H), 7.76-7.85 (m, 3H), 7.63 (s, 1H), 7.49-7.54 (m, 3H), 7.36 (d, J=2.4 Hz, 1H), 6.98 (dd, J=8.8 Hz, J=2.4 Hz, 1H), 6.34 (br, s, 1H), 5.34 (d, J=7.6 Hz, 1H), 3.89 (s, 3H), 3.49-3.62 (m, 2H), 3.24-3.42 (m, 1H), 2.80-3.03 (m, 2H), 1.07-1.46 (m, 2H).

In the same manner as in Example 1-1, the compounds of Examples 1-2 to 1-5 were obtained (Compound 9b (19 mg, 59%), 9c (13 mg, 36%), 9d (30 mg, 93%), 9f (10 mg, 30%)).

<Example 1-2> 2-(quinoline-2-yl)-1-(2-((tetra-hydro-2H-pyran-4-yl)amino)pyrimidin-4-yl)-1H-benzo[d]imidazole-5-ol (9b)

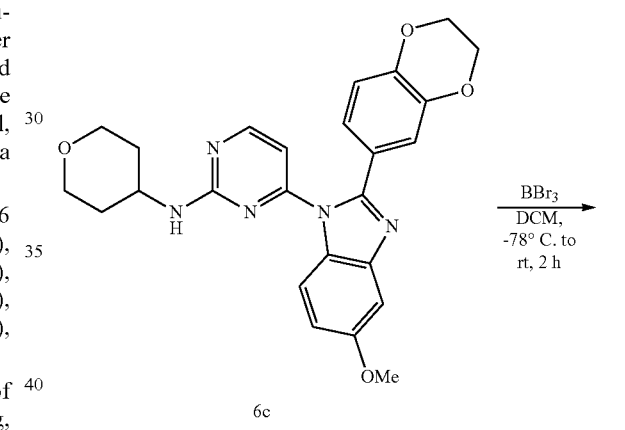

<Example 1-3> 2-(2,3-dihydrobenzo[b][1,4]dioxin-6-yl)-1-(2-((tetrahydro-2H-pyran-4-yl)amino)pyrimidin-4-yl)-1H-benzo[d]imidazole-5-ol (9c)

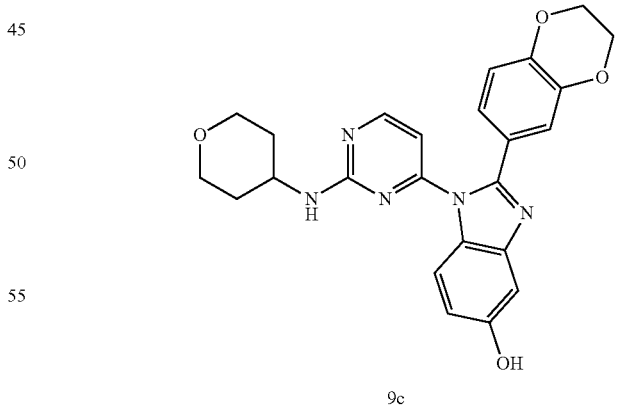

$^1$H NMR (400 MHz, MeOD) δ 8.17 (d, J=8.9 Hz, 1H), 8.07 (d, J=7.2 Hz, 1H), 7.21 (d, J=2.1 Hz, 1H), 7.15-7.08 (m, 2H), 6.99 (d, J=8.4 Hz, 1H), 6.93 (dd, J=8.9, 2.4 Hz, 1H), 6.33 (d, J=7.2 Hz, 1H), 4.35-4.30 (m, 4H), 4.09-4.01 (s, 1H), 3.68 (m, 1H), 2.47-2.34 (m, 2H), 2.28-2.20 (m, 1H), 2.13-1.98 (m, 3H), 1.55 (m, 1H), 1.29 (m, 2H).

<Example 1-4> 2-(benzofuran-5-yl)-1-(2-((tetra-hydro-2H-pyran-4-yl)amino)pyrimidin-4-yl)-1H-benzo[d]imidazole-5-ol (9d)

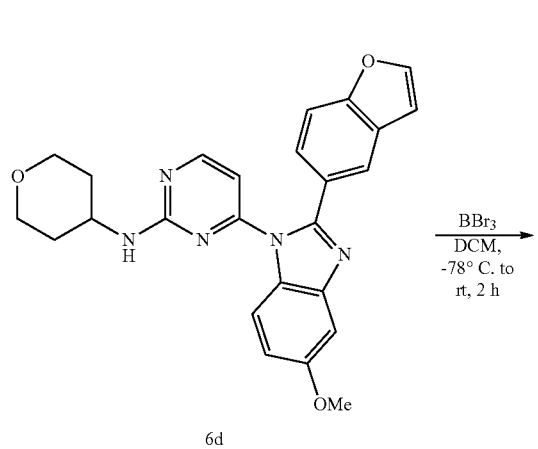

6d

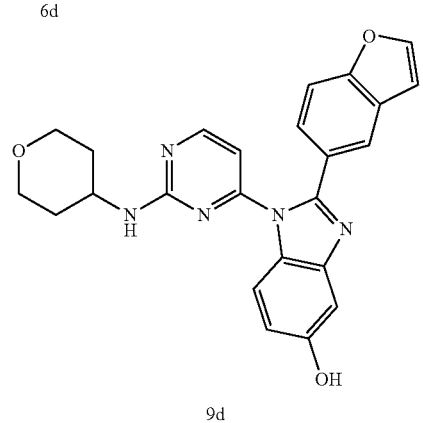

9d

¹H NMR (400 MHz, CD₃OD) δ 8.27 (d, J=1.6 Hz, 1H), 7.99 (dd, J=8.7, 1.6 Hz, 1H), 77.84 (d, J=4.5 Hz, 1H), 7.83 (d, J=2.3 Hz, 1H), 7.61 (d, J=8.7 Hz, 1H), 7.40 (d, J=8.6 Hz, 1H), 6.98-6.93 (m, 2H), 6.78 (dd, J=8.6, 2.3 Hz, 1H), 6.29 (d, J=7.2 Hz, 1H), 4.17-4.04 (m, 2H), 3.96 (s, 2H), 3.84-3.77 (m, 1H), 3.72 (m, 2H), 2.24 (m, 1H), 1.98-1.84 (m, 2H), 1.80-1.70 (m, 1H).

<Example 1-5> 2-(4-fluoro-3-(trifluoromethyl)phe-nyl)-1-(2-((tetrahydro-2H-pyran-4-yl)amino)pyrimi-din-4-yl)-1H-benzo[d]imidazole-5-ol (9f)

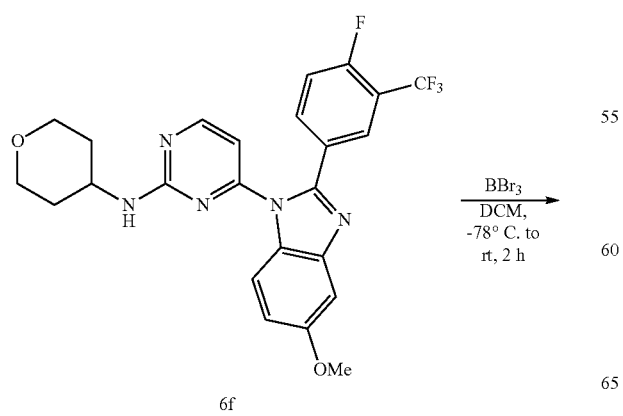

6f

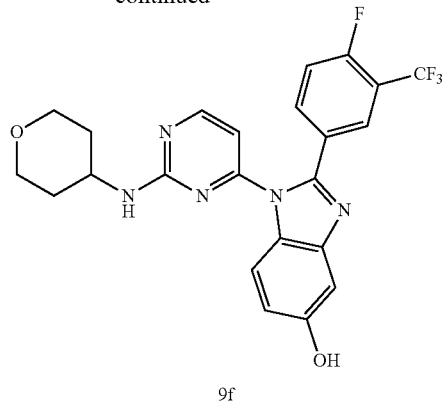

9f

¹H NMR (400 MHz, CD₃OD) δ 8.40 (dd, J=6.7, 2.0 Hz, 1H), 8.32 (m, 1H), 7.94 (d, J=7.2 Hz, 1H), 7.55-7.49 (m, 1H), 7.44 (d, J=8.7 Hz, 1H), 6.97 (s, 1H), 6.82 (dd, J=8.7, 2.3 Hz, 1H), 6.40 (d, J=7.2 Hz, 1H), 4.25-4.13 (m, 2H), 3.91-3.82 (s, 1H), 3.81-3.73 (m, 2H), 2.36-2.27 (m, 1H), 2.02-1.91 (m, 2H), 1.84-1.74 (m, 1H), 1.29 (m, 1H), 1.07-0.78 (m, 1H).

<Example 1-6> 1-(2-(cyclohexylamino)pyrimidin-4-yl)-2-(naphthalene-2-yl)-1H-benzo[d]imidazole-5-ol (10a)

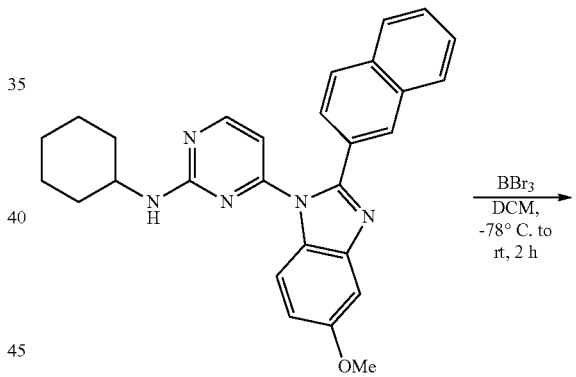

7a

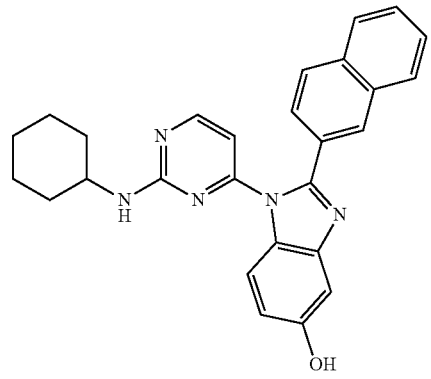

10a

Compound 7a (37 mg, 0.082 mmol) was dissolved in methylene chloride (0.8 ml), BBr₃ (39 al) was added at −78° C., stirred for about 1 hour, and then stirred at room temperature for about 2 hours. After confirming the completion of the reaction, methanol was added and quenched. The organic solvent was distilled under reduced pressure, extracted with methylene chloride, and washed with a saturated NaHCO₃ aqueous solution. The extracted organic layer was dried over magnesium sulfateanhydrous, filtered, and the filtrate was distilled under reduced pressure, and the residue was purified by column chromatography (silica gel, methylene chloride:MeOH=20:1) to obtain Compound 10a (21 mg, 58%).

$^1$H NMR (400 MHz, DMSO-d6) δ 9.35 (s, 1H), 8.40 (s, 1H), 8.21 (s, 1H), 7.95-8.00 (m, 2H), 7.52-7.80 (m, 4H), 7.29 (s, 1H), 7.14 (s, 1H), 6.87 (dd, J=8.8 Hz, J=2.4 Hz, 1H), 6.71 (s, 1H), 5.22 (br, s, 1H), 2.90 (br, s, 1H), 1.15-1.25 (m, 6H), 0.67-0.91 (m, 4H).

In the same manner as in Example 1-6, the compounds of Examples 1-7 to 1-11 were obtained (Compound 10b (17 mg, 51%), 10c (13 mg, 53%), 10d (20 mg, 60%), 10e (10 mg, 54%), 10f (20 mg, 74%)).

<Example 1-7> 1-(2-(cyclohexylamino)pyrimidin-4-yl)-2-(Quinoline-2-yl)-1H-benzo[d]imidazole-5-ol (10b)

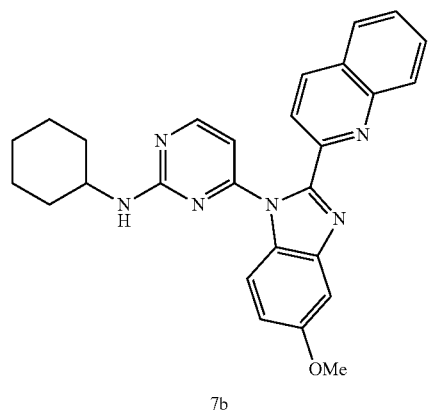

$^1$H NMR (400 MHz, CD₃OD) δ 8.44 (t, J=8.7 Hz, 1H), 8.37 (t, J=5.5 Hz, 1H), 8.05 (s, 1H), 7.98-7.92 (m, 1H), 7.71 (dd, J=9.9, 5.1 Hz, 2H), 7.68-7.54 (m, 2H), (d, J=2.1 Hz, 1H), 7.00-6.93 (m, 1H), 6.74 (s, 1H), 3.35 (s, 1H), 2.85 (s, 1H), 1.57-1.34 (m, 3H), 1.32-1.09 (m, 3H), 1.07-0.72 (m, 5H).

<Example 1-8> 1-(2-(cyclohexylamino)pyrimidin-4-yl)-2-(2,3-dihydrobenzo[b][1,4]dioxin-6-yl)-1H-benzo[d]imidazole-5-ol (10c)

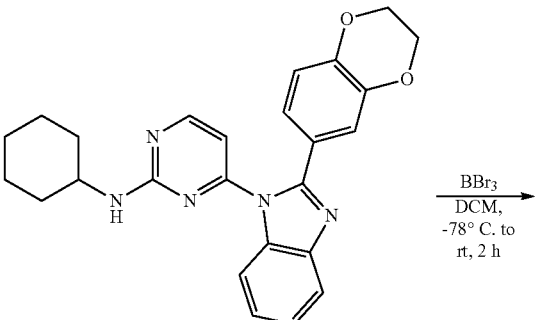

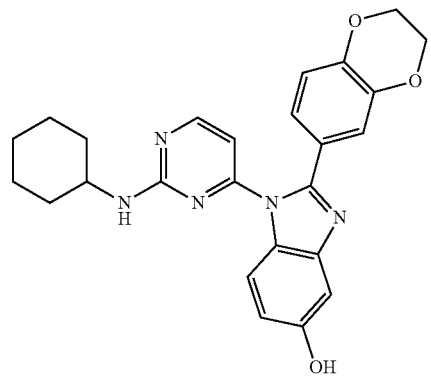

$^1$H NMR (400 MHz, DMSO) δ 9.30 (s, 1H), 8.39 (m, 1H), 7.44 (s, 1H), 7.05 (s, 1H), 6.96 (s, 1H), 6.90 (d, J=8.5 Hz, 1H), 6.78 (dd, J=8.8, 2.3 Hz, 1H), 6.60 (s, 1H), 4.25 (s, 4H), 3.22 (s, 1H), 1.92 (m, 1H), 1.57 (m, 3H), 1.25 (m, 3H), 1.07 (m, 4H), 0.86 (m, 1H).

<Example 1-9> 2-(benzofuran-5-yl)-1-(2-(cyclohexylamine)pyrimidin-4-yl)-1H-benzo[d]imidazole-5-ol (10d)

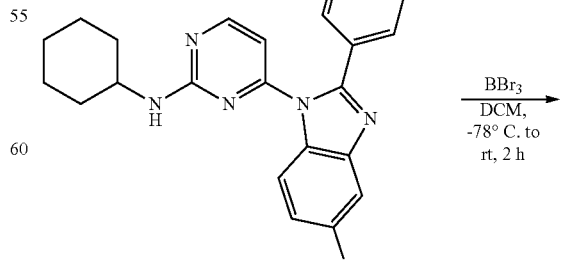

-continued

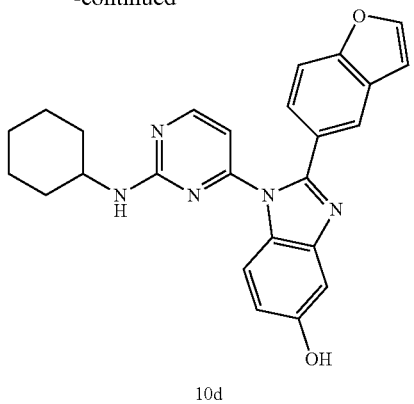

10d $^1$H NMR (400 MHz, CD$_3$OD) δ 8.25 (s, 1H), 7.83 (s, 2H), 7.55 (d, J=8.5 Hz, 2H), 7.42 (d, J=8.3 Hz, 1H), 7.14 (d, J=2.1 Hz, 1H), 6.96-6.85 (m, 2H), 6.53 (s, 1H), 4.16-3.53 (m, 1H), 3.15 (s, 1H), 1.51 (s, 5H), 1.26 (s, 1H), 1.18-0.82 (m, 5H).

<Example 1-10> 1-(2-(cyclohexylamino)pyrimidin-4-yl)-2-(3,4-dichlorophenyl)-1H-benzo[d]imidazole-5-ol (10e)

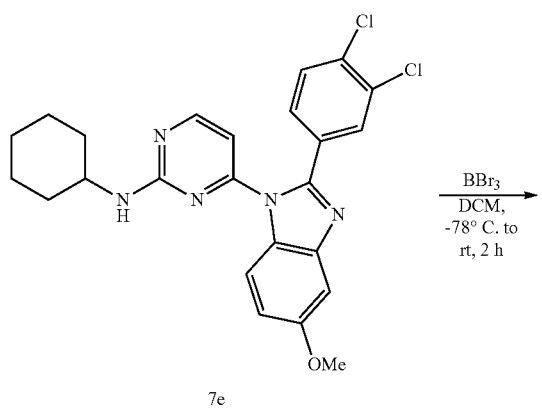

$^1$H NMR (400 MHz, DMSO-d6) δ 9.34 (1H, s), 8.10 (1H, d, J=5.6 Hz), 7.82 (1H, d, J=2.0 Hz), 7.70 (1H, d, J=8.4 Hz), 7.44 (1H, dd, J=8.4 Hz, J=2.4 Hz), 7.19 (1H, d, J=8.8 Hz), 7.09 (1H, d, J=2.4 Hz), 6.83 (1H, dd, J=8.8 Hz, J=2.4 Hz), 6.71 (1H, d, J=7.6 Hz), 6.45 (1H, dd, J=5.6 Hz, J=1.6 Hz), 6.38 (1H, d, J=1.6 Hz), 3.61 (2H, s), 1.83-1.85 (2H, m), 1.66-1.70 (2H, m), 1.55-1.59 (1H, m), 1.23-1.32 (3H, m), 1.10-1.19 (3H, m)

<Example 1-11> 1-(2-(cyclohexylamino)pyrimidin-4-yl)-2-(4-fluoro-3-(trifluoromethyl)phenyl)-1H-benzo[d]imidazole-5-ol (10f)

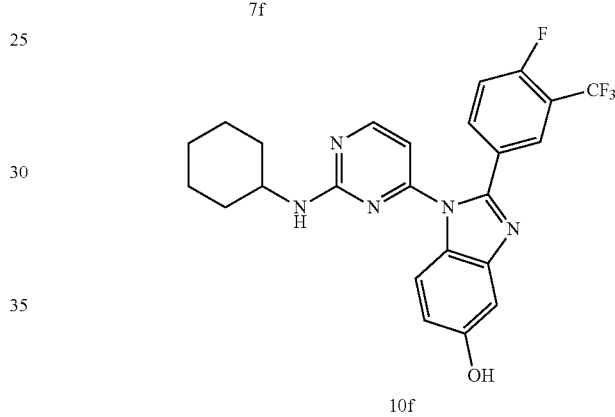

$^1$H NMR (400 MHz, CD$_3$OD) δ 8.40 (dd, J=6.6, 2.0 Hz, 1H), 8.31 (m, 1H), 7.85 (m, 1H), 7.62-7.47 (m, 2H), 7.44 (d, J=8.7 Hz, 1H), 6.97 (d, J=2.0 Hz, 1H), 6.82 (dd, J=8.7, 2.3 Hz, 1H), 3.72 (s, 1H), 1.98-1.93 (m, 1H), 1.76 (m, 2H), 1.70-1.49 (m, 4H), 1.18-1.08 (m, 2H), 0.91-0.82 (m, 3H).

<Example 1-12> (S)-4-(5-methoxy-2-(naphthalene-2-yl)-1H-benzo[d]imidazole-1-yl)-N-(piperidine-3-yl)pyrimidin-2-amine (11a)

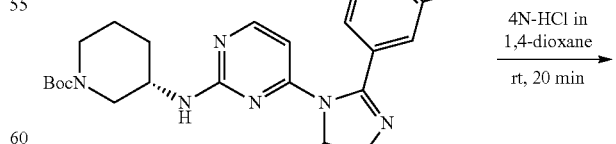

8a

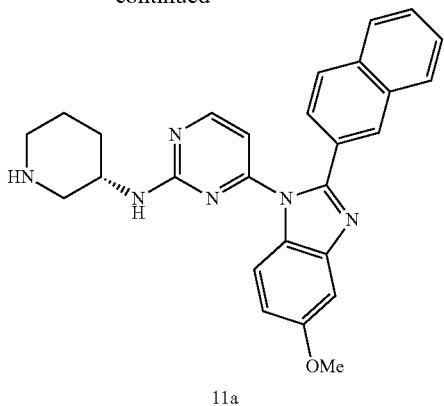

11a

Compound 8a (377 mg, 0.61 mmol) was dissolved in 1,4-dioxane (6.1 ml) and 4 M–HCl (3 ml) containing 1,4-dioxane was treated at room temperature. The reaction mixture was stirred at room temperature for 20 minutes, the mixture was diluted with ether and then stirred until the product separated to a solid. The solid product was filtered off and washed with ether followed by hexane. The crude product was then crystallized to obtain Compound 11a (290 mg, 65%).

$^1$H NMR (400 MHz, DMSO) δ 9.48 (s, 1H), 7.97 (d, J=5.2 Hz, 3H), 7.72 (m, 2H), 7.64-7.53 (m, 3H), 7.35 (s, 1H), 7.00 (s, 1H), 6.64 (s, 1H), 3.85 (s, 3H), 3.37 (s, 1H), 3.17-2.88 (m, 2H), 2.86-2.57 (m, 2H), 1.89 (m, 2H), 1.20 (m, 3H).

In the same manner as in Example 1-12, the compounds of Examples 1-13 to 1-18 were obtained (Compound 11b (47 mg, 61%), 11c (54 mg, 73%), 11d, 11e (71 mg, 83%), 11f (50 mg, 67%), 11g (41 mg, 92%)).

<Example 1-13> (S)-4-(5-methoxy-2-(Quinoline-2-yl)-1H-benzo[d]imidazole-1-yl)-N-(piperidine-3-yl)pyrimidin-2-amine (11b)

$^1$H NMR (400 MHz, CD$_3$OD) δ 8.47 (d, J=7.8 Hz, 2H), 8.08 (s, 1H), 7.97 (d, J=8.0 Hz, 1H), 7.72 (s, 2H), 7.62 (s, 1H), 7.56 (d, J=7.5 Hz, 1H), 7.33 (s, 1H), 7.06 (d, J=8.9 Hz, 1H), 6.76 (s, 1H), 3.87 (s, 3H), 3.84 (s, 1H), 3.62 (s, 1H), 3.19 (s, 1H), 3.06 (m, 1H), 2.88 (m, 1H), 2.74 (m, 1H), 1.81 (m, 2H), 1.63-1.25 (m, 3H).

<Example 1-14> (S)-4-(2-(2,3-dihydrobenzo[b][1,4]dioxin-6-yl)-5-methoxy-1H-benzo[d]imidazole-1-yl)-N-(piperidine-3-yl)pyrimidin-2-amine (11c)

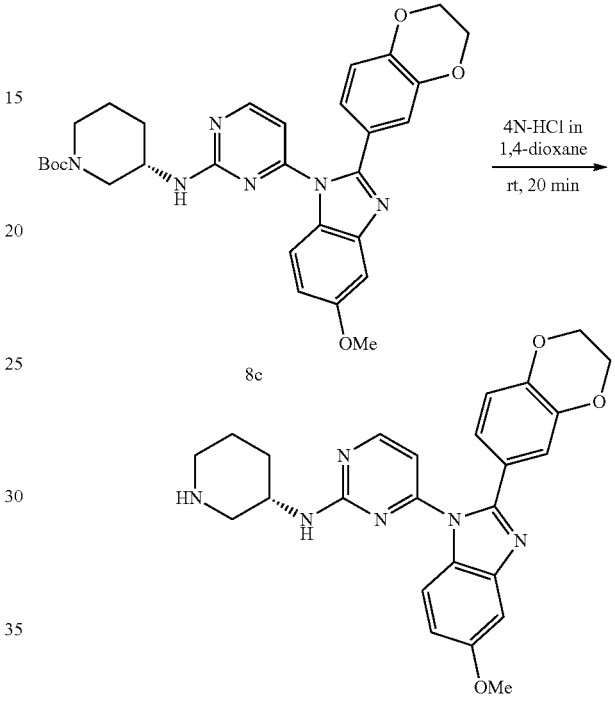

$^1$H NMR (400 MHz, CD$_3$OD) δ 8.32 (s, 1H), 7.52 (s, 1H), 7.22 (s, 1H), 6.99 (s, 1H), 6.90 (d, J=8.5 Hz, 2H), 6.80 (d, J=8.5 Hz, 1H), 6.46 (s, 1H), 4.22 (d, J=4.8 Hz, 2H), 4.20 (d, J=4.8 Hz, 2H), 3.99 (s, 1H), 3.81 (s, 3H), 3.57 (s, 1H), 3.24 (m, 1H), 3.03-2.85 (m, 2H), 1.97 (m, 2H), 1.66 (m, 3H), 1.22 (m, 1H).

<Example 1-15> (S)-4-(2-(benzofuran-5-yl)-5-methoxy-H-benz[d]imidazole-1-yl)-N-(piperidine-3-yl)pyrimidin-2-amine (11d)

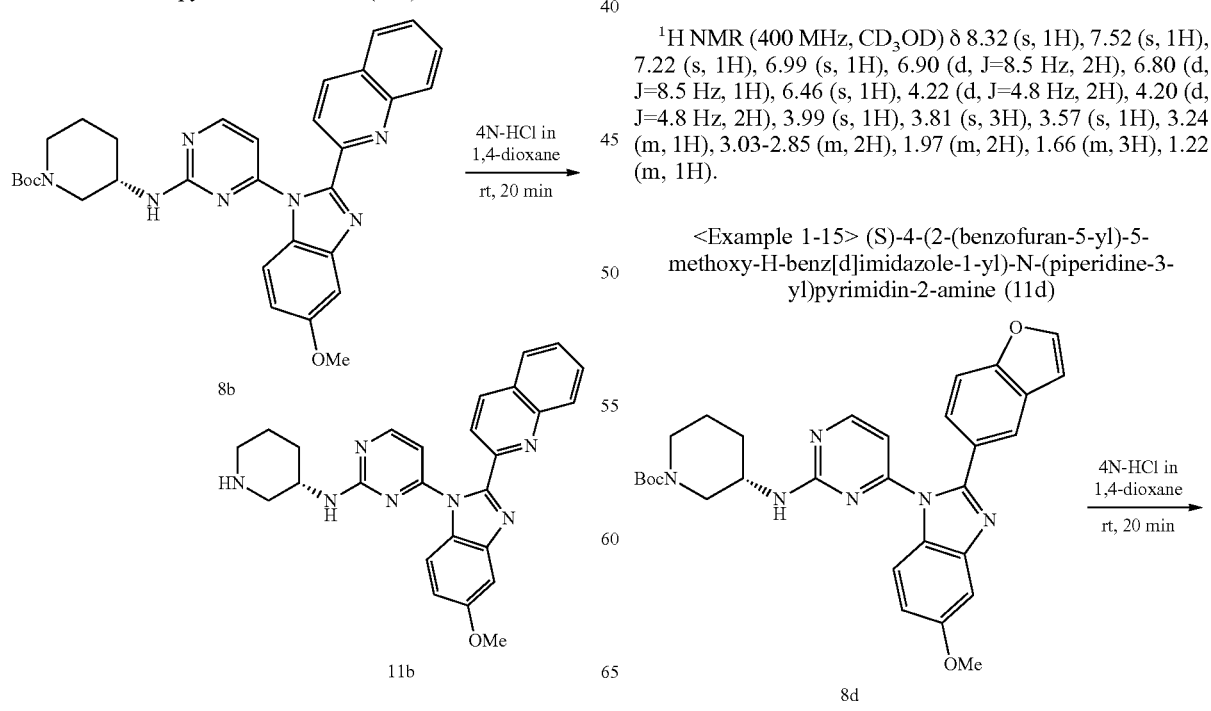

-continued

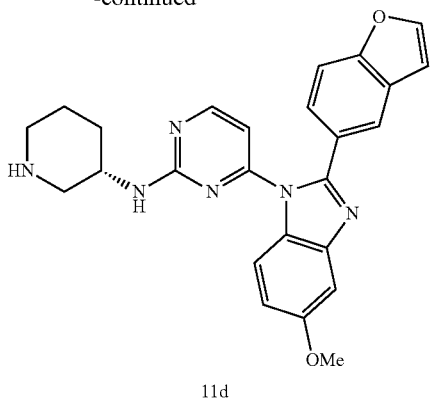

11d

<sup>1</sup>H NMR (400 MHz, MeOD) δ 8.55 (s, 1H), 8.12 (s, 1H), 8.01 (d, J=2.0 Hz, 1H), 7.91 (s, 1H), 7.80 (d, J=8.3 Hz, 1H), 7.64 (d, J=8.3 Hz, 1H), 7.41 (s, 1H), 7.33 (d, J=8.1 Hz, 1H), 7.07 (s, 1H), 6.75 (s, 1H), 4.31 (s, 1H), 3.98 (m, 3H), 3.72-3.51 (m, 1H), 3.28-3.18 (m, 1H), 2.98 (m, 2H), 2.02 (s, 1H), 1.86 (m, 1H), 1.73 (m, 3H), 1.29 (m, 1H).

<Example 1-16> (S)-4-(2-(3,4-dichlorophenyl)-5-methoxy-1H-benzo[d]imidazole-1-yl)-N-(piperidine-3-yl)pyrimidin-2-amine (11e)

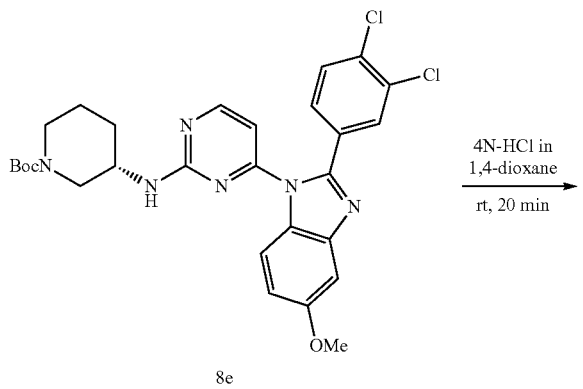

8e

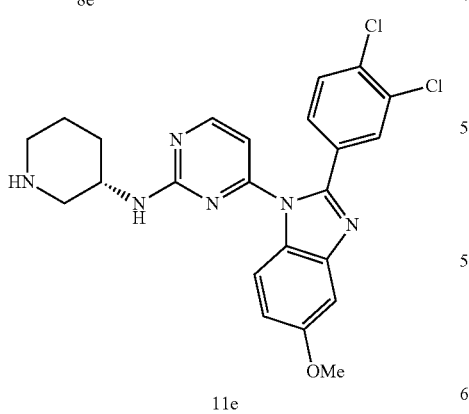

11e

<sup>1</sup>H NMR (400 MHz, CD<sub>3</sub>OD) δ 8.46 (s, 1H), 7.77 (d, J=1.8 Hz, 1H), 7.61 (d, J=8.3 Hz, 2H), 7.45-7.40 (m, 1H), 7.27 (d, J=1.4 Hz, 1H), 7.02 (d, J=8.3 Hz, 1H), 6.69 (s, 1H), 3.86 (s, 3H), 3.35 (s, 1H), 3.15-2.85 (m, 3H), 2.14-1.90 (m, 2H), 1.65 (m, 4H), 1.20 (m, 1H).

<Example 1-17> (S)-4-(2-(4-fluoro-3-(trifluoromethyl)phenyl)-5-methoxy-1H-benzo[d]imidazole-1-yl)-N-(piperidine-3-yl)pyrimidin-2-amine (11f)

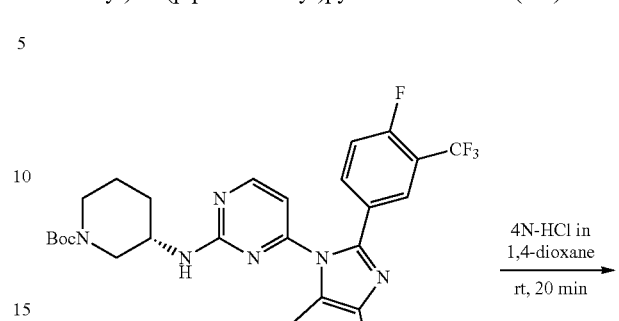

8f

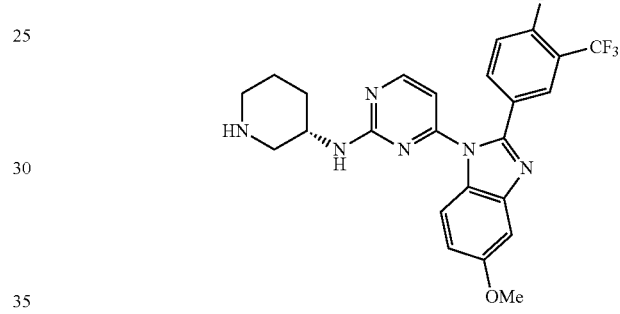

11f

<sup>1</sup>H NMR (400 MHz, CD<sub>3</sub>OD) δ 8.46 (d, J=4.8 Hz, 1H), 7.92 (d, J=5.7 Hz, 1H), 7.85 (s, 1H), 7.63 (s, 1H), 7.47 (m, 1H), 7.25 (d, J=2.2 Hz, 1H), 7.03 (d, J=8.2 Hz, 1H), 6.65 (s, 1H), 3.95 (s, 1H), 3.87 (s, 3H), 3.26 (s, 1H), 3.01-2.84 (m, 2H), 2.19-1.91 (m, 2H), 1.91-1.53 (m, 3H), 1.53-1.22 (m, 1H), 1.21-0.47 (m, 1H).

<Example 1-18> (S)-4-(2-(benzo[d][1,3]dioxole-5-yl)-5-methoxy-1H-benzo[d]imidazole-1-yl)-N-(piperidine-3-yl)pyrimidin-2-amine (11g)

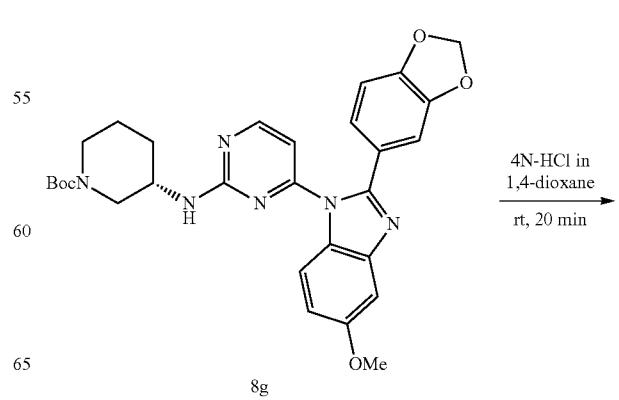

8g

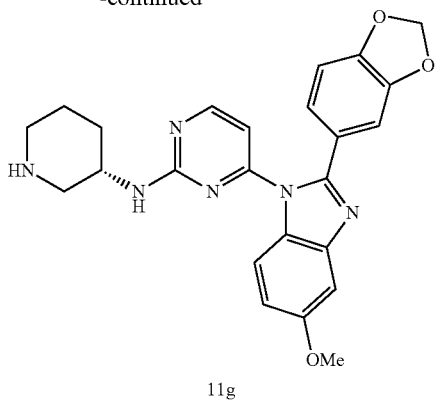

11g

¹H NMR (400 MHz, CD₃OD) δ 8.40 (s, 1H), 7.61 (s, 1H), 7.30 (s, 1H), 7.00 (m, 3H), 6.87 (s, 1H), 6.45 (s, 1H), 6.02 (s, 2H), 4.08 (s, 1H), 3.85 (s, 3H), 3.62 (s, 1H), 3.35 (m, 1H), 2.99 (m, 2H), 2.00 (m, 2H), 1.71 (m, 3H), 1.23 (m, 1H).

<Example 1-19> (S)-cyclopropyl(3-((4-(5-methoxy-2-(naphthalene-2-yl)-1H-benzo[d]imidazole-1-yl)pyrimidin-2-yl)amino)piperidine-1-yl)methanone (12a)

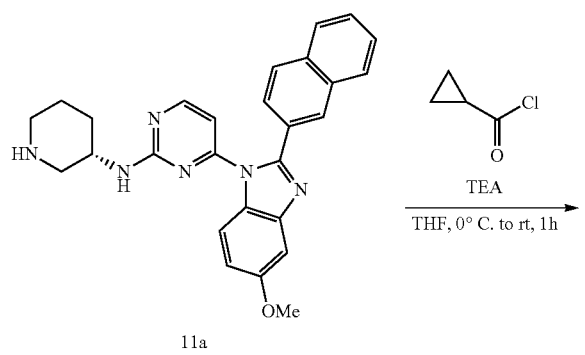

Compound 11a (100 mg, 0.22 mmol) was dissolved in THF (0.55 ml) and cooled to 0° C., then treated with TEA (46 μL). The mixture was added cyclopropanecarbonyl chloride (23 mg) at 0° C., raised to room temperature, and stirred for 1 hour. The reaction mixture was concentrated in vacuum, diluted with methylene chloride and washed with water and saturated aqueous sodium chloride solution. The organic layer was dried over sodium sulfate, filtered, and the filtrate was distilled under reduced pressure, and the residue was purified by column chromatography (silica gel, DCM:MEOH 40:1) to obtain Compound 12a (73 mg, 64%).

¹H NMR (400 MHz, CDCl₃) δ 8.18 (s, 2H), 7.81 (m, 4H), 7.577.47 (m, 3H), 7.32 (s, 1H), 7.01 (dd, J=8.8, 2.2 Hz, 1H), 6.36 (m, 1H), 4.04 (s, 1H), 3.86 (s, 3H), 3.74 (m, 1H), 3.46 (m, 2H), 3.10 (m, 1H), 1.59 (m, 4H), 1.33-1.12 (m, 1H), 1.05-0.70 (m, 4H), 0.44 (s, 1H).

In the same manner as in Example 1-19, the compound of Examples 1-20 to 1-25 was obtained (Compound 12b (41 mg, 79%), 12c (48 mg, 77%), 12d, 12e (60 mg, 78%), 12f (32 mg, 61%), 12g (37 mg, 84%)).

<Example 1-20> (S)-cyclopropyl(3-((4-(5-methoxy-2-(Quinoline-2-yl)-1H-benzo[d]imidazole-1-yl)pyrimidin-2-yl)amino)piperidine-1-yl)methanone (12b)

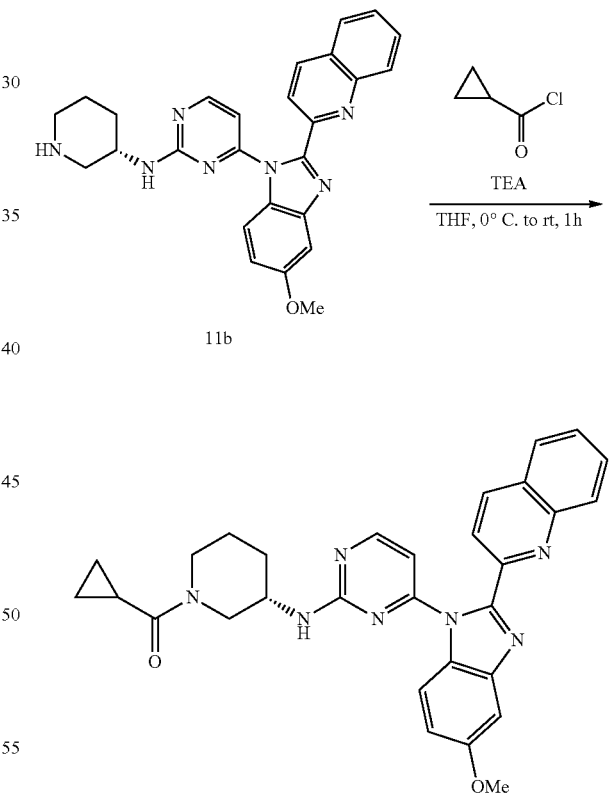

¹H NMR (400 MHz, CD₃OD) δ 8.43 (d, J=8.5 Hz, 1H), 8.42-8.34 (m, 1H), 8.18 (d, J=8.5 Hz, 1H), 7.95 (d, J=7.7 Hz, 1H), 7.69 (dd, J=13.5, 6.1 Hz, 2H), 7.61 (dd, J=12.6, 5.5 Hz, 2H), 7.32 (s, 1H), 7.05 (d, J=8.9 Hz, 1H), 6.77 (s, 1H), 4.18-4.06 (br, 1H), 3.97 (m, 1H), 3.89 (s, 3H), 3.13 (m, 1H), 2.86 (m, 2H), 1.91 (m, 1H), 1.48 (m, 4H), 1.22-1.03 (m, 1H), 0.93-0.48 (m, 4H), 0.15 (m, 1H).

53

<Example 1-21> (S)-cyclopropyl(3-((4-(2-(2,3-dihydrobenzo[b][1,4]dioxin-6-yl)-5-methoxy-1H-benzo[d]imidazole-1-yl)pyrimidin-2-yl)amino)piperidine-1-yl)methanone (12c)

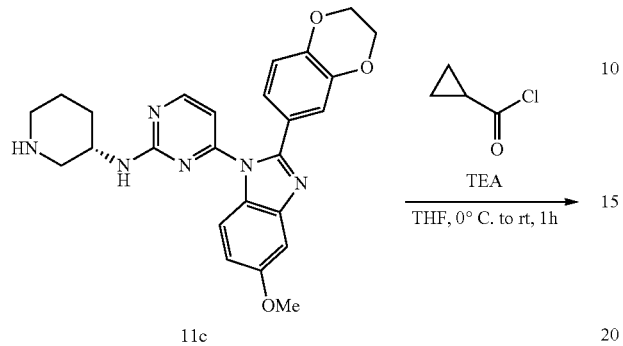

11c

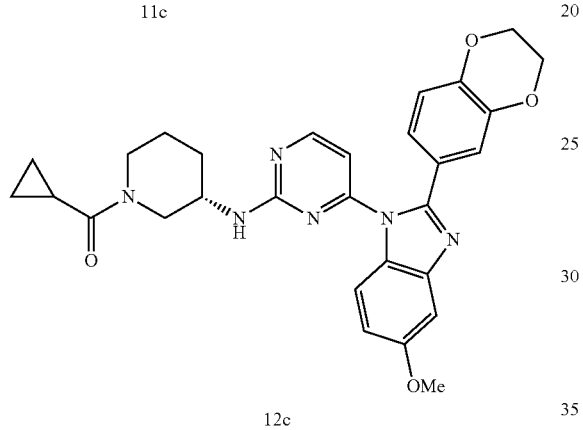

12c $^1$H NMR (400 MHz, CD$_3$OD) δ 8.32 (d, J=33.2 Hz, 1H), 7.70-7.44 (m, 1H), 7.21 (s, 1H), 7.04 (s, 1H), 6.94 (m, 2H), 6.86 (d, J=8.4 Hz, 1H), 6.48 (d, J=33.2 Hz, 1H), 4.25 (d, J=6.6 Hz, 4H), 3.97 (s, 1H), 3.85 (s, 3H), 3.52 (m, 1H), 3.31 (m, 1H), 3.03-2.85 (m, 1H), 1.95 (m, 1H), 1.77-1.69 (m, 2H), 1.59-1.52 (m, 1H), 1.31 (m, 1H), 0.88 (m, 3H), 0.84-0.68 (m, 2H).

<Example 1-22> (S)-(3-(4-(2-(benzofuran-5-yl)-5-methoxy-1H-benz[d]imidazole-1-yl)pyrimidin-2-ylamino)piperidine-1-yl)(cyclopropyl)methanone (12d)

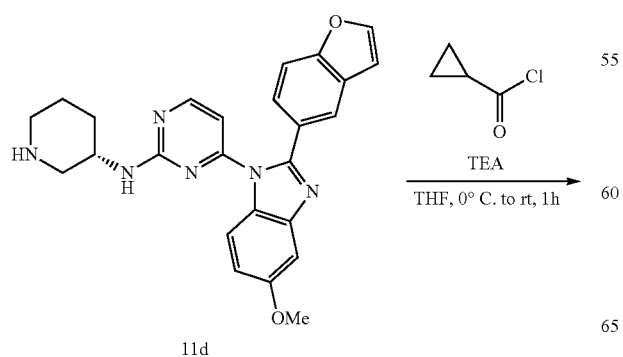

11d

54

-continued

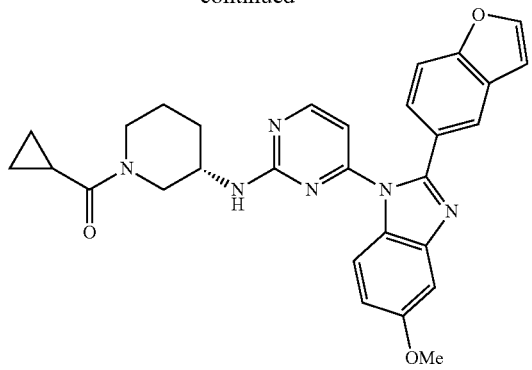

12d $^1$H NMR (400 MHz, MeOD) δ 8.32 (m, 1H), 7.86 (d, J=2.2 Hz, 2H), 7.74 (d, J=8.5 Hz, 1H), 7.58 (d, J=8.5 Hz, 1H), 7.46 (s, 1H), 7.27 (s, 1H), 7.00 (d, J=8.8 Hz, 1H), 6.92 (s, 1H), 6.65 (s, 1H), 4.14 (s, 1H), 3.98 (m, 1H), 2.05-1.91 (m, 2H), 1.59-1.52 (m, 3H), 1.33-1.23 (m, 4H), 0.90-0.85 (m, 5H).

<Example 1-23> (S)-cyclopropyl(3-((4-(2-(3,4-dichlorophenyl)-5-methoxy-1H-benzo[d]imidazole-1-yl)pyrimidin-2-yl)amino)piperidine-1-yl)methanone (12e)

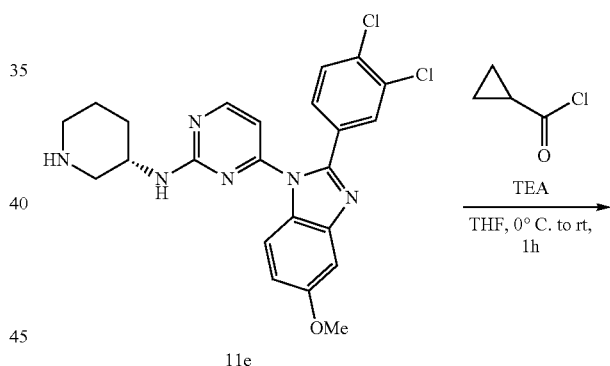

11e

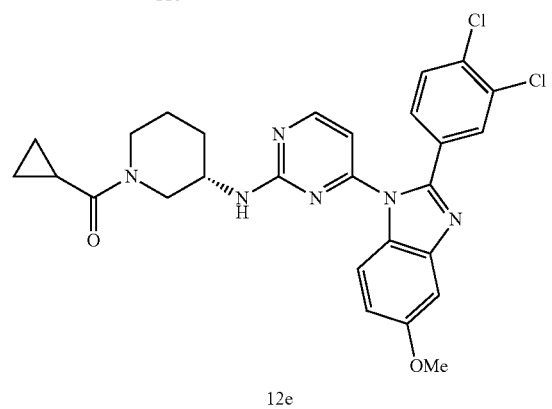

12e $^1$H NMR (400 MHz, CDCl$_3$) δ 8.27 (s, 1H), 7.76 (d, J=22.0 Hz, 1H), 7.60 (d, J=30.5 Hz, 1H), 7.44 (d, J=8.3 Hz, 1H), 7.30 (d, J=2.2 Hz, 2H), 6.97 (s, 1H), 6.47-6.16 (m, 1H), 4.01 (s, 1H), 3.86 (s, 3H), 3.46 (m, 1H), 3.18 (m, 1H), 1.74

(m, 2H), 1.61-1.52 (m, 2H), 1.52-1.44 (m, 1H), 1.40 (m, 1H), 1.23 (m, 1H), 0.98-0.92 (m, 1H), 0.89-0.71 (m, 4H).

<Example 1-24> (S)-cyclopropyl(3-((4-(2-(4-fluoro-3-(trifluoro메닐)phenyl)-5-methoxy-1H-benzo[d]imidazole-1-yl)pyrimidin-2-yl)amino)piperidine-1-yl)methanone (12f)

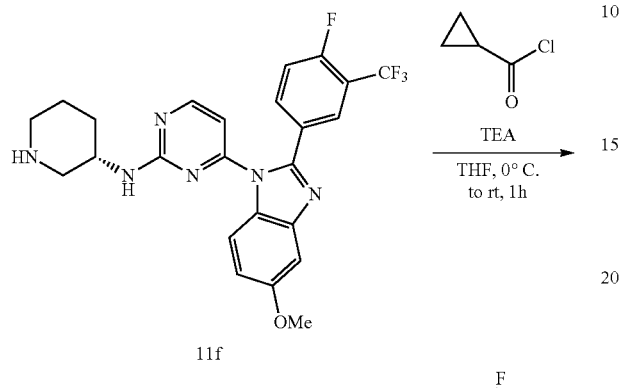

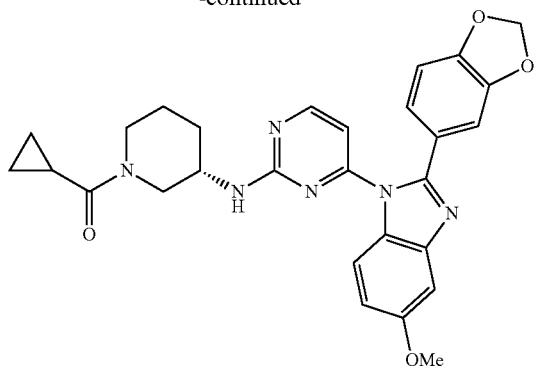

¹H NMR (400 MHz, CDCl₃) δ 8.22 (s, 1H), 7.63 (d, J=32.3 Hz, 1H), 7.33 (s, 1H), 7.06 (d, J=24.5 Hz, 2H), 6.95 (d, J=7.2 Hz, 1H), 6.82 (d, J=8.0 Hz, 1H), 6.26 (d, J=32.3 Hz, 1H), 6.01 (s, 2H), 4.15-4.04 (s, 1H), 3.87 (s, 3H), 3.82-3.71 (m, 1H), 3.56-3.26 (m, 2H), 1.89-1.71 (m, 2H), 1.67-1.54 (m, 3H), 1.03-0.96 (m, 3H), 0.88-0.80 (m, 3H).

<Example 1-26> (S)-cyclopropyl(3-((4-(5-hydroxy-2-(naphthalene-2-yl)-1H-benzo[d]imidazole-1-yl)pyrimidin-2-yl)amino)piperidine-1-yl)methanone (13a)

¹H NMR (400 MHz, CD₃OD) δ 8.50-8.39 (m, 1H), 7.95 (s, 1H), 7.81 (s, 1H), 7.65 (m, 1H), 7.44 (m, 1H), 7.27 (s, 1H), 7.02 (d, J=8.6 Hz, 1H), 6.76 (s, 1H), 4.12-4.01 (s, 1H), 3.88 (s, 3H), 3.27-3.14 (m, 1H), 3.07-2.93 (m, 1H), 2.82 (s, 1H), 1.93 (m, 1H), 1.81-1.69 (m, 2H), 1.62-1.51 (m, 2H), 1.30 (m, 1H), 0.88 (m, 3H), 0.81 (m, 2H).

<Example 1-25> (S)-(3-((4-(2-(benzo[d][1,3]dioxole-5-yl)-5-methoxy-1H-benzo[d]imidazole-1-yl)pyrimidin-2-yl)amino)piperidine-1-yl)(cyclopropyl)methanone (12g)

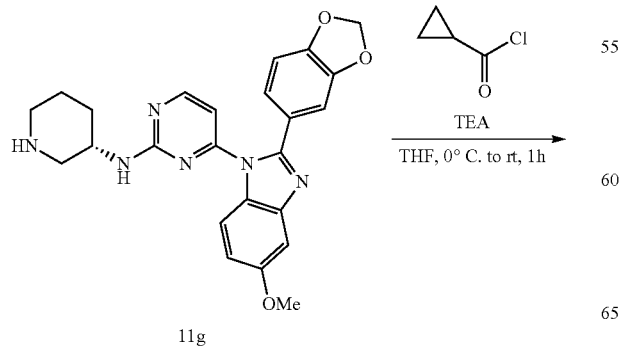

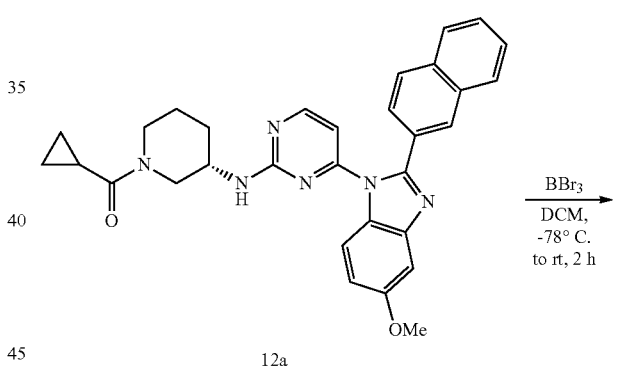

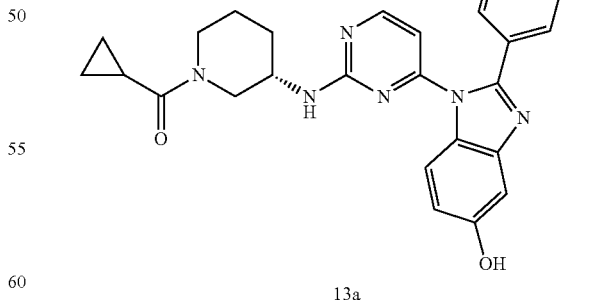

Compound 12a (66 mg, 0.127 mmol) was dissolved in methylene chloride (1.3 ml), BBr₃ (60 al) was added at −78° C. and stirred for about 1 hour, and then stirred at room temperature for about 2 hours. After confirming the completion of the reaction, methanol was added and quenched. The organic solvent was distilled under reduced pressure, extracted with methylene chloride, and washed with a saturated NaHCO₃ aqueous solution. The extracted organic layer was dried over magnesium sulfate anhydrous, filtered, and the filtrate was distilled under reduced pressure and the residue was purified by column chromatography (silica gel, methylene chloride:MeOH=20:1) to obtain Compound 13a (39 mg, 61%).

¹H NMR (400 MHz, DMSO-$d_6$) δ 9.36 (s, 1H), 8.42-8.18 (m, 2H), 7.96-7.94 (m, 3H), 7.61-7.54 (m, 5H), 7.11 (d, J=2.4 Hz, 1H), 6.84 (d, J=7.6 Hz, 1H), 6.67-6.25 (m, 1H), 4.78 (s, 1H), 4.14-3.84 (m, 2H), 3.17-2.85 (m, 2H), 1.97-1.91 (m, 2H), 1.75 (s, 1H), 1.45-1.14 (m, 4H), 0.85-0.69 (m, 2H).

In the same manner as in Example 1-26, the compounds of Examples 1-27 to 1-32 were obtained (Compound 13b (6 mg, 30%), 13c (22 mg, 52%), 13d, 13e (8 mg, 41%) 13f (14 mg, 50%), 13g).

<Example 1-27> (S)-cyclopropyl(3-((4-(5-hydroxy-2-(Quinoline-2-yl)-1H-benzo[d]imidazole-1-yl)pyrimidin-2-yl)amino)piperidine-1-yl)methanone (13b)

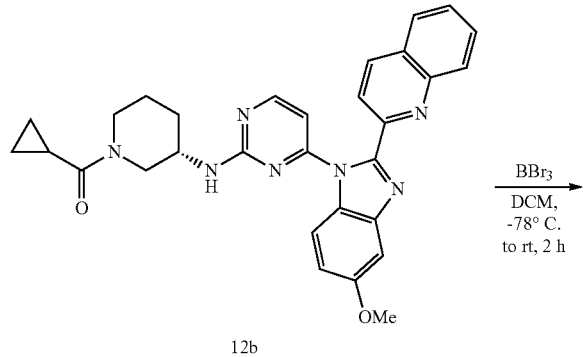

12b

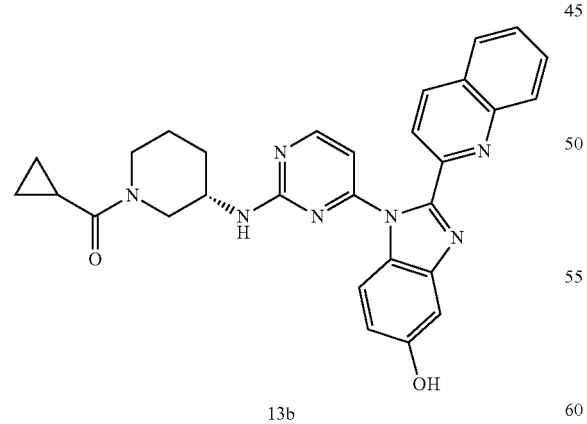

13b

¹H NMR (400 MHz, CD₃OD) δ 8.49-8.41 (m, 2H), 8.19 (d, J=8.5 Hz, 1H), 7.95 (d, J=7.5 Hz, 1H), 7.74-7.67 (m, 2H), 7.61 (m, 2H), 6.95 (dd, J=8.5, 2.1 Hz, 2H), 6.76 (s, 1H), 4.02 (s, 1H), 3.18 (s, 1H), 2.06-1.93 (m, 1H), 1.60 (m, 3H), 1.39 (m, 4H), 1.29 (m, 4H), 0.97-0.78 (m, 5H), 0.60 (m, 1H).

<Example 1-28> (S)-cyclopropyl(3-((4-(2-(2,3-dihydrobenzo[b][1,4]dioxin-6-yl)-5-hydroxy-1H-benzo[d]imidazole-1-yl)pyrimidin-2-yl)amino)piperidine-1-yl)methanone (13c)

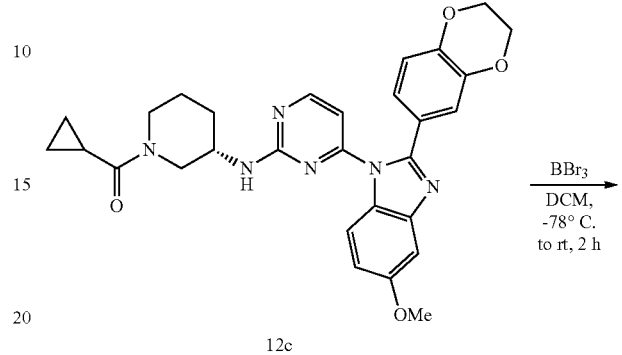

12c

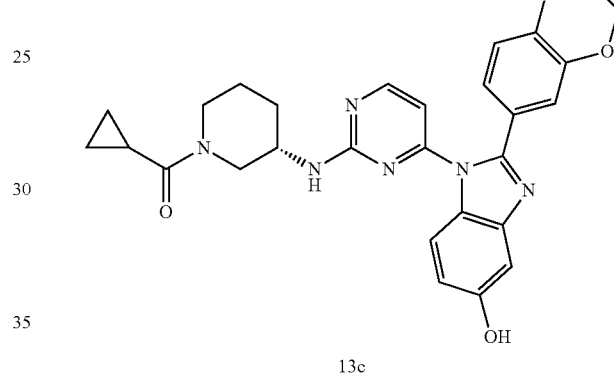

13c

¹H NMR (400 MHz, CD₃OD) δ 8.33 (s, 1H), 7.63-7.41 (m, 1H), 7.09 (s, 1H), 7.03 (s, 1H), 6.97 (d, J=8.4 Hz, 1H), 6.92-6.82 (m, 2H), 6.57 (s, 1H), 4.26 (d, J=6.3 Hz, 4H), 4.07 (s, 1H), 3.49 (s, 1H), 2.97 (m, 1H), 2.02 (m, 2H), 1.79 (m, 2H), 1.61 (m, 4H), 0.95-0.79 (m, 3H), 0.69 (m, 2H).

<Example 1-29> (S)-(3-(4-(2-(benzofuran-5-yl)-5-hydroxy-1H-benz[d]imidazole-1-yl)pyrimidin-2-ylamino)piperidine-1-yl)(cyclopropyl)methanone (13d)

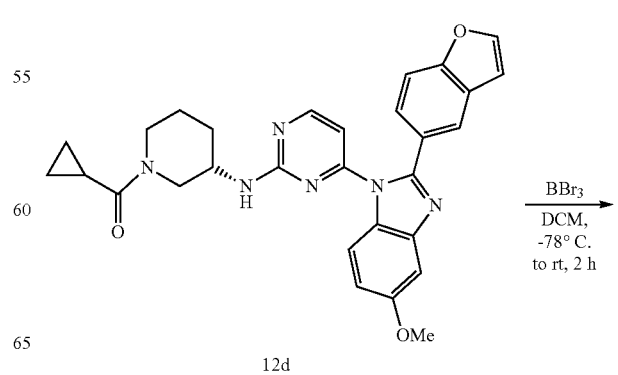

12d

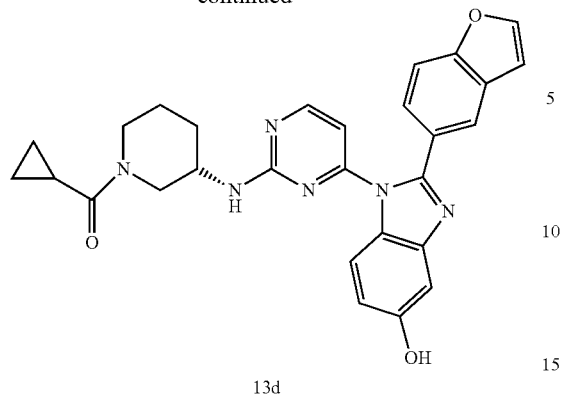

13d

¹H NMR (400 MHz, DMSO) δ 9.33 (s, 1H), 8.33 (d, J=47.4 Hz, 1H), 8.07 (s, 1H), 7.87 (d, J=23.5 Hz, 1H), 7.65 (s, 2H), 7.45 (d, J=18.7 Hz, 1H), 7.08 (d, J=2.2 Hz, 1H), 7.02 (s, 1H), 6.82 (d, J=7.4 Hz, 1H), 4.08 (s, 1H), 2.95 (s, 1H), 1.95 (m, 2H), 1.76 (m, 2H), 1.56 (m, 2H), 1.23 (m, 2H), 0.89-0.66 (m, 4H), 0.63-0.54 (m, 1H), 0.23 (m, 1H).

<Example 1-30> (S)-cyclopropyl(3-((4-(2-(3,4-dichlorophenyl)-5-hydroxy-1H-benzo[d]imidazole-1-yl)pyrimidin-2-yl)amino)piperidine-1-yl)methanone (13e)

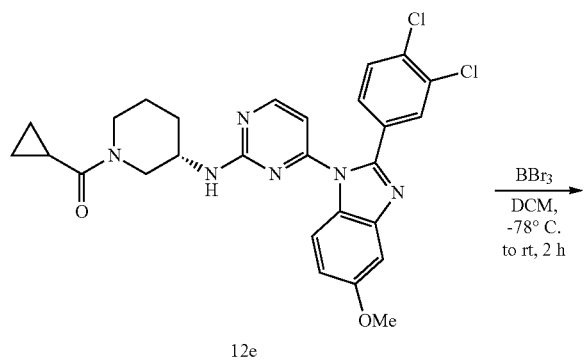

12e

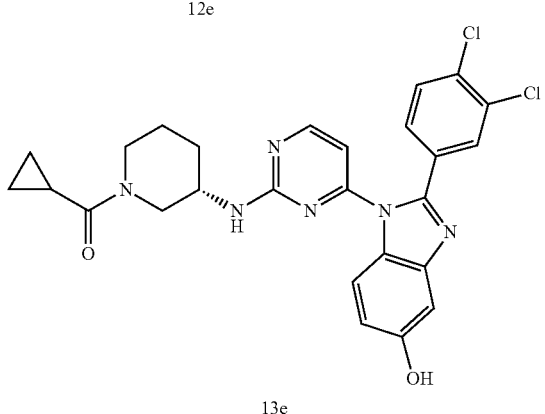

13e

¹H NMR (400 MHz, MeOD) δ 8.43 (d, J=18.2 Hz, 1H), 7.76 (s, 1H), 7.59 (m, 2H), 7.40 (d, J=8.4 Hz, 1H), 7.14 (s, 1H), 6.92 (d, J=8.7 Hz, 1H), 6.78 (s, 1H), 4.20 (s, 1H), 4.08 (m, 1H), 3.15 (m, 1H), 2.92 (s, 1H), 2.06-1.93 (m, 1H), 1.83 (m, 2H), 1.57 (m, 3H), 1.28 (m, 1H), 0.92-0.77 (m, 3H), 0.65 (m, 1H), 0.36 (m, 1H).

<Example 1-31> (S)-cyclopropyl(3-((4-(2-(4-fluoro-3-(trifluoromethyl)phenyl)-5-hydroxy-1H-benzo[d]imidazole-1-yl)pyrimidin-2-yl)amino)piperidine-1-yl)methanone (13f)

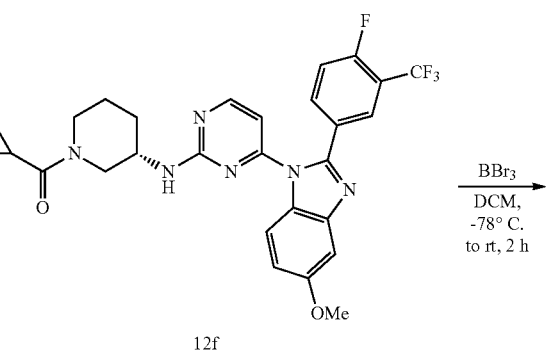

12f

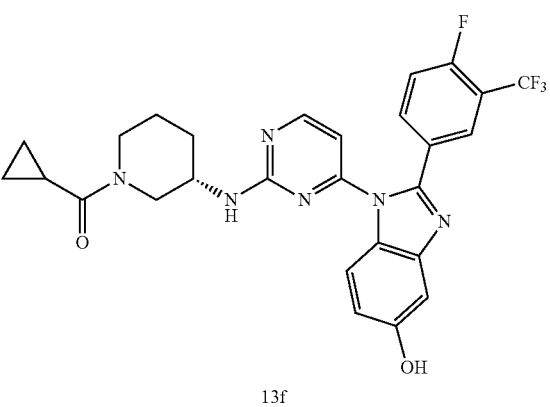

13f

¹H NMR (400 MHz, CD₃OD) δ 8.49-8.37 (m, 1H), 7.92 (s, 1H), 7.80 (s, 1H), 7.64-7.49 (m, 1H), 7.45 (d, J=9.5 Hz, 1H), 7.14 (s, 1H), 6.92 (d, J=8.8 Hz, 1H), 6.77 (s, 1H), 4.19 (s, 1H), 2.93-2.72 (m, 1H), 2.05 (m, 1H), 1.91-1.73 (m, 3H), 1.72-1.64 (m, 1H), 1.61-1.50 (m, 2H), 0.94-0.85 (m, 2H), 0.84-0.78 (m, 2H), 0.74 (m, 1H), 0.62 (m, 1H).

<Example 1-32> (S)-(3-(4-(2-(benzo[d][1,3]dioxole-5-yl)-5-hydroxy-1H-benz[d]imidazole-1-yl)pyrimidin-2-ylamino)piperidine-1-yl)(cyclopropyl)methanone (13g)

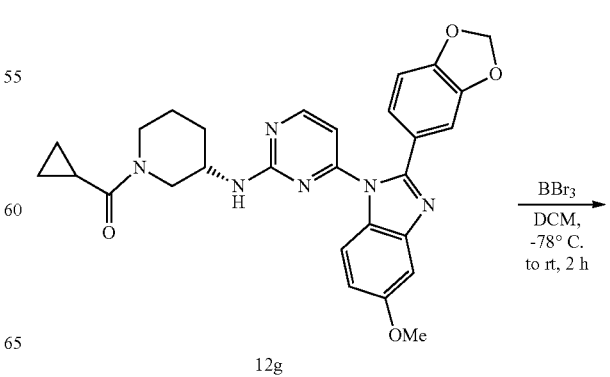

12g

-continued

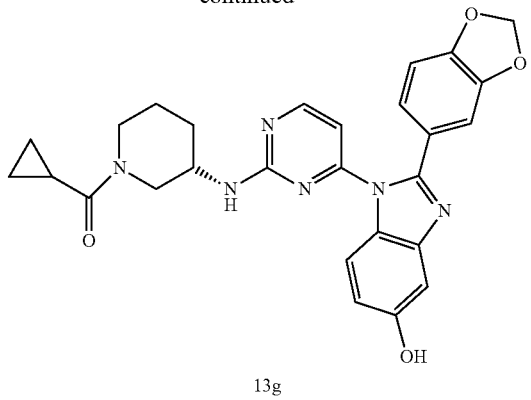

13g

¹H NMR (400 MHz, MeOD) δ 8.41-8.25 (m, 1H), 7.55 (m, 1H), 7.08 (s, 1H), 6.94 (s, 1H), 6.90-6.77 (m, 3H), 6.49 (m, 1H), 4.25 (s, 1H), 4.02 (m, 1H), 3.59-3.36 (m, 1H), 3.08 (m, 2H), 2.06-1.86 (m, 2H), 1.77 (s, 1H), 1.61 (m, 3H), 1.29 (m, 1H), 0.90-0.57 (m, 4H), 0.28 (m, 1H).

II. Synthesis of benzimidazole-6-ol derivatives

<Preparation Example 2-1> N-(5-methoxy-2-nitrophenyl)-2-(methylthio)pyrimidin-4-amine (15)

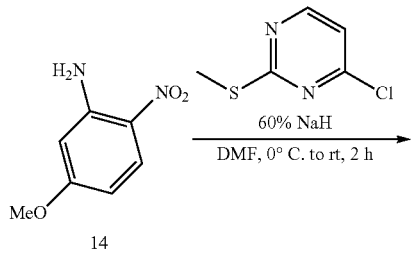
14

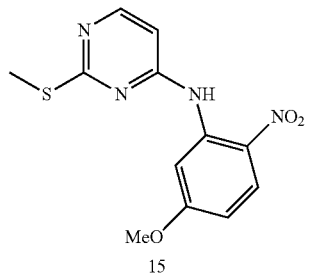
15

4-methoxy 2-nitrobezene amine (Compound 14; 4.6 g, 27.11 mmol) was dissolved in DMF (136 ml) and 60% NaH (1.63 g) was added slowly at 0° C. The mixture was stirred for 1 hour, again, 4-chloro-2-(methylthio)pyrimidine (4355 mg, 17.85 mmol) was added and stirred for about 2 hours. Then, the solvent was poured into iced water to precipitate, and the precipitated reaction was filtered to obtain Compound 15 (6 g, 77%).

¹H NMR (400 MHz, CDCl₃) δ 10.65 (s, 1H), 8.63 (d, J=2.7 Hz, 1H), 8.26 (d, J=5.7 Hz, 1H), 8.22 (d, J=9.5 Hz, 1H), 6.59 (dd, J=9.5, 2.7 Hz, 1H), 6.50 (d, J=5.7 Hz, 1H), 3.93 (s, 3H), 2.57 (s, 3H).

<Preparation Example 2-2> 5-methoxy-N-(2-(methylthio)pyrimidin-4-yl)bezene-1,2-diamine (16)

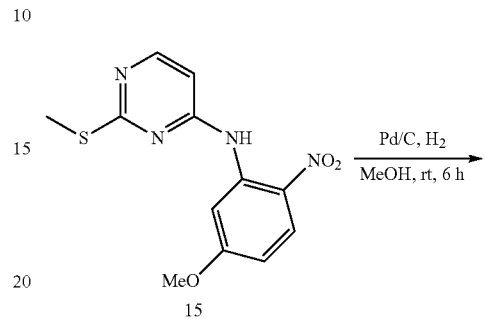
15

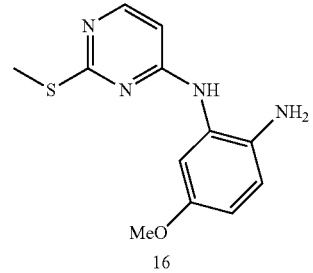
16

Compound 15 (3 g, 10.22 mmol) was dissolved in methanol (68 ml), then 10% Pd/C (448 mg) was added and stirred at room temperature under hydrogen gas for 5 hours. After the reaction was terminated, the mixture was filtered through celite and the filtrate was distilled under reduced pressure. Compound 16 (2.9 g, 99%) was obtained from the residue without any purification.

¹H NMR (400 MHz, CDCl₃) δ 7.99 (d, J=5.9 Hz, 1H), 7.02 (s, 1H), 6.78 (d, J=2.8 Hz, 1H), 6.74 (d, J=8.7 Hz, 1H), 6.68 (dd, J=8.7, 2.8 Hz, 1H), 6.07 (d, J=5.9 Hz, 1H), 3.78 (s, 2H), 3.69 (s, 3H), 2.46 (d, J=5.1 Hz, 3H).

<Preparation Example 2-3> 6-methoxy-1-(2-(methylthio)pyrimidin-4-yl)-2-(naphthalene-2-yl)-1H-benzo[d]imidazole (17a)

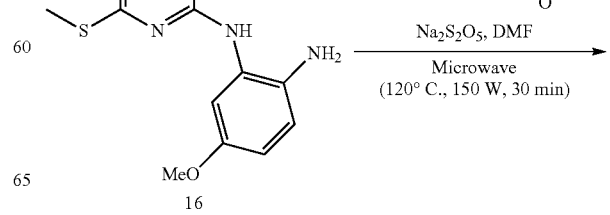
16

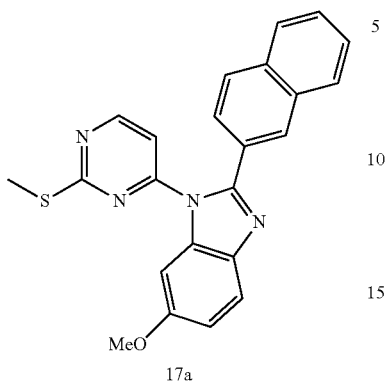

17a

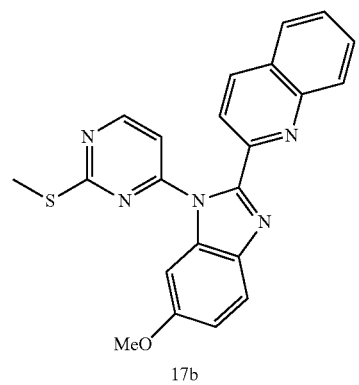

17b

Compound 16 (160 mg, 0.61 mmol), 2-naphthaldehyde (105 mg, 0.67 mmol), and Na₂S₂O₅ (580 mg) were dissolved in DMF (2 ml) and stirred in microwave at 120° C., 150 W, 1 hour 30 minutes. After confirming the completion of the reaction, the solvent was poured into iced water to precipitate. After the precipitated reaction was filtered, the filtrate was distilled under reduced pressure and the residue was purified by column chromatography (silica gel, n-hexane: ethyl acetate=2:1) to obtain Compound 17a (80 mg, 33%).

$^1$H NMR (400 MHz, CDCl$_3$) δ 8.68 (d, J=5.6 Hz, 1H), 8.65 (d, J=5.6 Hz, 1H), 8.22 (d, J=1.2 Hz, 1H), 8.19 (d, J=1.2 Hz, 1H), 7.95-8.00 (m, 6H), 7.80 (d, J=8.8 Hz, 1H), 7.75 (d, J=8.8 Hz, 1H), 7.54-7.64 (m, 6H), 7.41 (d, J=2.4 Hz, 1H), 7.39 (d, J=2.4 Hz, 1H), 7.11 (d, J=5.6 Hz, 1H), 7.03-7.06 (m, 3H), 3.86 (s, 3H), 3.84 (s, 3H), 2.28 (s, 3H), 2.27 (s, 3H).

In the same manner as in Preparation Example 2-3, the compounds of Preparation Examples 2-4 to 2-9 were obtained (Compound 17b (300 mg, 57%), 17c (423 mg, 63%), 17d (262 mg, 45%), 17e (562 mg, 67%), 17f (370 mg, 56%), 17g (414 mg, 64%)).

<Preparation Example 2-4> 2-(6-methoxy-1-(2-(methylthio)pyrimidin-4-yl)-1H-benzo[d]imidazole-2-yl)Quinoline (17b)

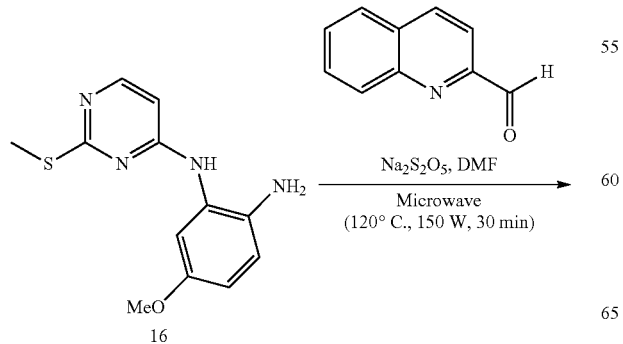

16

$^1$H NMR (400 MHz, DMSO) δ 9.13 (d, J=5.5 Hz, 1H), 7.95 (d, J=2.0 Hz, 1H), 7.76-7.69 (m, 2H), 7.64 (t, J=4.4 Hz, 2H), 7.51-7.47 (m, 1H), 7.06 (dd, J=8.8, 2.4 Hz, 1H), 3.83 (d, J=3.2 Hz, 3H), 3.37 (s, 3H).

<Preparation Example 2-5> 2-(2,3-dihydrobenzo[b][1,4]dioxin-6-yl)-6-methoxy-1-(2-(methylthio)pyrimidin-4-yl)-1H-benzo[d]imidazole (17c)

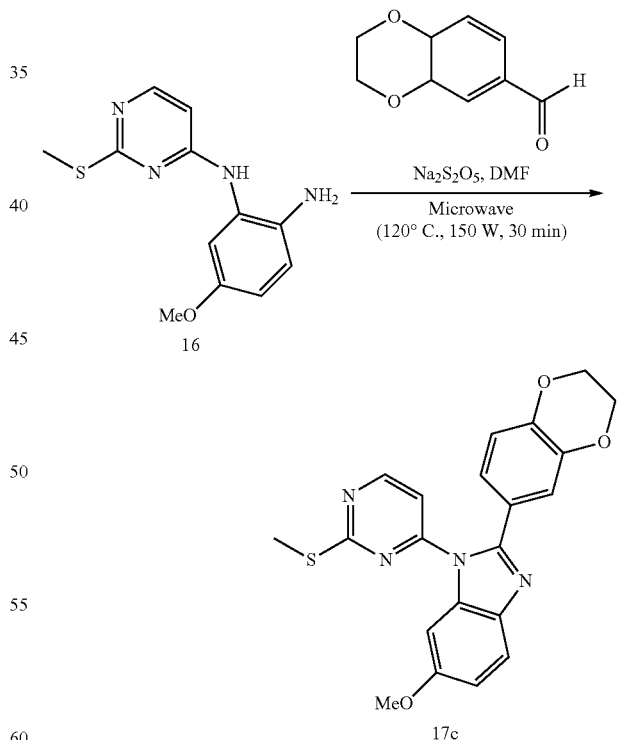

16

17c $^1$H NMR (400 MHz, CDCl$_3$) δ 8.42 (d, J=5.4 Hz, 1H), 7.68 (d, J=8.8 Hz, 1H), 7.42 (d, J=2.4 Hz, 1H), 7.10 (d, J=2.1 Hz, 1H), 6.96 (m, 2H), 6.85 (d, J=8.4 Hz, 1H), 6.54 (d, J=5.4 Hz, 1H), 4.28 (dd, J=3.6, 1.7 Hz, 2H), 4.25 (dd, J=3.6, 1.7 Hz, 2H), 3.84 (s, 3H), 2.56 (s, 3H).

<Preparation Example 2-6> 2-(benzofuran-5-yl)-6-methoxy-1-(2-(methylthio)pyrimidin-4-yl)-1H-benzo[d]imidazole (17d)

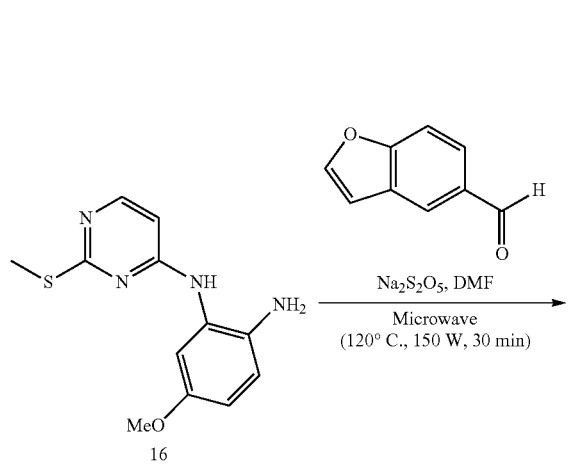

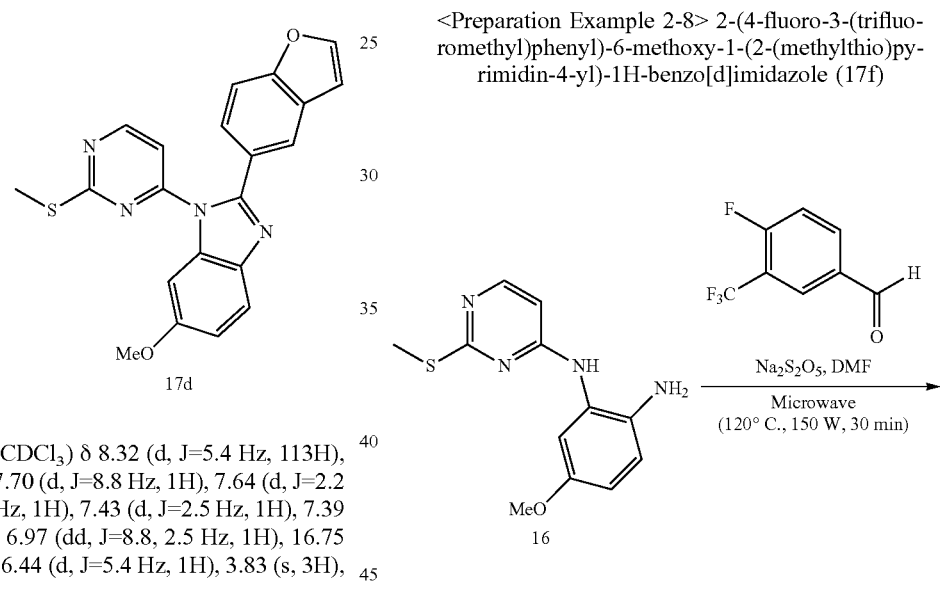

¹H NMR (400 MHz, CDCl₃) δ 8.32 (d, J=5.4 Hz, 113H), 7.81 (d, J=1.8 Hz, 1H), 7.70 (d, J=8.8 Hz, 1H), 7.64 (d, J=2.2 Hz, 1H), 7.48 (d, J=8.6 Hz, 1H), 7.43 (d, J=2.5 Hz, 1H), 7.39 (dd, J=8.6, 1.8 Hz, 1H), 6.97 (dd, J=8.8, 2.5 Hz, 1H), 16.75 (dd, J=2.2, 0.9 Hz, 1H), 6.44 (d, J=5.4 Hz, 1H), 3.83 (s, 3H), 2.49 (s, 3H).

<Preparation Example 2-7> 2-(3,4-dichlorophenyl)-6-methoxy-1-(2-(methylthio)pyrimidin-4-yl)-1H-benzo[d]imidazole (17e)

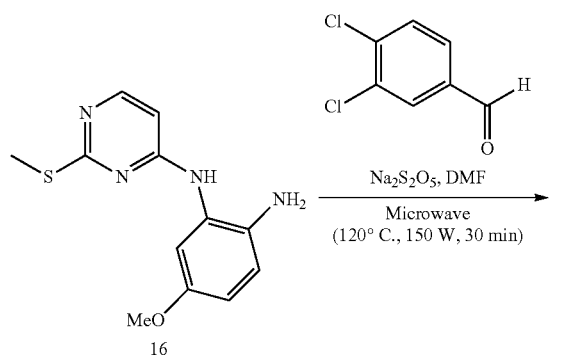

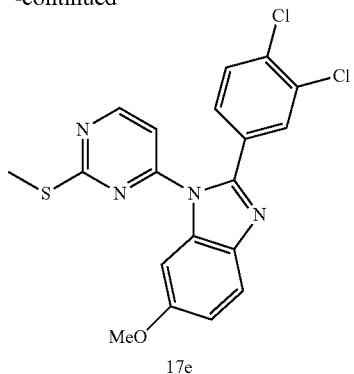

¹H NMR (400 MHz, CDCl₃) δ 8.50 (d, J=5.3 Hz, 1H), 7.77 (d, J=2.0 Hz, 1H), 7.70 (d, J=8.8 Hz, 1H), 7.42 (d, J=8.3 Hz, 1H), 7.33 (d, J=2.4 Hz, 1H), 7.23 (dd, J=8.3, 2.0 Hz, 1H), 6.99 (dd, J=8.8, 2.4 Hz, 1H), 6.62 (d, J=5.3 Hz, 1H), 3.84 (s, 3H), 2.49 (s, 3H).

<Preparation Example 2-8> 2-(4-fluoro-3-(trifluoromethyl)phenyl)-6-methoxy-1-(2-(methylthio)pyrimidin-4-yl)-1H-benzo[d]imidazole (17f)

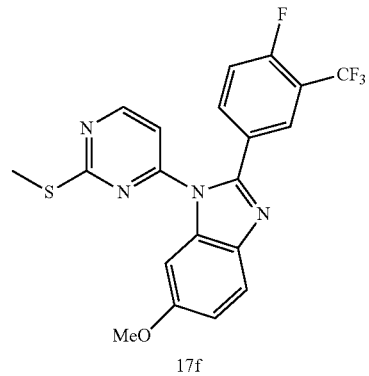

¹H NMR (400 MHz, CDCl₃) δ 8.43 (d, J=5.3 Hz, 1H), 7.86 (dd, J=6.6, 1.9 Hz, 1H), 7.60 (d, J=8.8 Hz, 1H), 7.47 (m, 1H), 7.19 (d, J=2.4 Hz, 1H), 7.10 (m, 1H), 6.90 (dd, J=8.8, 2.4 Hz, 1H), 6.59 (d, J=5.3 Hz, 1H), 3.75 (s, 3H), 2.33 (s, 3H).

<Preparation Example 2-9> 2-(benzo[d][1,3]dioxole-5-yl)-6-methoxy-1-(2-(methylthio)pyrimidin-4-yl)-1H-benzo[d]imidazole (17g)

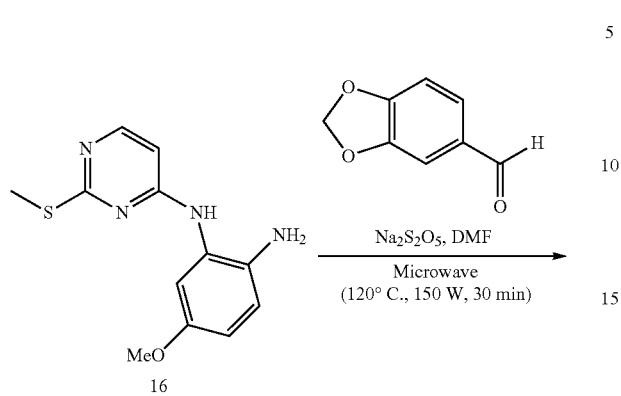

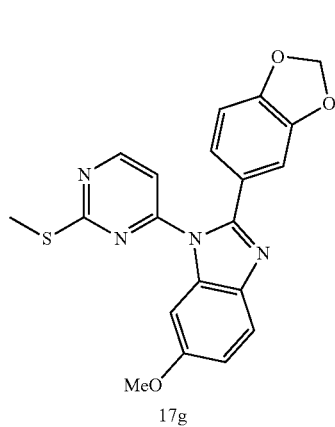

$^1$H NMR (400 MHz, CDCl$_3$) δ 8.45 (d, J=5.4 Hz, 1H), 7.70 (d, J=8.8 Hz, 1H), 7.43 (d, J=2.4 Hz, 1H), 7.03 (d, J=1.5 Hz, 1H), 7.00 (m, 2H), 6.82 (d, J=8.0 Hz, 1H), 6.56 (d, J=5.4 Hz, 1H), 6.03 (s, 2H), 3.86 (s, 3H), 2.58 (s, 3H).

<Preparation Example 2-10> 6-methoxy-1-(2-(methylsulfonyl)pyrimidin-4-yl)-2-(naphtalen-2-yl)-1H-benzo[d]imidazole (18a)

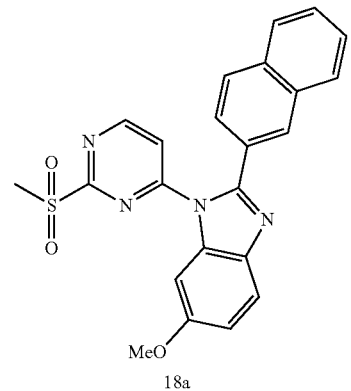

Compound 17a (193 mg, 0.48 mg) and Potassium peroxomonosulfate (1.5 g) were dissolved in MeOH:H2O=1:1 mixed solvent (2.5 ml) and stirred at room temperature for 1 hour. After confirming the reaction, methanol was distilled off under reduced pressure. To the distilled mixture was diluted by addition of water and stirred until the product separated to a solid. The solid product was filtered off and washed with water and then the crude product was crystallized to obtain Compound 18a (250 mg, 98%).

$^1$H NMR (400 MHz, CDCl$_3$) δ 9.01 (d, J=5.6 Hz, 1H), 8.26 (d, J=1.6 Hz, 1H), 8.01 (d, J=8.4 Hz, 1H), 7.77 (d, J=8.4 Hz, 1H), 7.73 (d, J=2.4 Hz, 1H), 7.577.65 (m, 3H), 7.47 (d, J=5.6 Hz, 1H), 7.08 (dd, J=8.4 Hz, J=2.4 Hz, 1H), 3.85 (s, 3H), 3.30 (s, 3H).

In the same manner as in Preparation Example 2-10, the compounds of Preparation Examples 2-12 to 2-16 were obtained (Compound 18b (283 mg, 98%), 18c (432 mg, 98%), 18d (153 mg, 95%), 18e (526 mg, 98%), 18f (343 mg, 96%), 18g (404 mg, 95%)).

<Preparation Example 2-11> 2-(6-methoxy-1-(2-(methylsulfonyl)pyrimidin-4-yl)-1H-benzo[d]imidazole-2-yl)quinolone (18b)

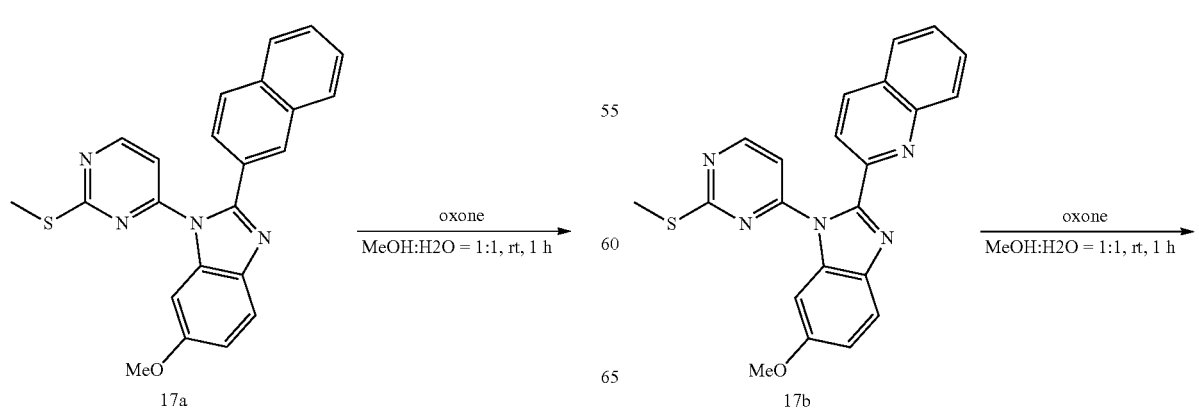

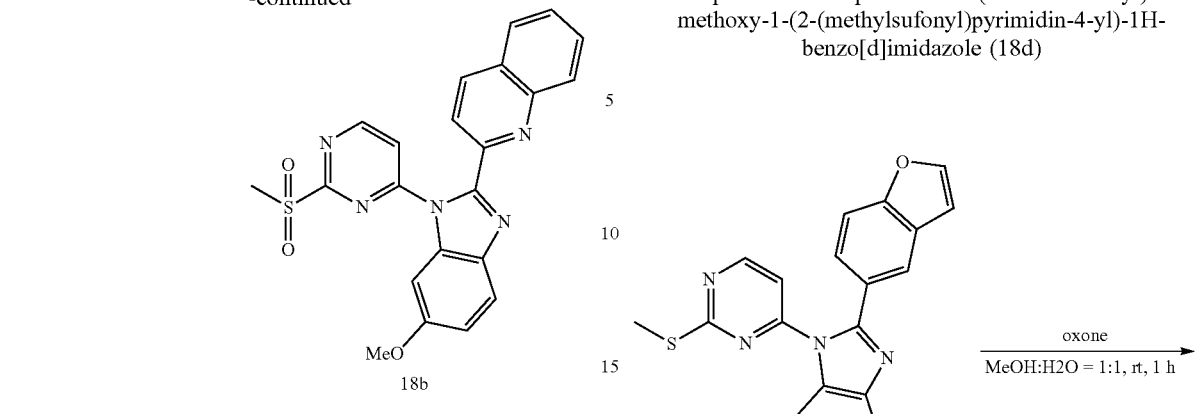

¹H NMR (400 MHz, DMSO) δ 9.17 (d, J=5.3 Hz, 2H), 8.57-8.53 (m, 2H), 8.37 (t, J=7.6 Hz, 2H), 8.02 (d, J=8.0 Hz, 2H), 7.87 (d, J=5.3 Hz, 1H), 7.81 (d, J=8.9 Hz, 2H), 7.71 (t, J=7.6 Hz, 2H), 7.62 (t, J=7.4 Hz, 2H), 7.37-7.26 (m, 4H), 7.09-7.04 (m, 2H), 3.80 (s, 6H), 2.73 (s, 2H).

<Preparation Example 2-12> 2-(2,3-dihydrobenzo[b][1,4]dioxin-6-yl)-6-methoxy-1-(2-(methylsulfonyl)pyrimidin-4-yl)-1H-benzo[d]imidazole (18c)

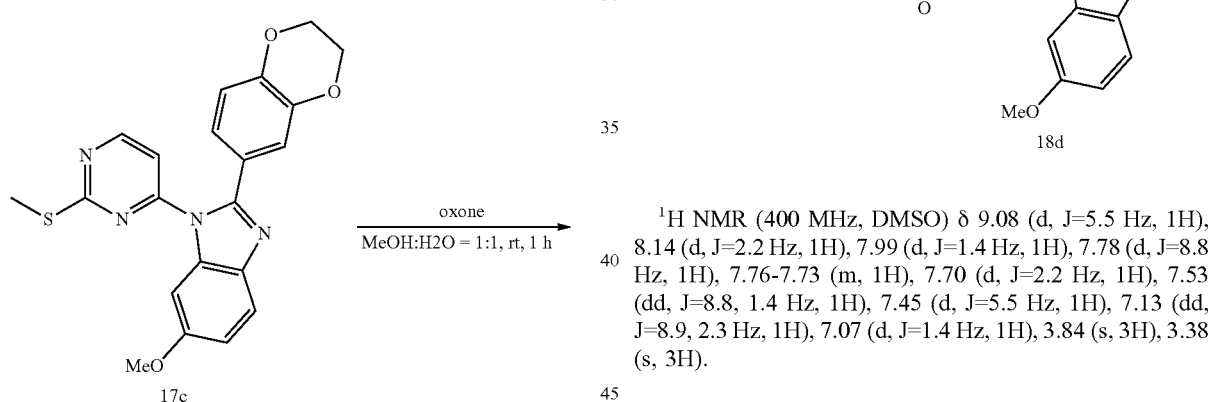

¹H NMR (400 MHz, DMSO) δ 9.17 (d, J=5.3 Hz, 1H), 7.82 (d, J=9.0 Hz, 1H), 7.60 (d, J=2.0 Hz, 1H), 7.57 (d, J=5.3 Hz, 1H), 7.20 (s, 1H), 7.17 (dd, J=9.0, 2.0 Hz, 1H), 7.02 (d, J=1.6 Hz, 1H), 6.99 (s, 1H), 4.33 (s, 2H), 4.30 (s, 2H), 3.81 (s, 3H), 2.90 (s, 3H).

<Preparation Example 2-13> 2-(benzofuran-5-yl)-6-methoxy-1-(2-(methylsufonyl)pyrimidin-4-yl)-1H-benzo[d]imidazole (18d)

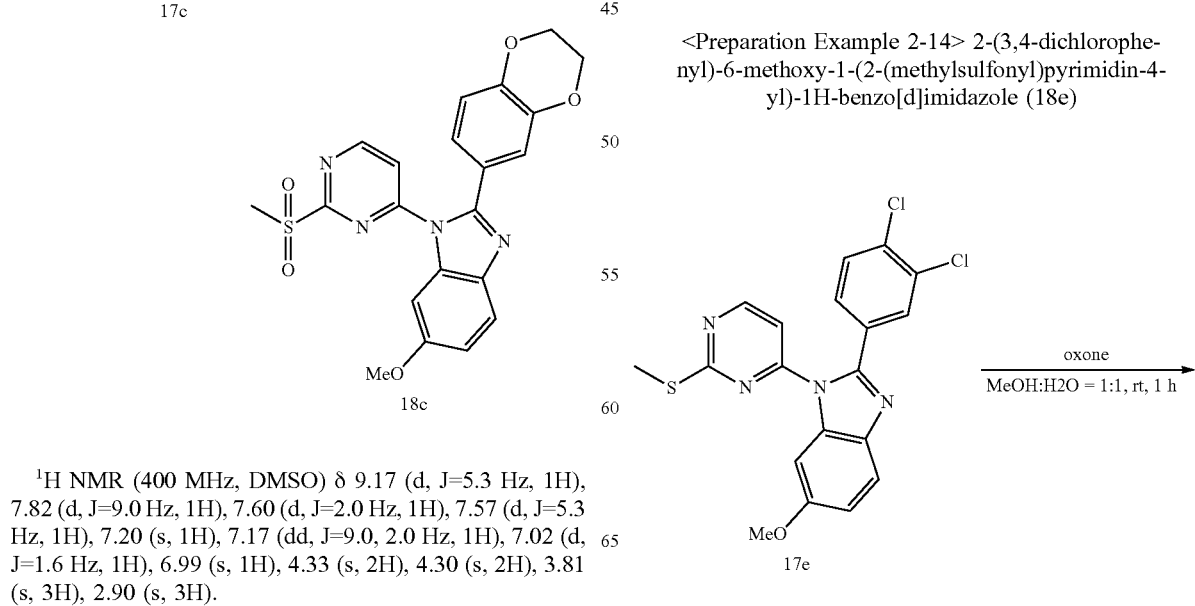

¹H NMR (400 MHz, DMSO) δ 9.08 (d, J=5.5 Hz, 1H), 8.14 (d, J=2.2 Hz, 1H), 7.99 (d, J=1.4 Hz, 1H), 7.78 (d, J=8.8 Hz, 1H), 7.76-7.73 (m, 1H), 7.70 (d, J=2.2 Hz, 1H), 7.53 (dd, J=8.8, 1.4 Hz, 1H), 7.45 (d, J=5.5 Hz, 1H), 7.13 (dd, J=8.9, 2.3 Hz, 1H), 7.07 (d, J=1.4 Hz, 1H), 3.84 (s, 3H), 3.38 (s, 3H).

<Preparation Example 2-14> 2-(3,4-dichlorophenyl)-6-methoxy-1-(2-(methylsulfonyl)pyrimidin-4-yl)-1H-benzo[d]imidazole (18e)

-continued

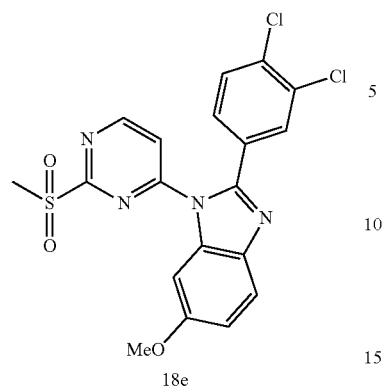
18e

¹H NMR (400 MHz, DMSO) δ 9.13 (d, J=5.5 Hz, 1H), 7.95 (d, J=2.0 Hz, 1H), 7.74 (d, J=8.8 Hz, 1H), 7.70 (d, J=8.4 Hz, 1H), 7.64 (m, 2H), 7.49 (dd, J=8.4, 2.0 Hz, 1H), 7.06 (dd, J=8.8, 2.4 Hz, 1H), 3.83 (s, 3H), 3.37 (s, 3H).

<Preparation Example 2-15> 2-(4-fluoro-3-(trifluoromethyl)phenyl)-6-methoxy-1-(2-(methylsulfonyl)pyrimidin-4-yl)-1H-benzo[d]imidazole (18f)

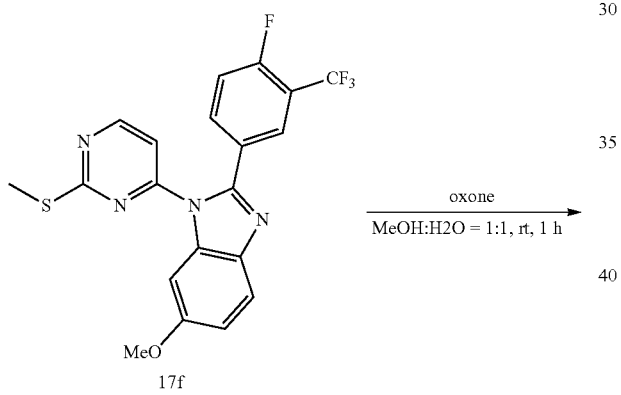
17f → 18f

¹H NMR (400 MHz, DMSO) δ 9.15 (d, J=5.5 Hz, 1H), 8.09-8.06 (m, 1H), 7.89-7.84 (m, 1H), 7.75 (d, J=8.8 Hz, 1H), 7.69 (d, J=5.5 Hz, 1H), 7.63 (d, J=2.4 Hz, 1H), 7.58 (d, J=10.2 Hz, 1H), 7.07 (dd, J=8.8, 2.4 Hz, 1H), 3.83 (s, 3H), 3.35 (s, 3H).

<Preparation Example 2-16> 2-(benzo[d][1,3]dioxole-5-yl)-6-methoxy-1-(2-(methylsulfonyl)pyrimidin-4-yl)-1H-benzo[d]imidazole (18g)

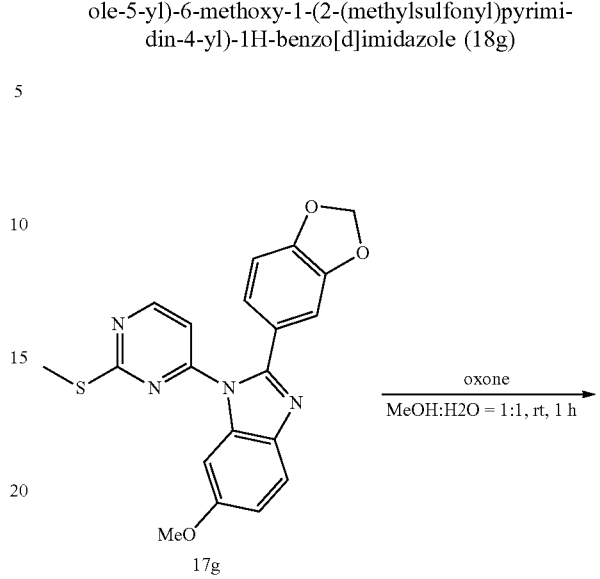
17g → 18g

¹H NMR (400 MHz, DMSO) δ 9.16 (s, 1H), 8.15-8.13 (m, 2H), 7.76 (d, J=7.5 Hz, 1H), 7.69-7.50 (m, 2H), 7.21 (s, 1H), 7.17-7.02 (m, 1H), 6.15 (s, 2H), 3.83 (s, 3H), 3.44 (s, 3H).

<Preparation Example 2-17> 4-(6-methoxy-2-(naphthalene-2-yl)-1H-benzo[d]imidazole-1-yl)-N-(tetrahydro-2H-pyran-4-yl)pyrimidin-2-amine (19a)

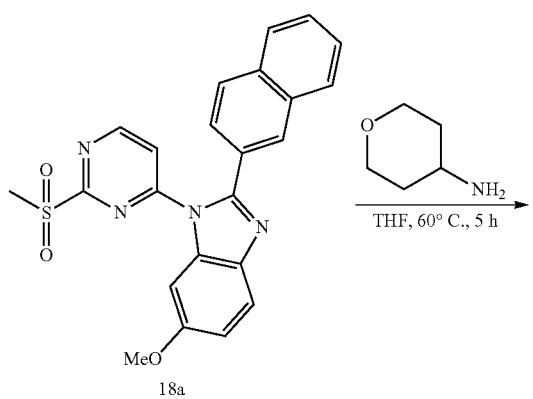
18a

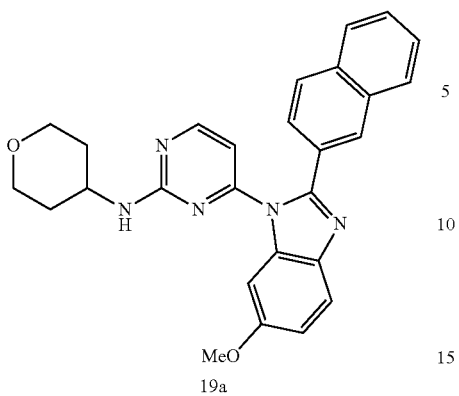

19a

Compound 18a (41 mg, 0.1 mmol) and tetrahydro-2H-pyran-4-amine (20 ul) were dissolved in THF (1 ml) and stirred at 60° C. for 5 hours. After confirming the completion of the reaction, the reaction mixture was cooled to ambient temperature and the filtrate was distilled under reduced pressure, and the residue was purified by column chromatography (silica gel, n-hexane:ethyl acetate=1:1) to obtain Compound 19a (34 mg, 79%).

$^1$H NMR (400 MHz, CDCl$_3$) δ 8.28 (s, 1H), 8.22 (s, 1H), 7.87-7.83 (m, 1H), 7.83-7.76 (m, 3H), 7.54-7.49 (m, 2H), 7.47 (dd, J=8.7, 4.9 Hz, 1H), 7.25 (d, J=7.3 Hz, 1H), 7.02 (dd, J=8.8, 2.4 Hz, 1H), 6.56 (s, 1H), 3.86 (s, 3H), 3.57 (s, 2H), 3.40 (s, 1H), 2.95 (s, 2H), 1.50-1.33 (m, 2H), 1.33-1.07 (m, 3H), 1.03-0.78 (m, 1H).

In the same manner as in Preparation Example 2-17, the compounds of Preparation Examples 2-18 to 2-23 were obtained (Compound 19b (23 mg, 63%), 19c (27 mg, 59%), 19d (36 mg, 70%), 19e (30 mg, 71%), 19f (32 mg, 61%), 19g (26 mg, 65%)).

<Preparation Example 2-18> 4-(6-methoxy-2-(Quinoline-2-yl)-1H-benzo[d]imidazole-1-yl)-N-(tetrahydro-2H-pyran-4-yl)pyrimidin-2-amine (19b)

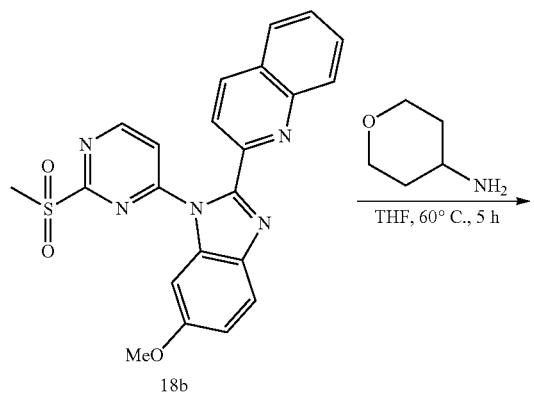

18b

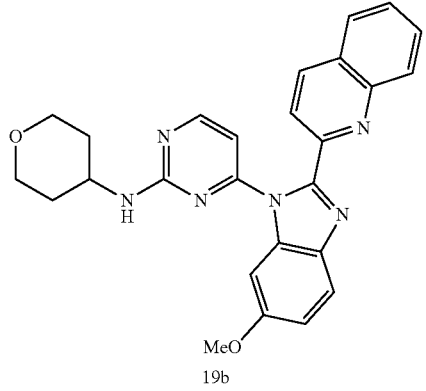

19b $^1$H NMR (400 MHz, CDCl$_3$) δ8.37 (d, J=5.2 Hz, 1H), 8.21 (s, 2H), 7.78 (s, 1H), 7.76 (s, 1H), 7.66 (d, J=8.1 Hz, 1H), 7.63-7.57 (m, 1H), 7.52-7.47 (m, 1H), 7.04 (d, J=2.2 Hz, 1H), 6.99 (dd, J=8.1, 2.2 Hz, 1H), 6.61 (s, 1H), 5.29 (s, 1H), 3.83 (s, 3H), 3.69 (m, 2H), 3.15 (m, 2H), 1.45-1.40 (m, 3H), 0.92 (m, 2H).

<Preparation Example 2-19> 4-(2-(2,3-dihydrobenzo[b][1,4]dioxin-6-yl)-6-methoxy-1H-benzo[d]imidazole-1-yl)-N-(tetrahydro-2H-pyran-4-yl)pyrimidin-2-amine (19c)

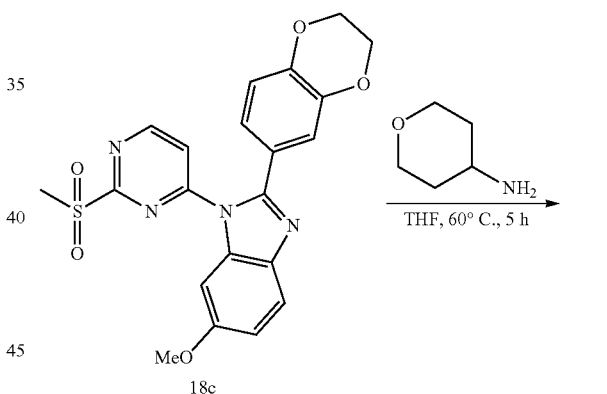

18c

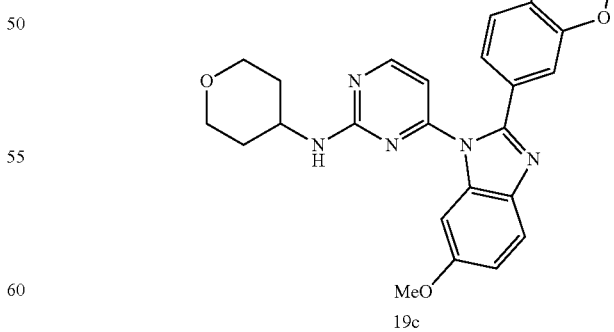

19c $^1$H NMR (400 MHz, CDCl$_3$) δ 8.28 (d, J=4.6 Hz, 1H), 7.71 (d, J=8.8 Hz, 1H), 7.24 (s, 1H), 7.10 (s, 1H), 7.01 (dd, J=8.4, 2.0 Hz, 1H), 6.97 (dd, J=8.8, 2.4 Hz, 1H), 6.84 (d, J=8.4 Hz, 1H), 6.37 (s, 1H), 5.69 (s, 1H), 4.25 (d, J=4.7 Hz,

2H), 4.24 (d, J=4.7 Hz, 2H), 3.94 (m, 2H), 3.84 (s, 3H), 3.42 (m, 2H), 1.83 (m, 1H), 1.52 (m, 2H), 1.26 (m, 2H).

<Preparation Example 2-20> 4-(2-(benzofuran-5-yl)-6-methoxy-1H-benzo[d]imidazole-1-yl)-N-(tetrahydro-2H-pyran-4-yl)pyrimidin-2-amine (19d)

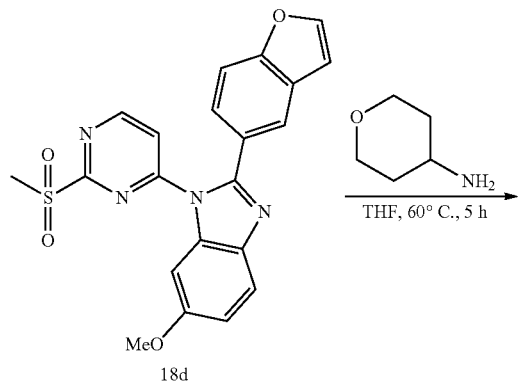

¹H NMR (400 MHz, CDCl₃) δ 8.24 (d, J=4.2 Hz, 1H), 7.89 (d, J=1.3 Hz, 1H), 7.76 (d, J=8.8 Hz, 1H), 7.66 (d, J=2.2 Hz, 1H), 7.48 (d, J=8.6 Hz, 1H), 7.41 (dd, J=8.6, 1.3 Hz, 1H), 7.26 (s, 1H), 7.00 (dd, J=8.8, 2.4 Hz, 1H), 6.79 (dd, J=2.2, 0.8 Hz, 1H), 6.42 (s, 1H), 4.04-3.90 (m, 3H), 3.84 (s, 3H), 3.83-3.73 (m, 1H), 3.59 (m, 1H), 3.50-3.32 (m, 1H), 3.20 (m, 1H), 1.59 (m, 2H), 1.50-1.32 (m, 2H), 1.00-0.80 (m, 1H).

<Preparation Example 2-21> 4-(2-(3,4-dichlorophenyl)-6-methoxy-1H-benzo[d]imidazole-1-yl)-N-(tetrahydro-2H-pyran-4-yl)pyrimidin-2-amine (19e)

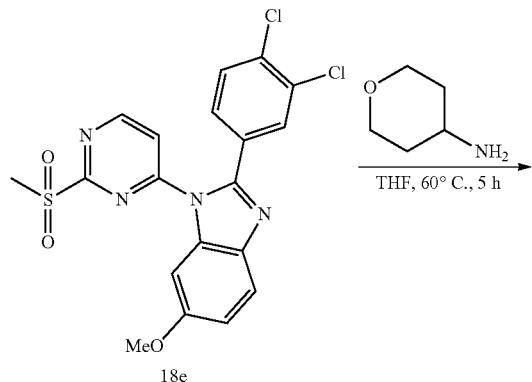

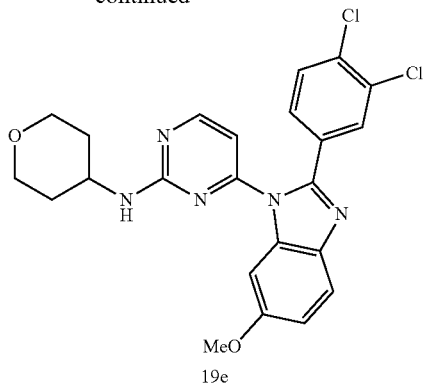

¹H NMR (400 MHz, CDCl₃) δ 8.38 (d, J=4.5 Hz, 1H), 7.77 (d, J=1.7 Hz, 1H), 7.73 (d, J=8.8 Hz, 1H), 7.43 (d, J=8.3 Hz, 1H), 7.28 (dd, J=8.3, 1.7 Hz, 1H), 7.16 (s, 1H), 7.00 (dd, J=8.8, 2.4 Hz, 1H), 6.55 (s, 1H), 5.56 (s, 1H), 3.90 (m, 2H), 3.85 (s, 3H), 3.54 (m 1H), 3.38-3.27 (m, 1H), 1.65 (m 2H), 1.44 (m, 2H), 0.95-0.75 (m, 1H).

<Preparation Example 2-22> 4-(2-(4-fluoro-3-(trifluoromethyl)phenyl)-6-methoxy-1H-benzo[d]imidazole-1-yl)-N-(tetrahydro-2H-pyran-4-yl)pyrimidin-2-amine (19f)

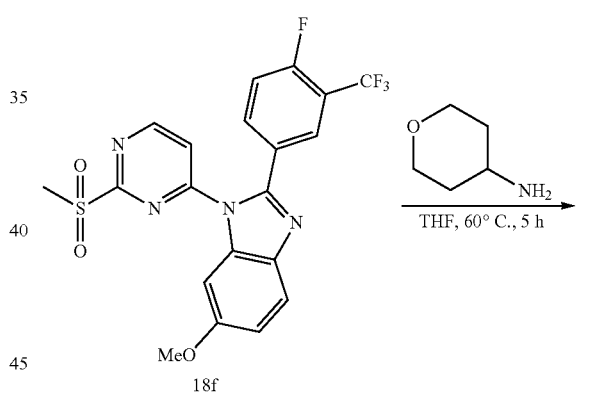

¹H NMR (400 MHz, CDCl₃) δ 8.48 (s, 1H), 8.03 (d, J=6.0 Hz, 1H), 7.84 (d, J=8.7 Hz, 1H), 7.78 (s, 1H), 7.32 (dd, J=15.8, 7.0 Hz, 2H), 7.11 (d, J=8.1 Hz, 1H), 6.63 (s, 1H), 3.98 (s, 1H), 3.95 (s, 3H), 3.71 (s, 1H), 3.41 (s, 2H), 1.77 (s, 1H), 1.58 (s, 2H), 1.33 (s, 2H), 0.94 (d, J=9.6 Hz, 1H).

<Preparation Example 2-23> 4-(2-(benzo[d][1,3]dioxole-5-yl)-6-methoxy-1H-benzo[d]imidazole-1-yl)-N-(tetrahydro-2H-pyran-4-yl)pyrimidin-2-amine (19g)

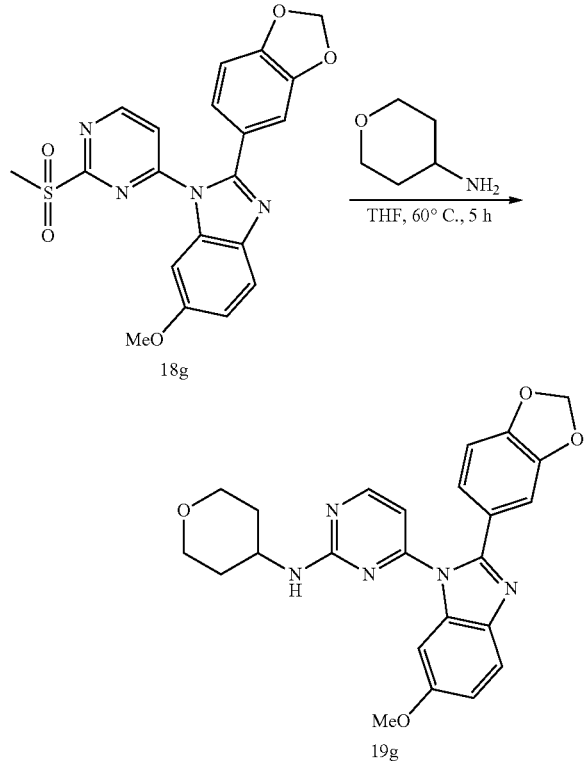

¹H NMR (400 MHz, CDCl₃) δ 8.28 (d, J=5.3 Hz, 1H), 7.75 (d, J=8.8 Hz, 1H), 7.22 (s, 1H), 7.08 (dd, J=8.1, 1.2 Hz, 1H), 7.04 (d, J=1.2 Hz, 1H), 7.00 (dd, J=8.8, 2.4 Hz, 1H), 6.82 (d, J=8.1 Hz, 1H), 6.39 (s, 1H), 6.01 (s, 2H), 3.96 (d, J=8.1 Hz, 2H), 3.84 (s, 3H), 3.49-3.33 (m, 2H), 1.95-1.77 (m, 2H), 1.64-1.47 (m, 3H), 0.95-0.82 (m, 1H).

<Preparation Example 2-24> N-cyclohexyl-4-(6-methoxy-2-(naphthalene-2-yl)-1H-benzo[d]imidazole-1-yl)pyrimidin-2-amine (20a)

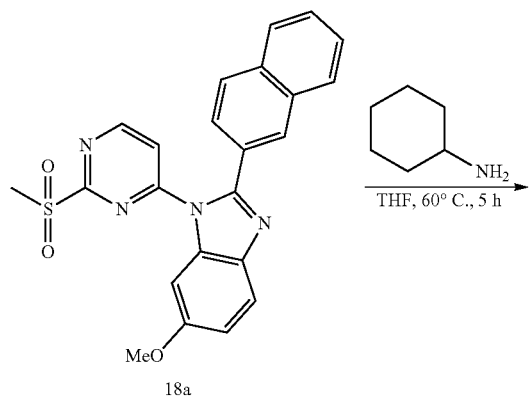

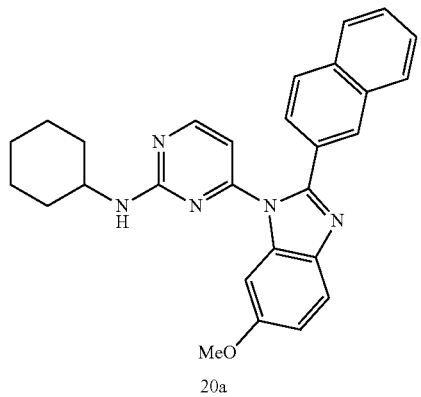

Compound 18a (40 mg, 0.09 mmol) and cyclohexanamine (22 µl) were dissolved in THF (1 ml) and stirred at 60° C. for 5 hours. After completion of the reaction, the reaction mixture was cooled to ambient temperature and the filtrate was distilled under reduced pressure, and the residue was purified by column chromatography (silica gel, n-hexane:ethyl acetate=1:1) to obtain Compound 20a (29 mg, 69%).

¹H NMR (400 MHz, CDCl₃) δ 8.21 (s, 1H), 8.16 (d, J=5.3 Hz, 1H), 7.87-7.76 (m, 4H), 7.55-7.47 (m, 3H), 7.35 (d, J=2.4 Hz, 1H), 7.02 (dd, J=8.8, 2.4 Hz, 1H), 6.29 (s, 1H), 3.87 (s, 3H), 3.51 (s, 1H), 1.72 (m, 2H), 1.53 (m, 3H), 1.24 (m, 1H), 1.09 (m, 4H), 0.92 (m, 1H).

In the same manner as in Preparation Example 2-24, the compounds of Preparation Examples 2-25 to 2-30 were obtained (Compound 20b (31 mg, 98%), 20c (40 mg, 71%), 20d (34 mg, 57%), 20e (20 mg, 50%), 20f (27 mg, 46%), 20g (23 mg, 55%)).

<Preparation Example 2-25> N-cyclohexyl-4-(6-methoxy-2-(Quinoline-2-yl)-1H-benzo[d]imidazole-1-yl)pyrimidin-2-amine (20b)

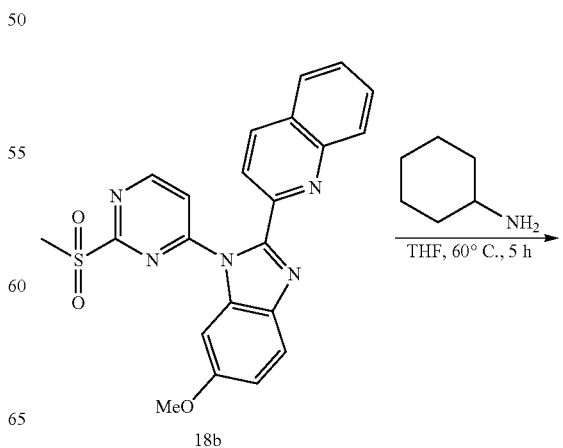

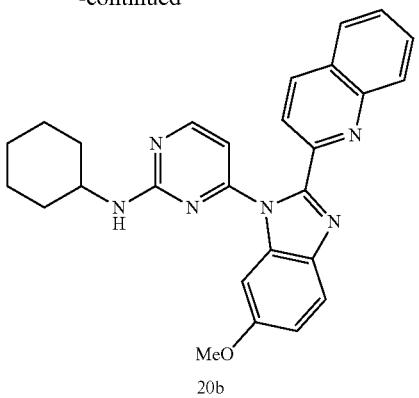

20b

¹H NMR (400 MHz, CDCl₃) δ 8.26 (d, J=4.0 Hz, 1H), 8.17 (s, 2H), 7.73 (dd, J=8.3, 3.7 Hz, 2H), 7.64 (d, J=7.2 Hz, 1H), 7.59-7.52 (m, 1H), 7.49-7.42 (m, 1H), 7.06 (s, 1H), 6.94 (dd, J=8.8, 2.4 Hz, 1H), 6.44 (d, J=4.0 Hz, 1H), 5.28 (s, 1H), 3.79 (s, 3H), 1.56-1.35 (m, 4H), 1.20 (m, 2H), 1.07-0.86 (m, 4H), 0.80 (m, 1H).

<Preparation Example 2-26> N-cyclohexyl-4-(2-(2,3-dihydrobenzo[b][1,4]dioxin-6-yl)-6-methoxy-1H-benzo[d]imidazole-1-yl)pyrimidin-2-amine (20c)

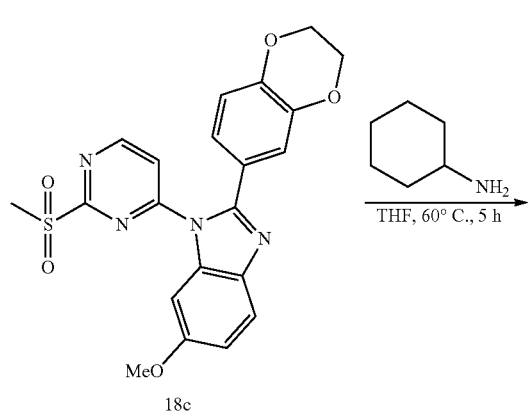

18c

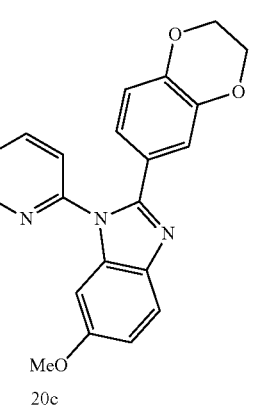

20c

¹H NMR (400 MHz, CDCl₃) δ 8.22 (d, J=5.2 Hz, 1H), 7.69 (d, J=8.8 Hz, 1H), 7.30 (d, J=2.4 Hz, 1H), 7.12 (s, 1H), 7.02 (dd, J=8.4, 2.1 Hz, 1H), 6.96 (dd, J=8.8, 2.4 Hz, 1H), 6.84 (d, J=8.4 Hz, 1H), 6.22 (s, 1H), 5.58 (s, 1H), 4.27 (dd, J=3.6, 1.7 Hz, 2H), 4.24 (dd, J=3.6, 1.7 Hz, 2H), 3.84 (s, 3H), 1.94 (m, 1H), 1.70 (m, 2H), 1.62 (m, 1H), 1.24 (m, 6H), 0.87 (m, 2H).

<Preparation Example 2-27> 4-(2-(benzofuran-5-yl)-6-methoxy-1H-benzo[d]imidazole-1-yl)-N-cyclohexylpyrimidin-2-amine (20d)

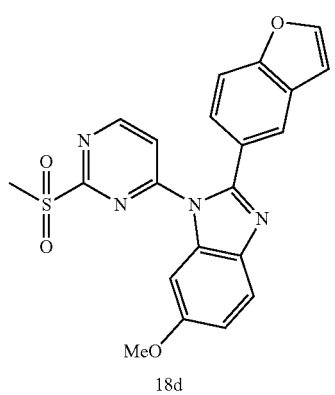
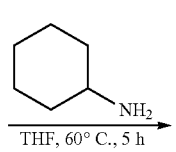

18d

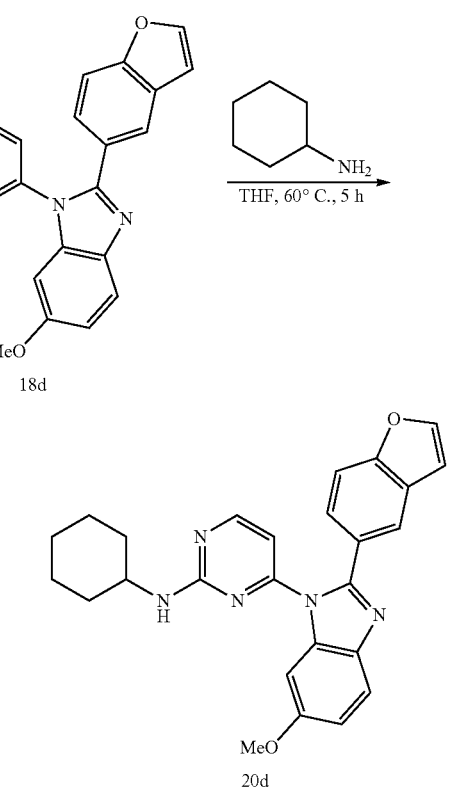

20d

¹H NMR (400 MHz, CDCl₃) δ 8.16 (d, J=5.1 Hz, 1H), 7.87 (s, 1H), 7.74 (d, J=8.8 Hz, 1H), 7.66 (d, J=2.2 Hz, 1H), 7.49 (d, J=8.6 Hz, 1H), 7.44 (dd, J=8.6, 1.6 Hz, 1H), 7.34 (d, J=2.4 Hz, 1H), 7.00 (dd, J=8.8, 2.4 Hz, 1H), 6.78 (dd, J=2.2, 0.6 Hz, 1H), 6.21 (s, 1H), 3.86 (s, 3H), 3.71-3.52 (s, 1H), 1.84 (m, 2H), 1.67 (m, 2H), 1.59 (m, 1H), 1.48-1.28 (m, 1H), 1.17 (m, 4H), 1.02-0.77 (m, 1H).

<Preparation Example 2-28> N-cyclohexyl-4-(2-(3,4-dichlorophenyl)-6-methoxy-1H-benzo[d]imidazole-1-yl)pyrimidin-2-amine (20e)

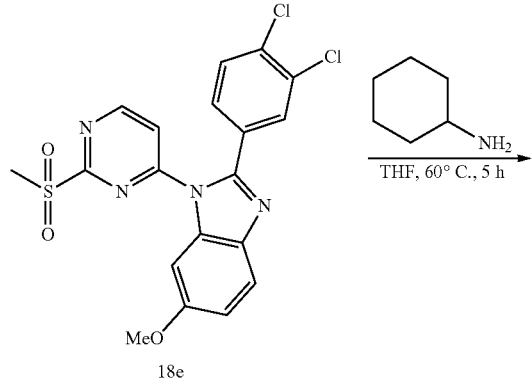

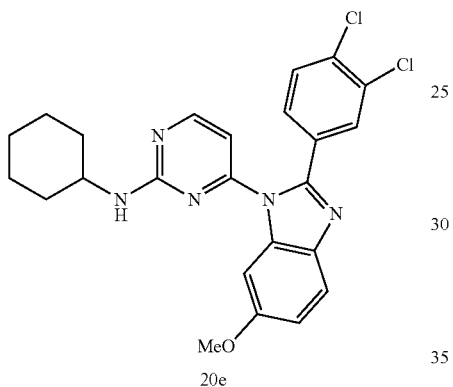

¹H NMR (400 MHz, CDCl₃) δ 8.33 (d, J=5.1 Hz, 1H), 7.79 (s, 1H), 7.73 (d, J=8.8 Hz, 1H), 7.43 (d, J=8.3 Hz, 1H), 7.29 (dd, J=8.3, 2.0 Hz, 1H), 7.21 (d, J=2.4 Hz, 1H), 7.00 (dd, J=8.8, 2.4 Hz, 1H), 6.41 (s, 1H), 5.54 (s, 1H), 3.86 (s, 3H), 1.69 (m, 4H), 1.62 (m, 1H), 1.25 (m, 2H), 1.18 (s, 4H).

<Preparation Example 2-29> N-cyclohexyl-4-(2-(4-fluoro-3-(trifluoromethyl)phenyl)-5-methoxy-1H-benzo[d]imidazole-1-yl)pyrimidin-2-amine (20f)

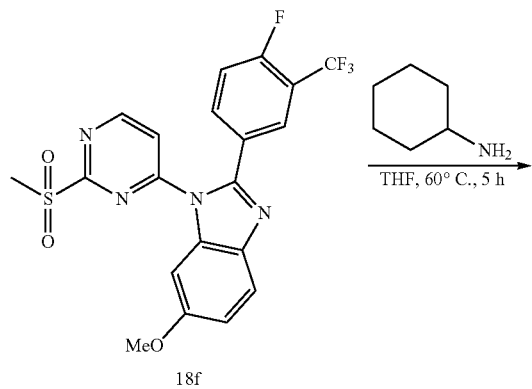

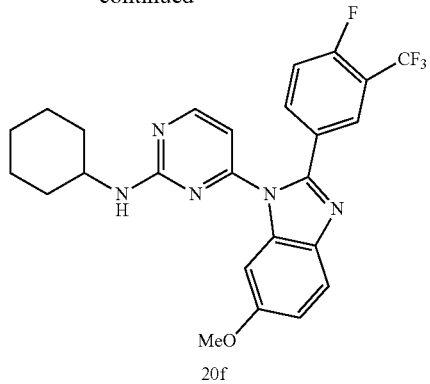

¹H NMR (400 MHz, CDCl₃) δ 8.32 (s, 1H), 7.96 (d, J=5.1 Hz, 1H), 7.75 (s, 1H), 7.67 (s, 1H), 7.22 (m, 2H), 7.02 (dd, J=8.8, 2.2 Hz, 1H), 6.43 (s, 1H), 3.86 (s, 3H), 3.39 (s, 1H), 2.03 (m, 1H), 1.69 (m, 3H), 1.59 (m, 1H), 1.22 (m, 6H).

<Preparation Example 2-30> 4-(2-(benzo[d][1,3]dioxole-5-yl)-6-methoxy-1H-benzo[d]imidazole-1-yl)-N-cyclohexylpyrimidin-2-amine (20g)

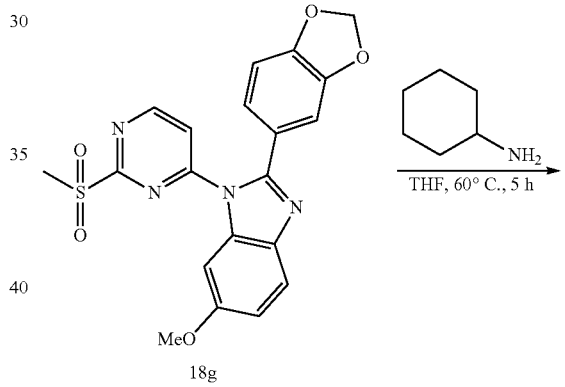

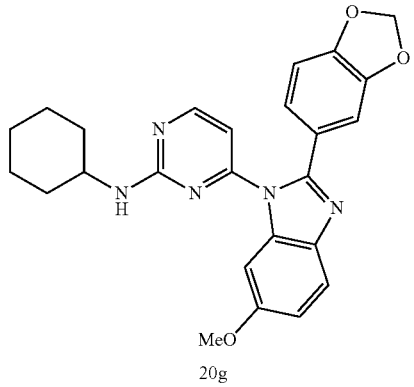

¹H NMR (400 MHz, CDCl₃) δ 8.23 (s, 1H), 7.72 (d, J=8.8 Hz, 1H), 7.29 (d, J=2.2 Hz, 1H), 7.09-7.03 (m, 2H), 6.98 (dd, J=8.8, 2.4 Hz, 1H), 6.81 (d, J=8.0 Hz, 1H), 6.23 (s, 1H), 6.00 (s, 2H), 3.84 (s, 3H), 3.81-3.67 (s, 1H), 1.98 (m, 2H), 1.72 (m, 2H), 1.62 (m, 1H), 1.24 (m, 6H).

<Preparation Example 2-31> (S)-tert-butyl 3-((4-(6-methoxy-2-(naphthalene-2-yl)-1H-benzo[d]imidazole-1-yl)pyrimidin-2-yl)amino)piperidine-1-carboxylate (21a)

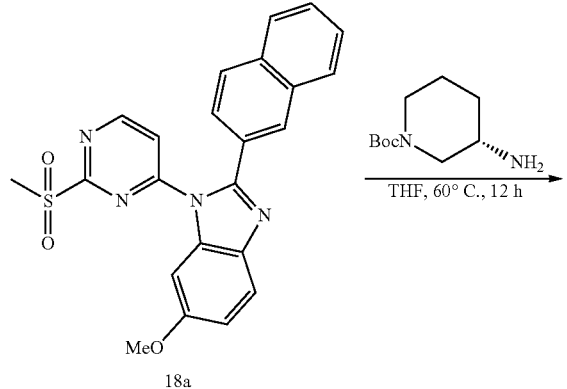

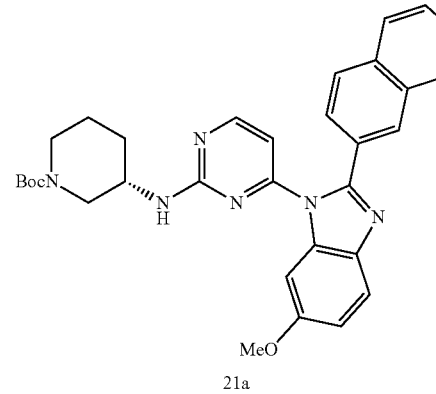

Compound 18a (250 mg, 0.58 mmol) and (S)-tert-butyl-3-aminopiperidine-1-carboxylate (228 µl) were stirred in THF (4 ml) at 60° C. for 12 hours. After the completion of the reaction, the reaction mixture was cooled to ambient temperature and the filtrate was distilled under reduced pressure. The residue was purified by column chromatography (silica gel, n-hexane:ethyl acetate=1:1) to obtain Compound 21a (180 mg, 57%).

¹H NMR (400 MHz, CDCl₃) δ 8.19 (d, J=5.2 Hz, 2H), 7.85 (m, 2H), 7.79 (m, 2H), 7.56-7.47 (m, 3H), 7.36 (s, 1H), 7.01 (dd, J=8.8, 2.4 Hz, 1H), 6.29 (s, 1H), 3.86 (s, 3H), 3.78-3.57 (s, 1H), 3.32 (m, 3H), 1.76-1.52 (m, 2H), 1.43 (s, 9H), 1.28 (m, 1H), 1.25 (d, J=7.1 Hz, 2H), 1.17-0.79 (m, 1H).

In the same manner as in Preparation Example 2-31, the compounds of Preparation Examples 2-32 to 2-37 were obtained (Compound 21b (100 mg, 50%), 21c (159 mg, 66%), 21d (90 mg, 52%), 21e (210 mg, 55%), 21f (93 mg, 50%), 21g (190 mg, 58%)).

<Preparation Example 2-32> (S)-tert-butyl 3-((4-(6-methoxy-2-(Quinoline-2-yl)-1H-benzo[d]imidazole-1-yl)pyrimidin-2-yl)amino)piperidine-1-carboxylate (21b)

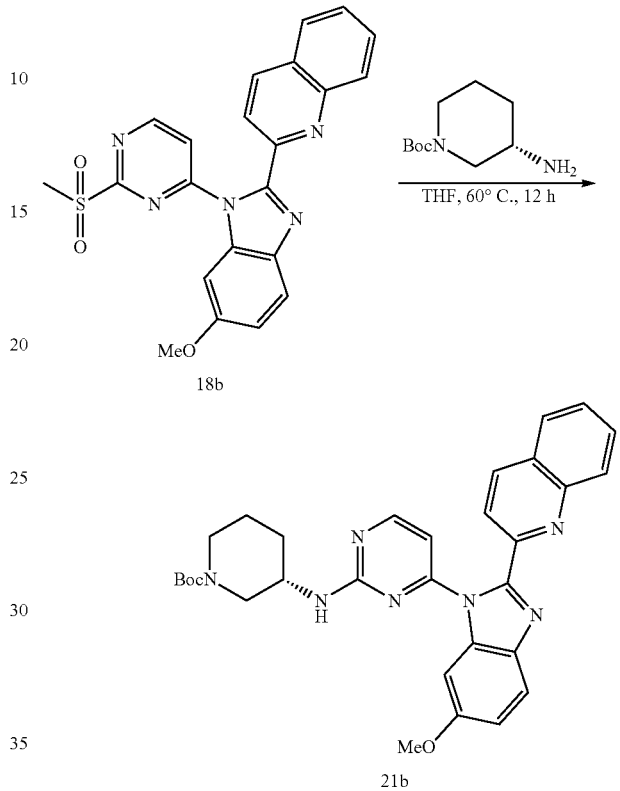

¹H NMR (400 MHz, CDCl₃) δ 8.26 (d, J=4.0 Hz, 1H), 8.17 (s, 2H), 7.73 (dd, J=8.3, 3.7 Hz, 2H), 7.64 (d, J=7.2 Hz, 1H), 7.59-7.52 (m, 1H), 7.49-7.42 (m, 1H), 7.06 (s, 1H), 6.94 (dd, J=8.8, 2.4 Hz, 1H), 6.44 (d, J=4.0 Hz, 1H), 5.28 (s, 1H), 3.79 (s, 3H), 1.56-1.35 (m, 4H), 1.20 (m, 2H), 1.07-0.86 (m, 4H), 0.80 (m, 1H).

<Preparation Example 2-33> (S)-tert-butyl 3-((4-(2-(2,3-dihydrobenzo[b][1,4]dioxin-6-yl)-6-methoxy-1H-benzo[d]imidazole-1-yl)pyrimidin-2-yl)amino)piperidine-1-carboxylate (21c)

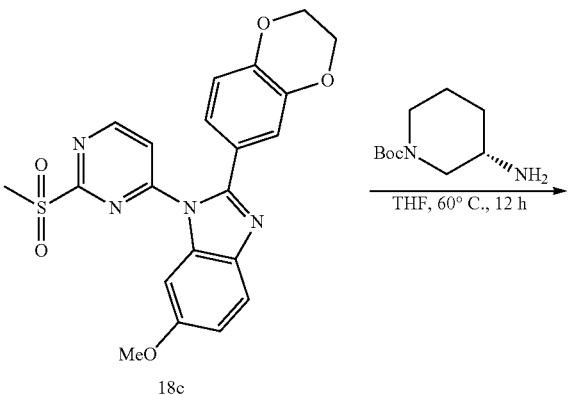

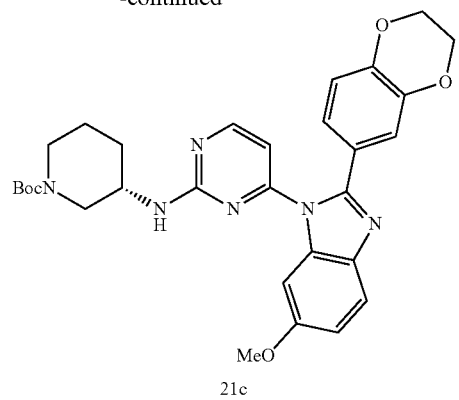

21c

¹H NMR (400 MHz, CDCl₃) δ 8.20 (d, J=5.2 Hz, 1H), 7.64 (d, J=8.8 Hz, 1H), 7.29 (s, 1H), 7.08 (s, 1H), 6.96 (dd, J=8.4, 1.7 Hz, 1H), 6.91 (dd, J=8.8, 2.2 Hz, 1H), 6.80 (d, J=8.4 Hz, 1H), 6.19 (s, 1H), 5.88 (s, 1H), 4.21 (d, J=6.5 Hz, 2H), 4.17 (d, J=6.5 Hz, 2H), 3.78 (s, 3H), 3.45 (m, 1H), 3.20 (m, 2H), 1.67 (m, 1H), 1.47 (m, 3H), 1.35 (s, 9H), 1.20 (m, 2H).

<Preparation Example 2-34> (S)-tert-butyl 3-((4-(2-(benzofuran-5-yl)-6-methoxy-1H-benzo[d]imidazole-1-yl)pyrimidin-2-yl)amino)piperidine-1-carboxylate (21d)

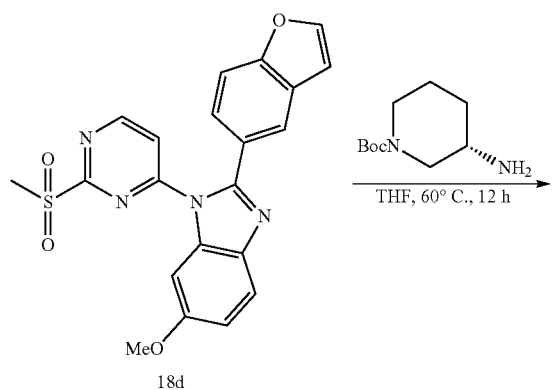

21d

¹H NMR (400 MHz, CDCl₃) δ 8.21 (s, 1H), 7.98 (s, 1H), 7.86 (d, J=8.8 Hz, 1H), 7.69 (d, J=1.7 Hz, 1H), 7.53 (d, J=8.0 Hz, 1H), 7.47 (d, J=8.0 Hz, 1H), 7.33 (s, 1H), 7.06 (d, J=8.8 Hz, 1H), 6.84 (d, J=1.7 Hz, 1H), 6.26 (s, 1H), 3.86 (s, 3H), 3.70 (s, 1H), 3.46 (s, 1H), 3.31 (m, 2H), 1.70 (m, 2H), 1.48 (m, 2H), 1.45 (m, 2H), 1.42 (s, 9H).

<Preparation Example 2-35> (S)-tert-butyl 3-((4-(2-(3,4-dichlorophenyl)-6-methoxy-1H-benzo[d]imidazole-1-yl)pyrimidin-2-yl)amino)piperidine-1-carboxylate (21e)

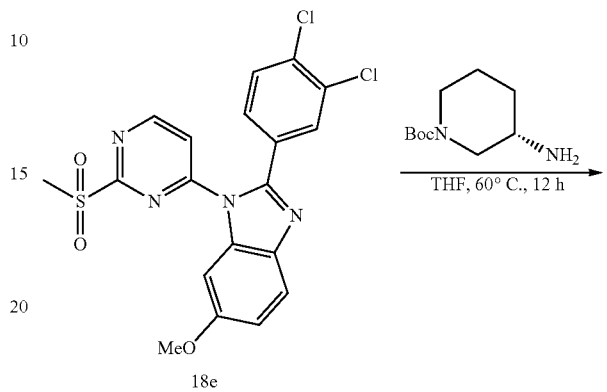

21e

¹H NMR (400 MHz, CDCl₃) δ 8.32 (d, J=4.8 Hz, 1H), 7.78 (s, 1H), 7.70 (d, J=8.8 Hz, 1H), 7.41 (d, J=8.3 Hz, 1H), 7.26 (dd, J=8.3, 1.9 Hz, 1H), 7.21 (s, 1H), 6.98 (dd, J=8.8, 2.4 Hz, 1H), 6.36 (s, 1H), 5.78 (s, 1H), 3.83 (s, 3H), 3.65 (m, 1H), 3.43 (m, 1H), 3.25 (sm, 2H), 1.76-1.61 (m, 2H), 1.42 (s, 9H), 1.25 (m, 2H), 1.24 (m, 1H).

<Preparation Example 2-36> (S)-tert-butyl 3-((4-(2-(4-fluoro-3-(trifluoromethyl)phenyl)-6-methoxy-1H-benzo[d]imidazole-1-yl)pyrimidin-2-yl)amino)piperidine-1-carboxylate (21f)

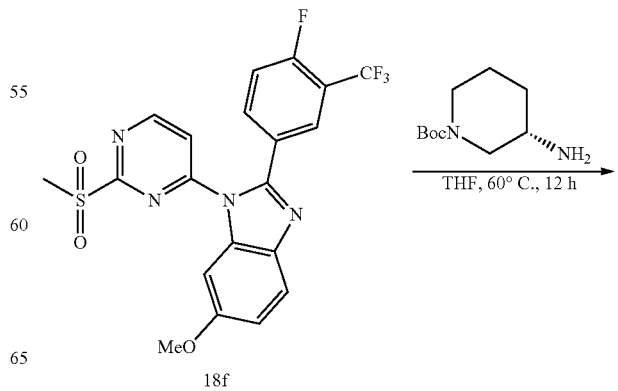

18f

-continued

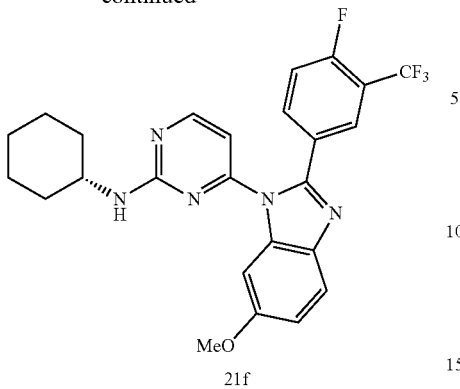

21f

¹H NMR (400 MHz, CDCl₃) δ 8.34 (d, J=4.1 Hz, 1H), 7.93 (d, J=4.1 Hz, 1H), 7.70 (d, J=8.8 Hz, 1H), 7.62 (s, 1H), 7.17 (m, 2H), 6.97 (dd, J=8.8, 2.4 Hz, 1H), 6.37 (s, 1H), 5.78 (s, 1H), 3.82 (s, 3H), 3.60 (m, 1H), 3.41 (m, 1H), 3.22 (m, 2H), 1.65 (m, 2H), 1.42 (m, 3H), 1.39 (s, 9H).

<Preparation Example 2-37> (S)-tert-butyl 3-((4-(2-(benzo[d][1,3]dioxole-5-yl)-6-methoxy-1H-benzo[d]imidazole-1-yl)pyrimidin-2-yl)amino)piperidine-1-carboxylate (21g)

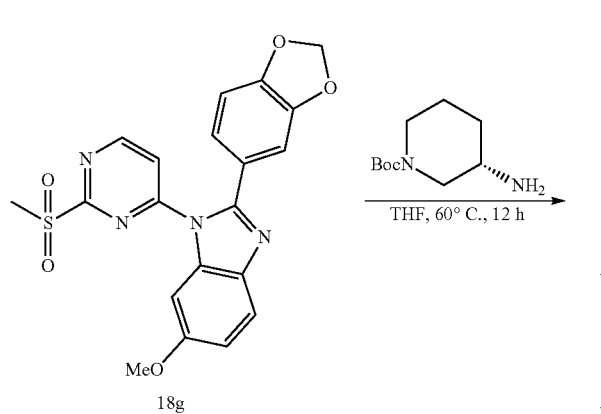

18g

21g

¹H NMR (400 MHz, CDCl₃) δ 8.21 (d, J=5.2 Hz, 1H), 7.63 (d, J=8.8 Hz, 1H), 7.26 (d, J=2.9 Hz, 1H), 7.02-6.98 (m, 2H), 6.91 (dd, J=8.8, 2.9 Hz, 1H), 6.76 (d, J=8.4 Hz, 1H), 6.19 (s, 1H), 5.95 (s, 2H), 3.78 (s, 3H), 3.44 (s, 1H), 3.20 (m, 2H), 1.83 (m, 1H), 1.68 (m, 2H), 1.53-1.45 (m, 2H), 1.45-1.31 (s, 9H), 1.21 (m, 2H).

<Example 2-1> 2-(naphthalene-2-yl)-1-(2-((tetra-hydro-2H-pyran-4-yl)amino)pyrimidin-4-yl)-1H-benzo[d]imidazole-6-ol (22a)

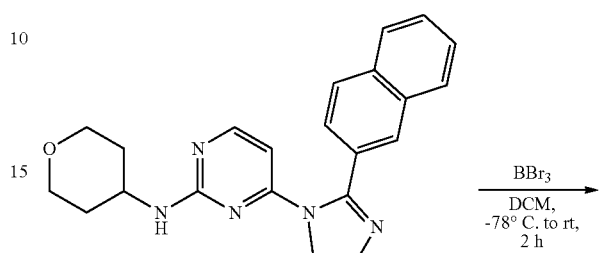

19a

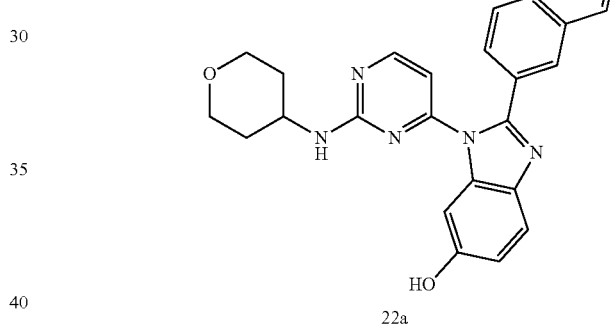

22a

Compound 19a (34 mg, 0.076 mmol) was dissolved in methylene chloride (0.8 ml), BBr₃ (0.38 ml) was added at −78° C., and stirred for about 1 hour, and then stirred at room temperature for about 2 hours. After confirming the completion of the reaction, methanol was added and quenched. The organic solvent was distilled under reduced pressure, extracted with methylene chloride, and washed with a saturated NaHCO₃ aqueous solution. The extracted organic layer was dried over magnesium sulfateanhydrous, filtered, and the filtrate was distilled under reduced pressure, and the residue was purified by column chromatography (silica gel, methylene chloride:MeOH=20:1) to obtain Compound 22a (20 mg, 60%).

¹H NMR (400 MHz, DMSO-d6) δ 9.54 (s, 1H), 8.47 (s, 1H), 8.16 (s, 1H), 7.91-7.97 (m, 3H), 7.39-7.62 (m, 5H), 7.06 (s, 1H), 6.84-6.87 (m, 1H), 3.03-3.07 (m, 1H), 2.63-2.67 (m, 1H), 1.98 (d, J=14.0 Hz, 1H), 1.72-1.75 (m, 1H), 1.46 (s, 1H), 1.14-1.24 (m, 2H), 1.02-1.10 (m, 2H)

In the same manner as in Example 2-1, the compounds of Examples 2-2 to 2-6 were obtained (Compound 22b (17 mg, 77%), 22c (17 mg, 81%), 22d (10 mg, 30%), 22e (13 mg, 50%), 22f (9 mg, 51%)).

<Example 2-2> 2-(Quinoline-2-yl)-1-(2-((tetrahydro-2H-pyran-4-yl)amino)pyrimidin-4-yl)-1H-benzo[d]imidazole-6-ol (22b)

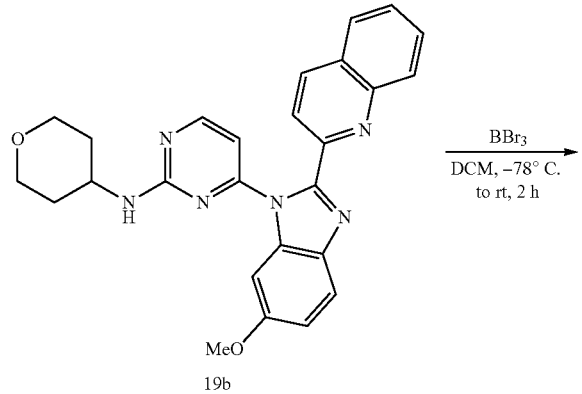

¹H NMR (400 MHz, DMSO) δ 9.68 (s, 1H), 8.55-8.45 (m, 2H), 8.24-8.09 (m, 1H), 8.01 (d, J=8.0 Hz, 1H), 7.72 (m, 1H), 7.67 (m, 1H), 7.64-7.59 (m, 1H), 7.30 (s, 1H), 6.94 (dd, J=13.6, 2.1 Hz, 1H), 6.91-6.86 (m, 1H), 3.43 (s, 1H), 2.80 (s, 1H), 1.46 (m, 2H), 1.23 (m, 3H), 0.91 (m, 4H).

<Example 2-3> 2-(2,3-dihydrobenzo[b][1,4]dioxin-6-yl)-1-(2-((tetrahydro-2H-pyran-4-yl)amino)pyrimidin-4-yl)-1H-benzo[d]imidazole-6-ol (22c)

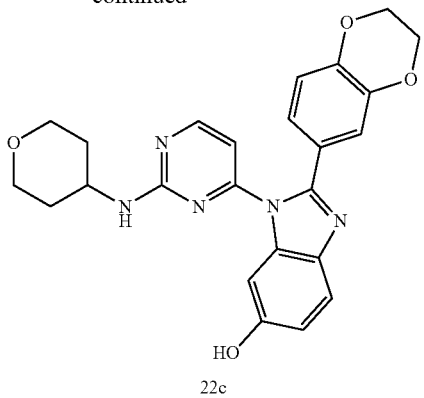

¹H NMR (400 MHz, CD₃OD) δ 8.37 (s, 1H), 7.53 (d, J=8.4 Hz, 1H), 7.07 (s, 1H), 7.01 (s, 1H), 6.97 (dd, J=8.4, 2.1 Hz, 1H), 6.90-6.85 (m, 2H), 6.64 (s, 1H), 4.28 (d, J=5.0 Hz, 2H), 4.26 (d, J=5.0 Hz, 2H), 3.90 (m, 2H), 3.62 (s, 1H), 3.39 (s, 1H), 1.29 (m, 4H), 0.91 (m, 3H).

<Example 2-4> 2-(benzofuran-5-yl)-1-(2-((tetrahydro-2H-pyran-4-yl)amino)pyrimidin-4-yl)-1H-benzo[d]imidazole-6-ol (22d)

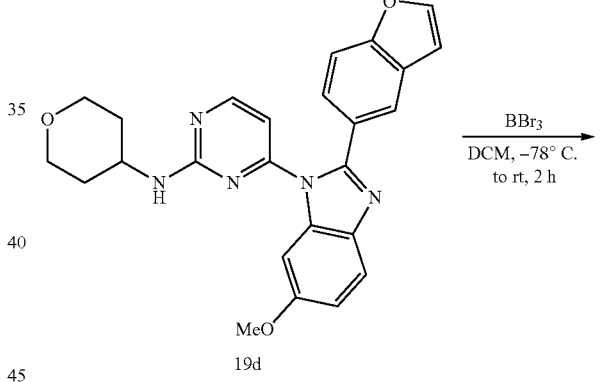

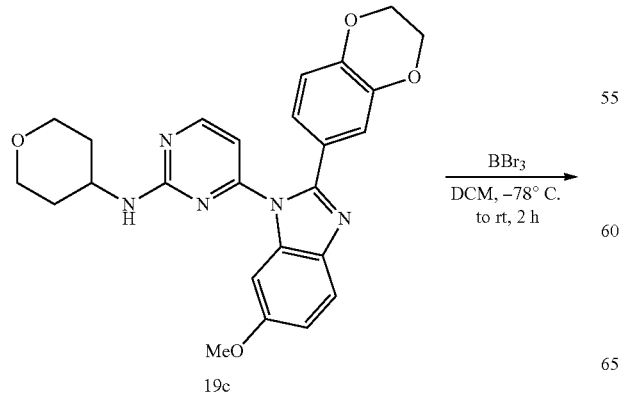

¹H NMR (400 MHz, CD₃OD) δ 8.00 (d, J=7.1 Hz, 1H), 7.97 (d, J=1.5 Hz, 1H), 7.91 (d, J=1.5 Hz, 1H), 7.69 (m, 2H), 7.61-7.56 (m, 2H), 6.99-6.95 (m, 2H), 6.20 (d, J=7.1 Hz, 1H), 4.28 (m, 2H), 3.99 (s, 1H), 3.86-3.74 (m, 2H), 2.43-2.34 (m, 1H), 2.14-2.02 (m, 2H), 1.92-1.72 (m, 2H), 1.28 (m, 1H).

Example 2-5> 2-(3,4-dichlorophenyl)-1-(2-((tetra-hydro-2H-pyran-4-yl)amino)pyrimidin-4-yl)-1H-benzo[d]imidazole-6-ol (22e)

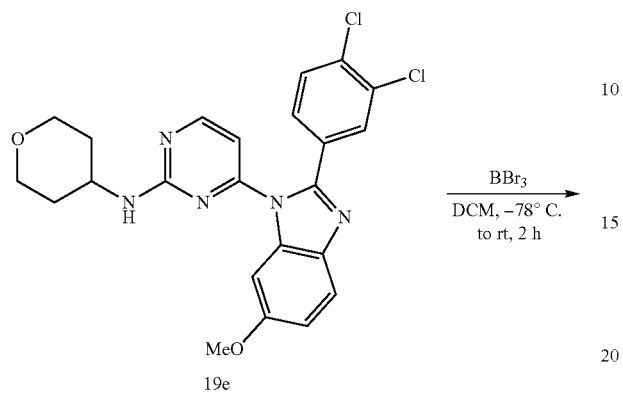

<sup>1</sup>H NMR (400 MHz, MeOD) δ 8.45 (s, 1H), 7.74 (d, J=2.0 Hz, 1H), 7.59 (dd, J=8.5, 6.0 Hz, 2H), 7.38 (dd, J=8.5, 2.0 Hz, 1H), 7.08 (s, 1H), 6.96 (s, 1H), 6.91 (dd, J=8.7, 2.3 Hz, 1H), 3.87 (m, 2H), 1.81 (s, 2H), 1.46 (m, 4H), 1.15 (m, 1H), 1.00-0.74 (m, 2H).

Example 2-6> 2-(4-fluoro-3-(trifluoromethyl)phenyl)-1-(2-((tetrahydro-2H-pyran-4-yl)amino)pyrimidin-4-yl)-1H-benzo[d]imidazole-6-ol (22f)

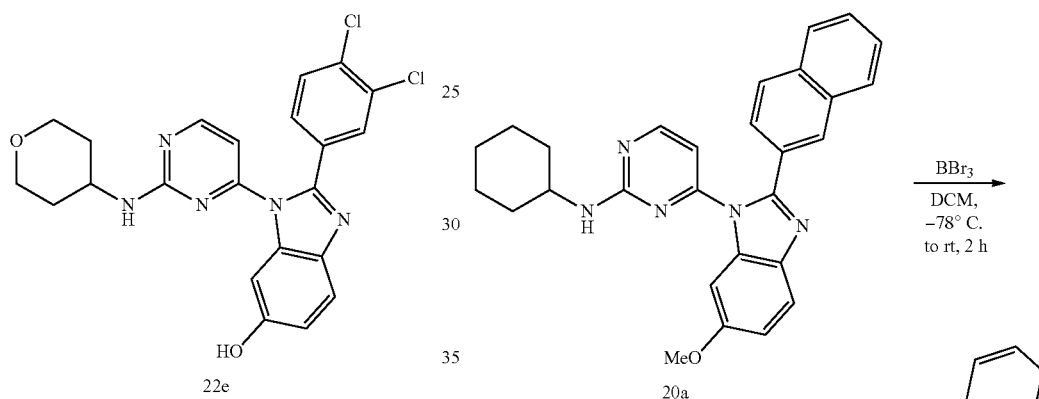

Example 2-7> 1-(2-(cyclohexylamino)pyrimidin-4-yl)-2-(naphthalene-2-yl)-1H-benzo[d]imidazole-6-ol (23a)

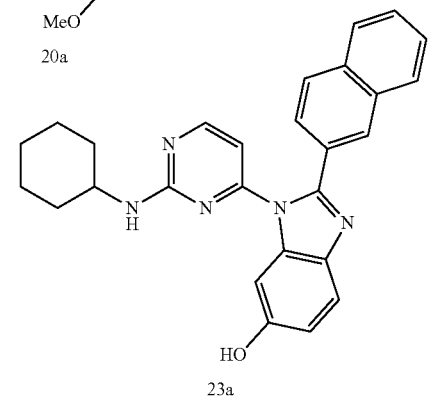

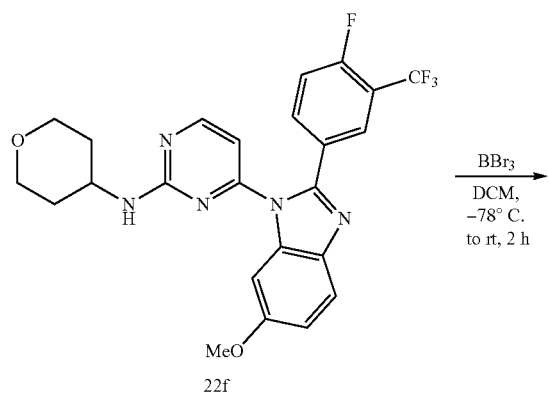

Compound 20a (28 mg, 0.06 mmol) was dissolved in methylene chloride (0.6 ml), BBr₃ (0.3 ml) was added at −78° C. and stirred for about 1 hour, and then stirred at room temperature for about 2 hours. After confirming the completion of the reaction, methanol was added and quenched. The organic solvent was distilled under reduced pressure, extracted with methylene chloride, and washed with a saturated NaHCO₃ aqueous solution. The extracted organic layer was dried over magnesium sulfate anhydrous, filtered, and the filtrate was distilled under reduced pressure, and the residue was purified by column chromatography (silica gel, methylene chloride:MeOH=20:1) to obtain Compound 23a (10 mg, 38%).

<sup>1</sup>H NMR (400 MHz, DMSO-d6) δ 8.42 (s, 1H), 8.15 (s, 1H), 7.93-7.95 (m, 4H), 7.28-7.62 (m, 5H), 7.07 (s, 1H), 6.85 (dd, J=8.8 Hz, J=2.4 Hz, 1H), 6.72 (s, 1H), 2.89 (br, s, 1H), 1.23 (m, 6H), 0.66-0.85 (m, 4H)

In the same manner as in Example 2-7, the compounds of Examples 2-8 to 2-13 were obtained (Compound 23b, 23c (23 mg, 78%), 23d (19 mg, 57%), 23e (13 mg, 76%), 23f (15 mg, 78%). 23g).

<Example 2-8> 3-(2-(cyclohexylamino)pyrimidin-4-yl)-2-(Quinoline-2-yl)-3H-benz[d]imidazole-5-ol (23b)

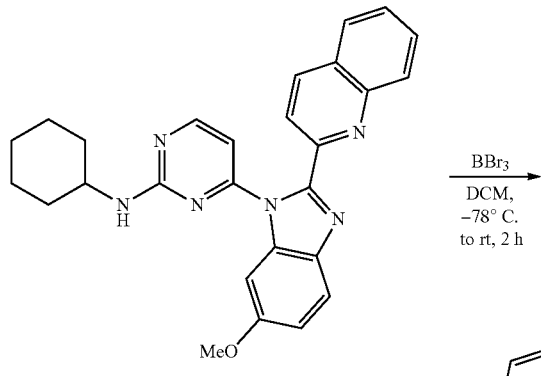

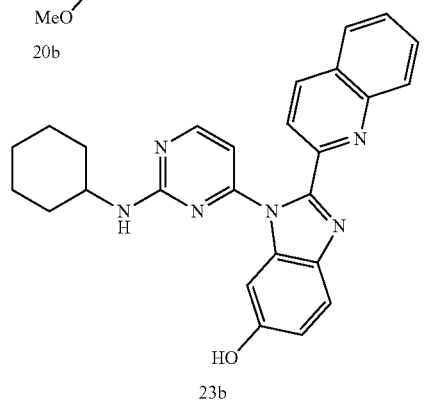

¹H NMR (400 MHz, DMSO) δ 8.52 (m, 2H), 8.18 (s, 1H), 8.03 (dd, J=16.3, 7.8 Hz, 1H), 7.76-7.70 (m, 1H), 7.70-7.65 (m, 1H), 7.65-7.59 (m, 1H), 7.56-7.40 (m, 1H), 7.29 (s, 1H), 6.92 (dd, J=25.0, 9.5 Hz, 2H), 2.87 (s, 1H), 1.99-1.82 (m, 1H), 1.70 (m, 1H), 1.26 (m, 4H), 1.07 (m, 2H), 0.84 (m, 4H).

<Example 2-9> 1-(2-(cyclohexylamino)pyrimidin-4-yl)-2-(2,3-dihydrobenzo[b][1,4]dioxin-6-yl)-1H-benzo[d]imidazole-6-ol (23c)

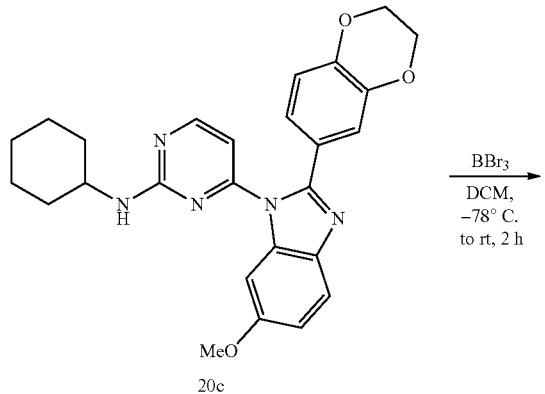

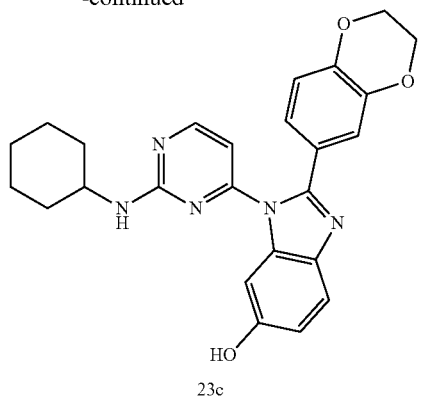

¹H NMR (400 MHz, CD₃OD) δ 8.22 (s, 1H), 7.42 (d, J=8.6 Hz, 1H), 6.98 (s, 1H), 6.91 (s, 1H), 6.86 (dd, J=8.4, 2.1 Hz, 1H), 6.77 (dd, J=8.6, 2.4 Hz, 2H), 6.46 (s, 1H), 4.17 (d, J=5.1 Hz, 2H), 4.15 (d, J=5.1 Hz, 2H), 3.34 (s, 1H), 2.20-1.78 (m, 1H), 1.61 (m, 3H), 1.53 (m, 1H), 1.18 (m, 2H), 1.14-0.74 (m, 4H).

<Example 2-10> 2-(benzofuran-5-yl)-1-(2-(cyclohexylamino)pyrimidin-4-yl)-1H-benzo[d]imidazole-6-ol (23d)

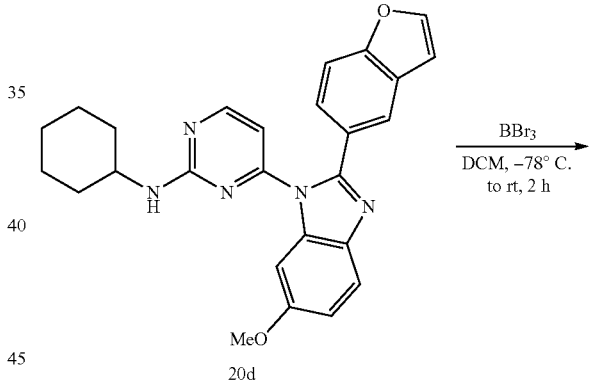

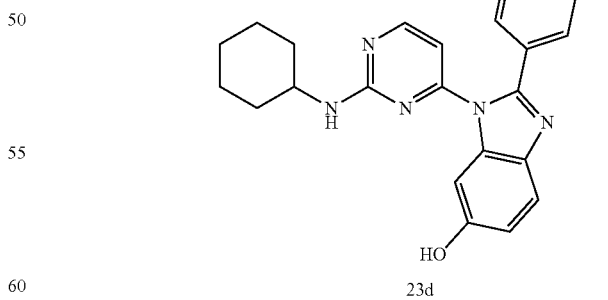

¹H NMR (400 MHz, CD₃OD) δ 8.30 (d, J=1.5 Hz, 1H), 7.85 (dd, J=6.7, 2.2 Hz, 2H), 7.57 (d, J=8.6 Hz, 2H), 7.43 (d, J=8.6 Hz, 1H), 7.15 (s, 1H), 6.90 (dd, J=10.3, 1.5 Hz, 2H), 6.64 (s, 1H), 3.95-3.81 (m, 1H), 3.56 (s, 1H), 2.00 (m, 2H), 1.57 (m, 5H), 0.96-0.81 (m, 4H).

<Example 2-11> 1-(2-(cyclohexylamino)pyrimidin-4-yl)-2-(3,4-dichlorophenyl)-1H-benzo[d]imidazole-6-ol (23e)

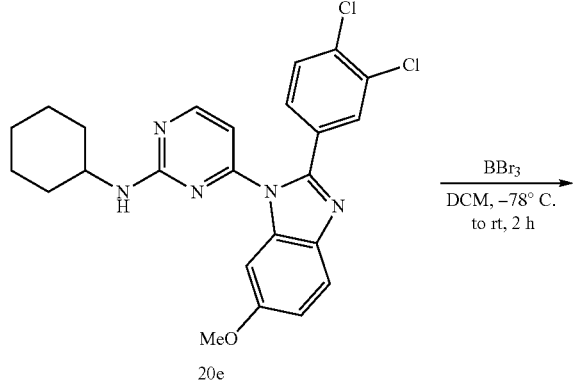

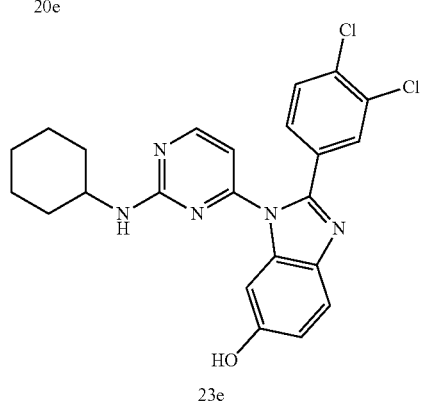

¹H NMR (400 MHz, CD₃OD) δ 8.32 (s, 1H), 7.64 (s, 1H), 7.49 (dd, J=8.5, 3.7 Hz, 2H), 7.28 (d, J=8.5 Hz, 1H), 6.99 (s, 1H), 6.82 (dd, J=8.7, 2.3 Hz, 1H), 6.68 (s, 1H), 3.13-2.89 (s, 1H), 1.67-1.39 (m, 6H), 1.04 (m, 5H), 0.79 (m, 1H).

<Example 2-12> 1-(2-(cyclohexylamino)pyrimidin-4-yl)-2-(4-fluoro-3-(trifluoromethyl)phenyl)-1H-benzo[d]imidazole-6-ol (23f)

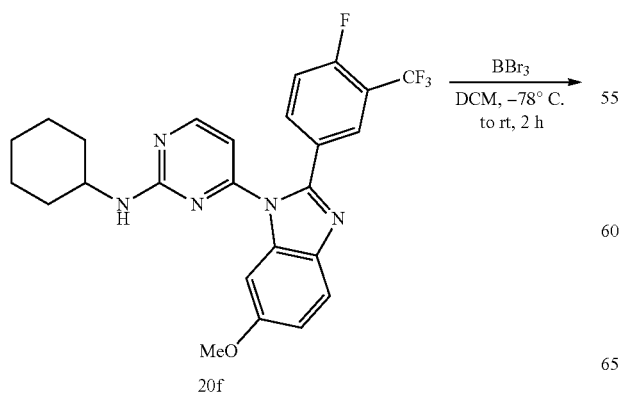

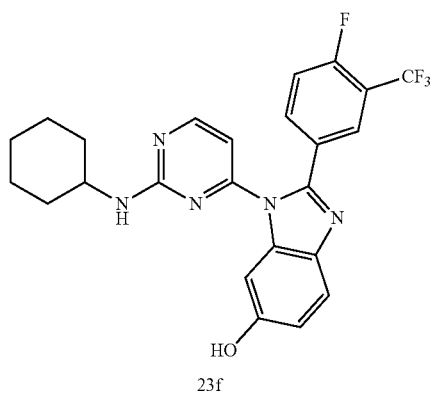

¹H NMR (400 MHz, DMSO) δ 9.64 (s, 1H), 8.53-8.45 (m, 1H), 7.83 (d, J=5.5 Hz, 1H), 7.61 (dd, J=13.7, 5.5 Hz, 2H), 7.48 (d, J=7.9 Hz, 1H), 7.00 (s, 1H), 6.86 (dd, J=9.0, 2.0 Hz, 1H), 2.93 (s, 1H), 1.79 (s, 1H), 1.50 (m, 3H), 1.30 (m, 3H), 0.97 (m, 4H), 0.85 (m, 1H).

<Example 2-13> 2-(benzo[d][1,3]dioxol-5-yl)-3-(2-(cyclohexylamino)pyrimidin-4-yl)-3H-benz[d]imidazole-5-ol (23g)

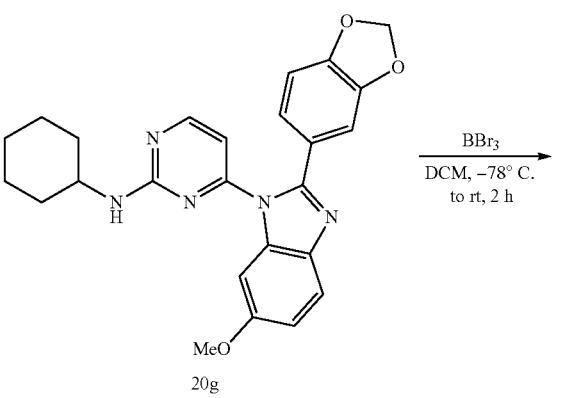

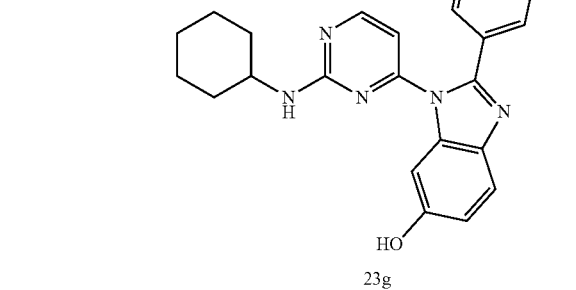

¹H NMR (400 MHz, MeOD) δ 8.29 (s, 1H), 7.51 (d, J=8.7 Hz, 1H), 7.13 (s, 1H), 6.95 (d, J=1.9 Hz, 1H), 6.86 (dd, J=8.7, 2.3 Hz, 2H), 6.80 (d, J=8.2 Hz, 1H), 6.49 (s, 1H), 3.48 (s, 1H), 2.08-1.86 (m, 2H), 1.74 (m, 4H), 1.61 (m, 2H), 1.25-1.11 (m, 4H), 0.97-0.82 (m, 2H).

<Example 2-14> (S)-4-(6-methoxy-2-(naphthalene-2-yl)-1H-benzo[d]imidazole-1-yl)-N-(piperidine-3-yl)pyrimidin-2-amine (24a)

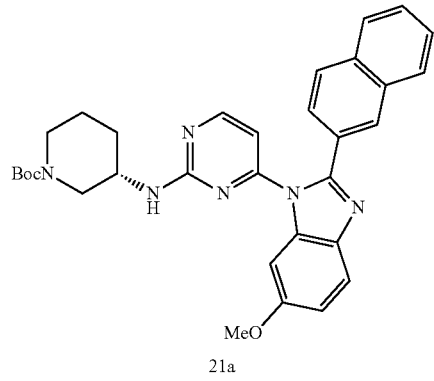

Compound 21a (95 mg, 0.172 mmol) was dissolved in 1,4-dioxane (1.75 ml) and 4 M–HCl (0.87 ml) containing 1,4-dioxane was treated at room temperature. The reaction mixture was stirred at room temperature for 20 minutes, the mixture was diluted with ether and then stirred until the product separated to a solid. The solid product was filtered off and washed with ether followed by hexane. The crude product was then crystallized to give Compound 24a (52 mg, 67%).

$^1$H NMR (400 MHz, DMSO) δ 8.41 (s, 1H), 8.17 (s, 1H), 7.99-7.92 (m, 3H), 7.79 (d, J=26.2 Hz, 1H), 7.71 (d, J=8.8 Hz, 1H), 7.57 (m, 3H), 7.33 (m, 1H), 7.00 (dd, J=8.8, 2.4 Hz, 1H), 6.51 (s, 1H), 3.84 (s, 3H), 3.69 (s, 1H), 3.43-3.20 (m, 1H), 2.96 (m, 2H), 2.81-2.53 (m, 2H), 1.99-1.45 (m, 2H), 1.41-1.04 (m, 3H).

In the same manner as in Example 2-14, the compounds of Examples 2-15 to 2-20 were obtained (Compound 24b (43 mg, 81%), 24c (110 mg, 90%), 24d (30 mg, 43%), 24e (110 mg, 62%), 24f (57 mg, 80%), 24g (118 mg, 77%)).

<Example 2-15> (S)-4-(6-methoxy-2-(Quinoline-2-yl)-1H-benzo[d]imidazole-1-yl)-N-(piperidine-3-yl)pyrimidin-2-amine (24b)

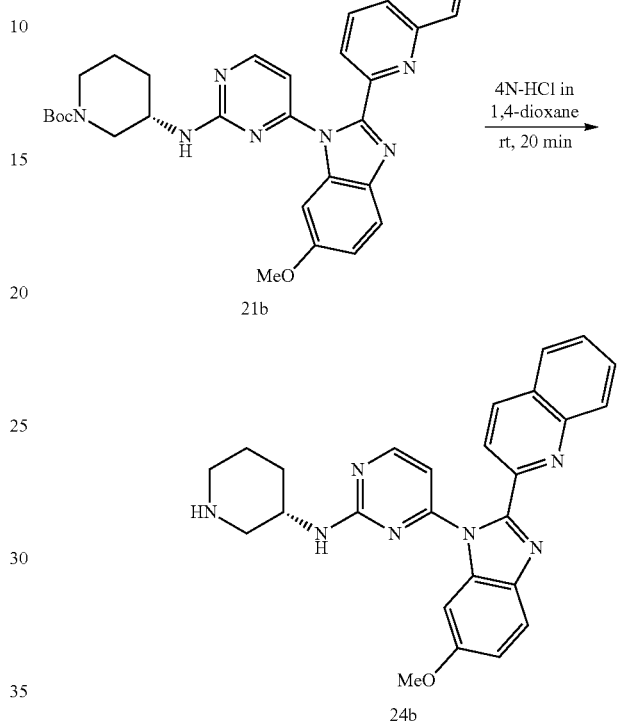

$^1$H NMR (400 MHz, CDCl$_3$) δ 8.33 (d, J=6.7 Hz, 2H), 7.76 (d, J=8.0 Hz, 2H), 7.62 (d, J=8.4 Hz, 1H), 7.56 (m, 2H), 7.43 (m, 1H), 7.02 (s, 1H), 6.97 (d, J=8.9 Hz, 1H), 6.78 (s, 1H), 4.15-3.80 (s, 1H), 3.60 (s, 3H), 3.28-3.22 (m, 1H), 3.20-2.99 (m, 1H), 2.96 (m, 1H), 2.94-2.75 (m, 1H), 2.62 (m, 2H), 1.87-1.60 (m, 1H), 1.39 (m, 1H), 1.24 (m, 2H).

<Example 2-16> (S)-4-(2-(2,3-dihydrobenzo[b][1,4]dioxin-6-yl)-6-methoxy-1H-benzo[d]imidazole-1-yl)-N-(piperidine-3-yl)pyrimidin-2-amine (24c)

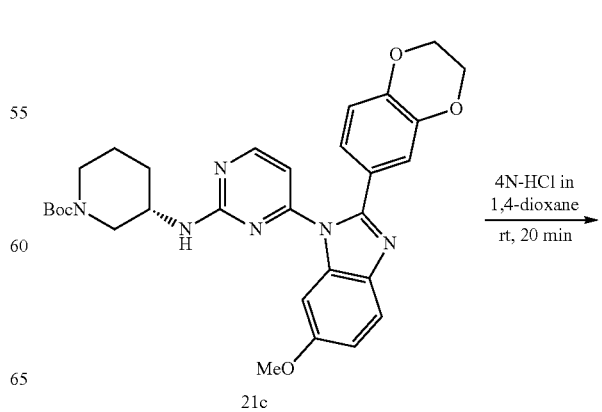

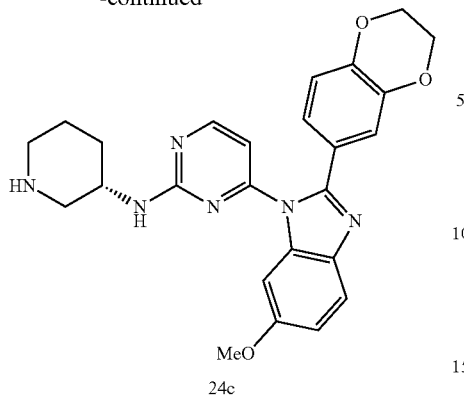

24c

¹H NMR (400 MHz, DMSO) δ 8.13 (s, 1H), 7.35 (d, J=8.7 Hz, 1H), 6.87 (s, 1H), 6.69 (m, 3H), 6.57 (d, J=8.7 Hz, 1H), 6.31 (s, 1H), 4.02-3.86 (m, 4H), 3.69 (s, 1H), 3.54 (s, 3H), 3.04 (s, 1H), 3.03-2.96 (m, 2H), 2.78-2.54 (m, 2H), 1.71 (m, 2H), 1.41 (m, 2H), 1.12-0.53 (m, 1H).

<Example 2-17> (S)-4-(2-(benzofuran-5-yl)-6-methoxy-1H-benzo[d]imidazole-1-yl)-N-(piperidine-3-yl)pyrimidin-2-amine (24d)

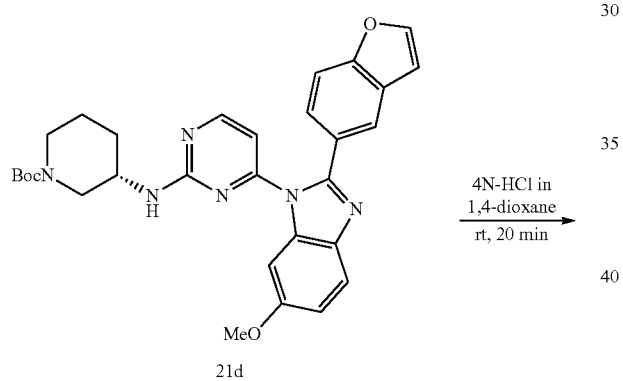

21d

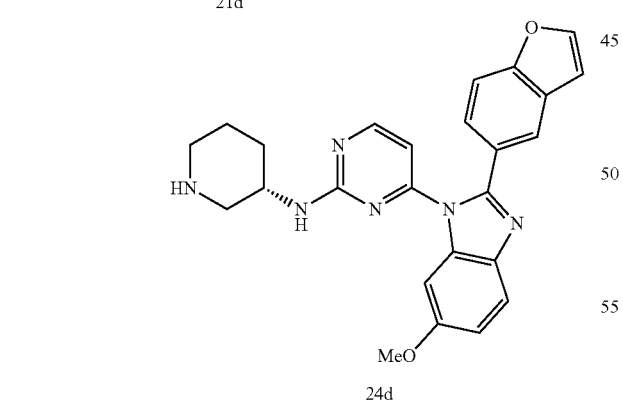

24d

¹H NMR (400 MHz, CD₃OD) δ 8.79 (s, 1H), 8.25 (d, J=2.1 Hz, 1H), 8.23 (s, 1H), 8.07 (d, J=8.8 Hz, 1H), 7.96 (d, J=8.5 Hz, 1H), 7.84 (d, J=8.5 Hz, 1H), 7.63 (s, 1H), 7.40 (dd, J=8.8, 2.3 Hz, 1H), 7.30 (d, J=1.6 Hz, 1H), 7.08 (s, 1H), 4.25 (s, 3H), 4.04 (s, 1H), 3.65 (s, 1H), 3.38 (m, 2H), 2.41 (m, 1H), 2.25 (m, 1H), 1.89 (m, 3H), 1.67 (m, 1H), 1.58-1.10 (m, 1H).

<Example 2-18> (S)-4-(2-(3,4-dichlorophenyl)-6-methoxy-1H-benzo[d]imidazole-1-yl)-N-(piperidine-3-yl)pyrimidin-2-amine (24e)

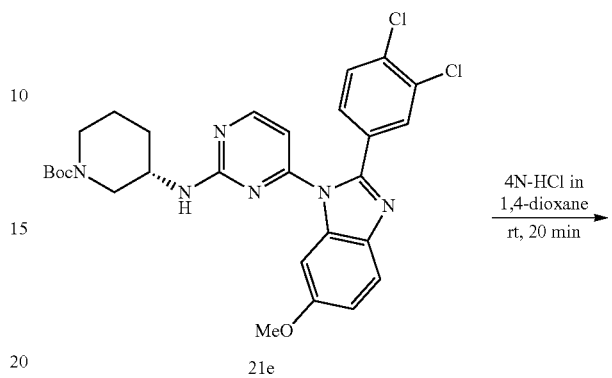

21e

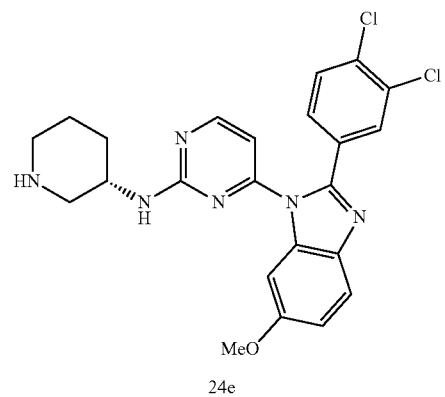

24e

¹H NMR (400 MHz, DMSO) δ 9.69 (s, 1H), 9.41 (m, 3H), 8.58-8.46 (m, 1H), 8.26 (m, 1H), 7.90 (s, 1H), 7.74 (m, 2H), 7.50 (dd, J=8.4, 2.1 Hz, 1H), 7.08 (dd, J=8.9, 2.1 Hz, 1H), 6.84-6.50 (m, 1H), 3.97 (m, 1H), 3.84 (s, 3H), 3.55 (s, 1H), 3.45-3.28 (m, 1H), 3.15 (s, 1H), 3.09 (s, 1H), 2.80 (m, 2H), 1.84 (m, 2H), 1.47 (m, 2H).

<Example 2-19> (S)-4-(2-(4-fluoro-3-(trifluoromethyl)phenyl)-6-methoxy-1H-benzo[d]imidazole-1-yl)-N-(piperidine-3-yl)pyrimidin-2-amine (24f)

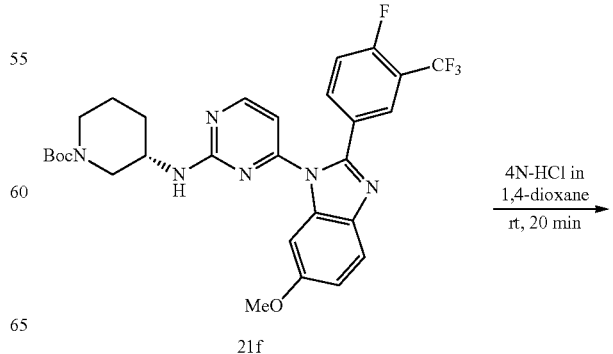

21f

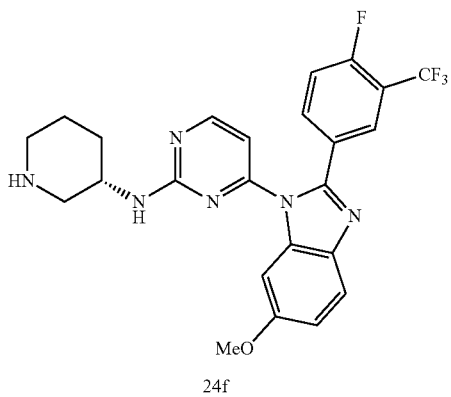

24f

¹H NMR (400 MHz, CD₃OD) δ 8.50 (s, 1H), 7.88 (d, J=5.7 Hz, 1H), 7.82 (s, 1H), 7.63 (d, J=8.8 Hz, 1H), 7.45 (m, 1H), 7.18 (s, 1H), 7.01 (dd, J=8.8, 2.3 Hz, 1H), 6.73 (s, 1H), 3.84 (s, 3H), 3.35 (s, 1H), 3.13 (m, 2H), 2.87 (m, 2H), 2.18-1.86 (m, 2H), 1.63 (m, 3H), 1.26 (m, 1H).

<Example 2-20> (S)-4-(2-(benzo[d][1,3]dioxole-5-yl)-6-methoxy-1H-benzo[d]imidazole-1-yl)-N-(piperidine-3-yl)pyrimidin-2-amine (24g)

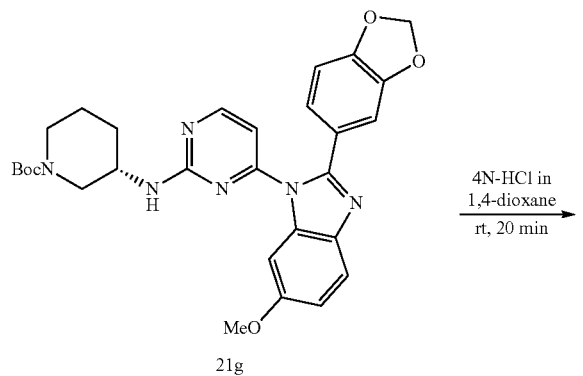

¹H NMR (400 MHz, CD₃OD) δ 8.41 (s, 1H), 7.59 (d, J=8.8 Hz, 1H), 7.17 (s, 1H), 6.99 (dd, J=8.1, 1.5 Hz, 1H), 6.98-6.95 (m, 2H), 6.86 (d, J=8.1 Hz, 1H), 6.62 (s, 1H), 6.02 (d, J=1.0 Hz, 1H), 6.01 (d, J=1.0 Hz, 1H), 4.00 (s, 1H), 3.81 (s, 3H), 3.35 (s, 1H), 3.26 (m 1H), 3.05-2.86 (m, 2H), 1.99 (m, 2H), 1.70 (m, 3H), 1.26 (m, 1H).

<Example 2-21> (S)-cyclopropyl(3-((4-(6-methoxy-2-(naphthalene-2-yl)-1H-benzo[d]imidazole-1-yl)pyrimidin-2-yl)amino)piperidine-1-yl)methanone (25a)

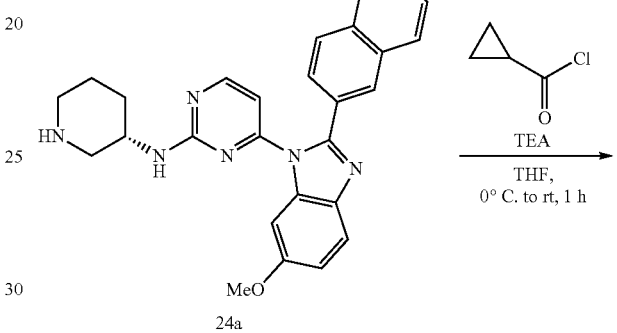

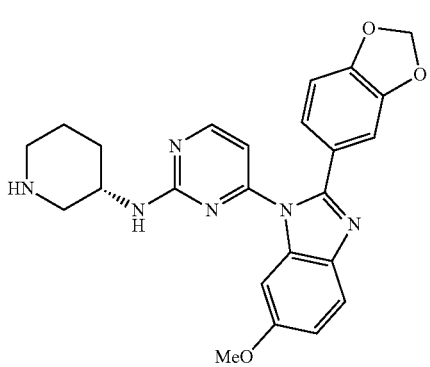

Compound 24a (52 mg, 0.12 mmol) was dissolved in THF (0.3 ml) and cooled to 0° C., then treated with TEA (24 μL). The mixture was added cyclopropanecarbonyl chloride (10 mg) at 0° C., raised to room temperature, and stirred for 1 hour. The reaction mixture was concentrated in vacuum, diluted with methylene chloride and washed with water and saturated aqueous sodium chloride solution. The organic layer was dried over sodium sulfate, filtered, and the filtrate was distilled under reduced pressure, and the residue was purified by column chromatography (silica gel, DCM: MEOH 40:1) to obtain Compound 25a (31 mg, 52%).

In the same manner as in Example 2-21, the compound of Examples 2-22 to 2-27 was obtained (Compound 25b (27 mg, 97%), 25c (76 mg, 60%), 25d (20 mg, 61%), 25e (16 mg, 39%), 25f (49 mg, 81%), 25g (60 mg, 66%)).

<Example 2-22> (S)-cyclopropyl(3-((4-(6-methoxy-2-(Quinoline-2-yl)-1H-benzo[d]imidazole-1-yl)pyrimidin-2-yl)amino)piperidine-1-yl)methanone (25b)

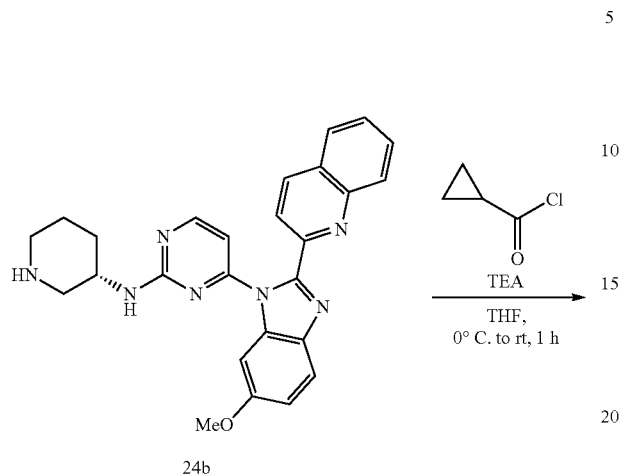

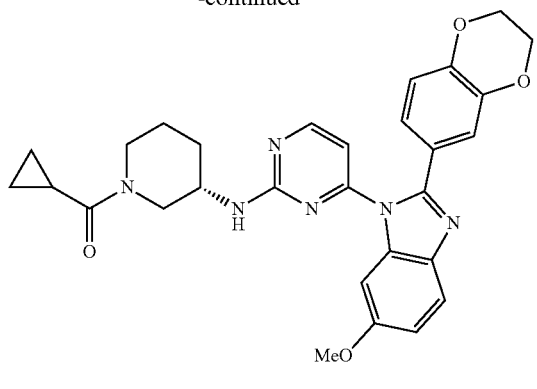

¹H NMR (400 MHz, CDCl₃) δ8.19 (s, 1H), 7.67 (d, J=8.8 Hz, 1H), 7.24 (s, 1H), 7.07 (s, 1H), 6.98 (dd, J=8.4, 2.0 Hz, 1H), 6.93 (dd, J=8.8, 2.2 Hz, 1H), 6.82 (d, J=8.4 Hz, 1H), 6.24 (s, 1H), 4.24 (d, J=5.0 Hz, 2H), 4.21 (d, J=5.0 Hz, 2H), 4.15 (s, 1H), 3.87 (m, 1H), 3.44 (m, 1H), 3.35-3.09 (m, 1H), 1.73 (m, 2H), 1.67-1.48 (m, 3H), 1.04-0.98 (m, 1H), 0.92 (m, 1H), 0.86-0.78 (m, 2H), 0.73 (m, 1H), 0.34 (m, 1H).

¹H NMR (400 MHz, CD₃OD) δ 8.43 (d, J=8.5 Hz, 1H), 8.42-8.34 (m, 1H), 8.18 (d, J=8.5 Hz, 1H), 7.95 (d, J=7.7 Hz, 1H), 7.69 (dd, J=13.5, 6.1 Hz, 2H), 7.61 (dd, J=12.6, 5.5 Hz, 2H), 7.32 (s, 1H), 7.05 (d, J=8.9 Hz, 1H), 6.77 (s, 1H), 4.18-4.06 (br, 1H), 3.97 (m, 1H), 3.89 (s, 3H), 3.13 (m, 1H), 2.86 (m, 2H), 1.91 (m, 1H), 1.48 (m, 4H), 1.22-1.03 (m, 1H), 0.93-0.48 (m, 4H), 0.15 (m, 1H).

<Example 2-23> (S)-cyclopropyl(3-((4-(2-(2,3-dihydrobenzo[b][1,4]dioxin-6-yl)-6-methoxy-1H-benzo[d]imidazole-1-yl)pyrimidin-2-yl)amino)piperidine-1-yl)methanone (25c)

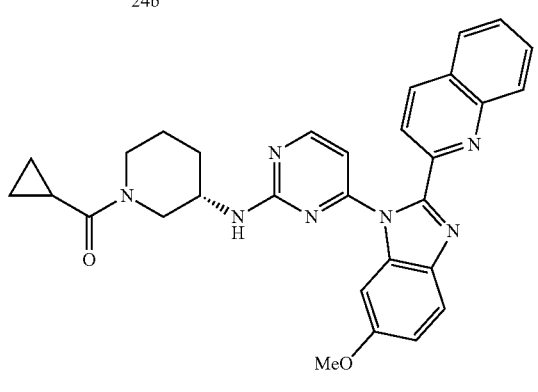

<Example 2-24> (S)-(3-((4-(2-(benzofuran-5-yl)-6-methoxy-1H-benzo[d]imidazole-1-yl)pyrimidin-2-yl)amino)piperidine-1-yl)(cyclopropyl)methanone (25d)

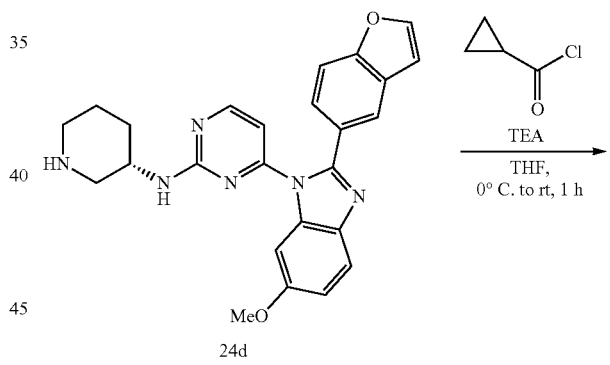

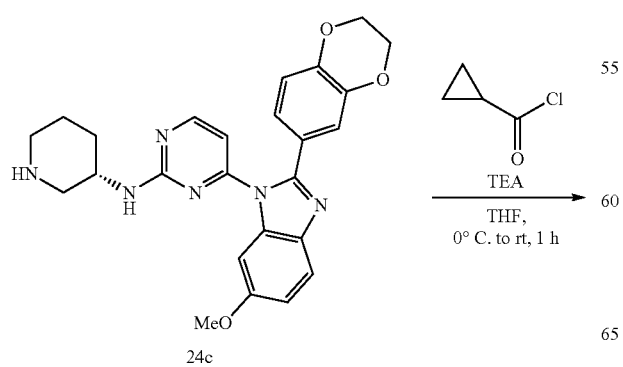

¹H NMR (400 MHz, CD₃OD) δ 8.41-8.22 (m, 1H), 7.84 (d, J=2.1 Hz, 2H), 7.69-7.60 (m, 1H), 7.59-7.52 (m, 1H), 7.42 (d, J=8.3 Hz, 1H), 7.29 (m, 1H), 7.11-6.98 (m, 1H), 6.90 (s, 1H), 6.58 (s, 1H), 4.25 (m, 1H), 4.02 (s, 1H), 3.84

(s, 3H), 3.29-3.08 (m, 1H), 2.95 (m, 1H), 1.98-1.84 (m, 1H), 1.77 (s, 1H), 1.69-1.38 (m, 3H), 0.99-0.57 (m, 5H), 0.49-0.09 (m, 1H).

<Example 2-25> (S)-cyclopropyl(3-((4-(2-(3,4-dichlorophenyl)-6-methoxy-1H-benzo[d]imidazole-1-yl)pyrimidin-2-yl)amino)piperidin-1-yl)methanone (25e)

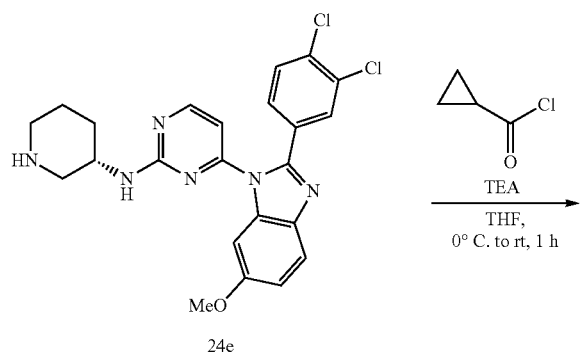

24e

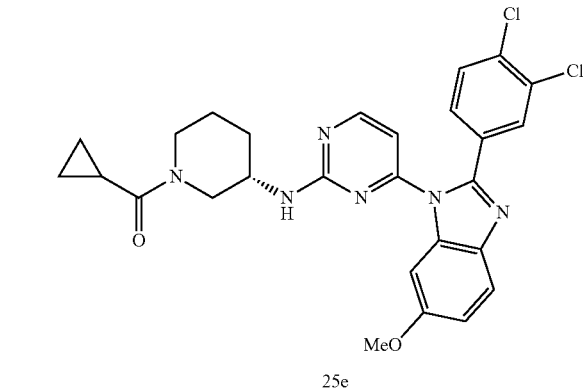

25e

¹H NMR (400 MHz, CDCl₃) δ 8.29 (s, 1H), 7.86-7.70 (m, 2H), 7.45 (d, J=8.0 Hz, 1H), 7.35-7.28 (m, 1H), 7.20 (s, 1H), 7.01 (d, J=8.8 Hz, 1H), 6.41 (s, 1H), 4.10 (s, 1H), 3.85 (s, 3H), 3.58 (s, 1H), 3.24 (m, 1H), 1.76 (m, 3H), 1.05 (m, 5H), 0.92 (m, 5H).

<Example 2-26> (S)-cyclopropyl(3-((4-(2-(4-fluoro-3-(trifluoromethyl)phenyl)-6-methoxy-1H-benzo[d]imidazole-1-yl)pyrimidin-2-yl)amino)piperidin-1-yl)methanone (25f)

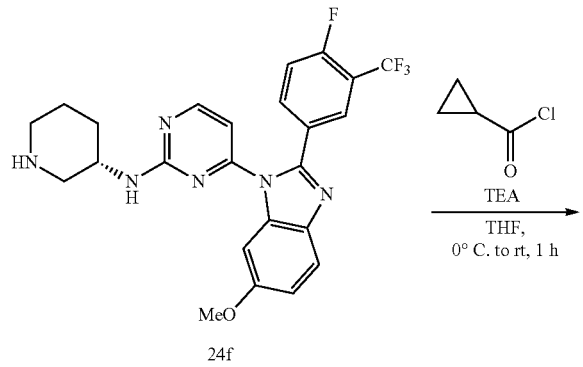

24f

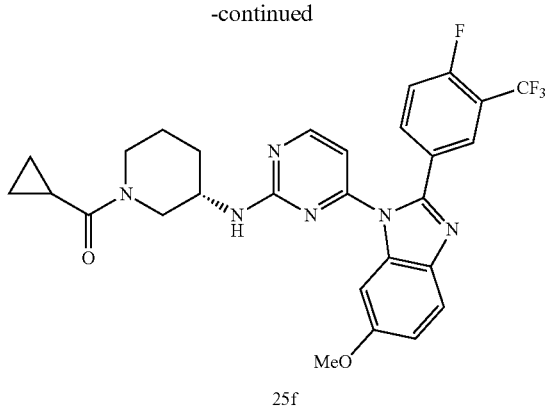

25f

¹H NMR (400 MHz, CDCl₃) δ 8.23 (s, 1H), 7.81 (d, J=32.4 Hz, 1H), 7.58 (m, 2H), 7.16-7.02 (m, 2H), 6.88 (dd, J=8.8, 2.3 Hz, 1H), 6.29 (d, J=32.4 Hz, 1H), 3.96 (s, 1H), 3.72 (s, 3H), 3.61-3.35 (m, 2H), 1.72-1.52 (m, 3H), 1.50-1.33 (m, 2H), 1.07-0.99 (m, 1H), 0.92-0.79 (m, 3H), 0.77-0.59 (m, 3H).

<Example 2-27> (S)-(3-((4-(2-(benzo[d][1,3]dioxole-5-yl)-6-methoxy-1H-benzo[d]imidazole-1-yl)pyrimidin-2-yl)amino)piperidin-1-yl)(cyclopropyl)methanone (25g)

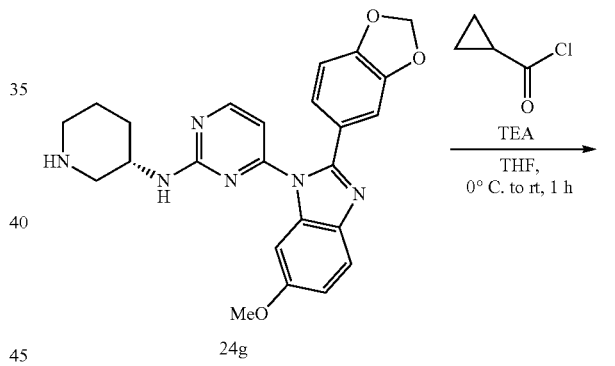

24g

25g

¹H NMR (400 MHz, CDCl₃) δ 8.24 (s, 1H), 7.67 (d, J=8.6 Hz, 1H), 7.24 (s, 1H), 7.02 (m, 2H), 6.94 (dd, J=8.6, 2.0 Hz, 1H), 6.78 (d, J=8.2 Hz, 1H), 6.35-6.14 (m, 1H), 5.98 (s, 2H), 4.16 (s, 1H), 3.81 (s, 3H), 2.01 (m, 1H), 1.74 (s, 2H), 1.66 (m, 2H), 1.29-1.18 (m, 1H), 1.13 (m, 2H), 1.00 (m, 3H), 0.85 (m, 2H), 0.74 (m, 1H).

<Example 2-28> (S)-cyclopropyl(3-((4-(6-hydroxy-2-(naphthalene-2-yl)-1H-benzo[d]imidazole-1-yl)pyrimidin-2-yl)amino)piperidine-1-yl)methanone (26a)

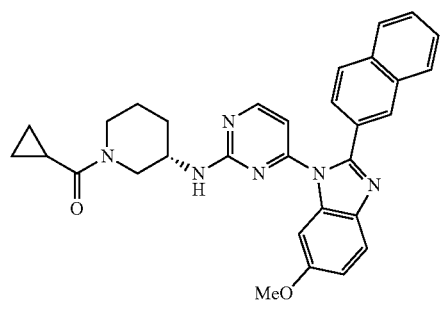

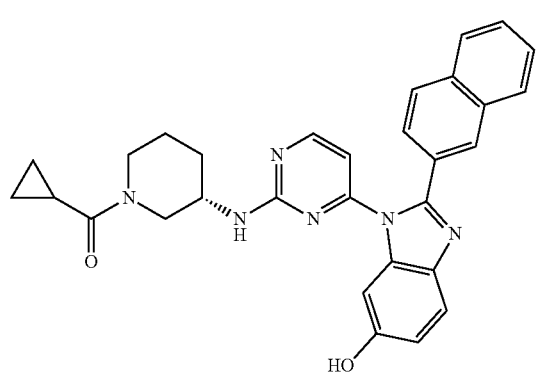

After dissolving Compound 25a (27 mg, 0.053 mmol) in methylene chloride (05.3 ml), BBr₃ (25 μl) was added at −78° C. and stirred for about 1 hour, and then stirred at room temperature for about 2 hours. After confirming the completion of the reaction, methanol was added and quenched. The organic solvent was distilled under reduced pressure, extracted with methylene chloride, and washed with a saturated NaHCO₃ aqueous solution. The extracted organic layer was dried over magnesium sulfate anhydrous, filtered, and the filtrate was distilled under reduced pressure, and the residue was purified by column chromatography (silica gel, methylene chloride:MeOH=20:1) to obtain Compound 26a (25 mg, 93%).

¹H NMR (400 MHz, DMSO-d6) δ 9.52 (s, 1H), 8.3 (m, 2H), 7.92-7.95 (m, H), 7.55-7.61 (m, 5H), 6.84 (dd, J=8.8, 2.0 Hz, 1H), 6.34-6.67 (m, 1H), 3.87-4.39 (m, 3H), 2.80-3.05 (m, 1H), 1.98 (m, 1H), 1.34-1.51 (m, 4H), 0.70-0.85 (m, 4H).

In the same manner as in Example 2-28, the compounds of Examples 2-29 to 2-34 were obtained (Compound 26b, 26c (39 mg, 64%), 26d (3 mg, 18%), 26e (3 mg, 57%), 26f (5 mg, 65%), 26g).

<Example 2-29> (S)-cyclopropyl(3-(4-(6-hydroxy-2-(Quinoline-2-yl)-1H-benzo[d]imidazole-1-yl)pyrimidin-2-ylamino)piperidine-1-yl)methanone (26b)

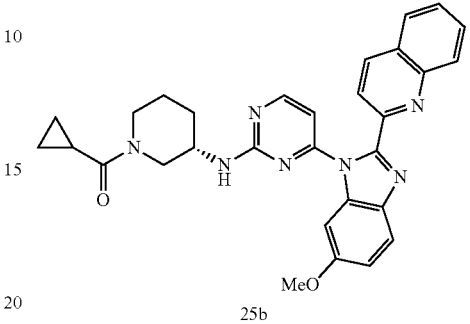

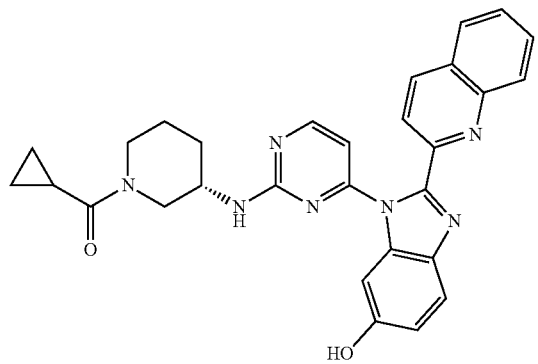

¹H NMR (400 MHz, MeOD) δ 8.45 (m, 2H), 8.35-8.15 (m, 1H), 7.97 (s, 1H), 7.79-7.57 (m, 3H), 7.22 (s, 1H), 6.97 (m, 1H), 6.77 (s, 1H), 4.07 (m, 2H), 3.25-3.08 (s, 1H), 2.69 (m, 1H), 2.08-1.96 (m, 1H), 1.87-1.49 (m, 4H), 1.29 (m, 3H), 0.89 (m, 3H), 0.65 (m, 1H).

<Example 2-30> (S)-cyclopropyl(3-((4-(2-(2,3-dihydrobenzo[b][1,4]dioxin-6-yl)-6-hydroxy-1H-benzo[d]imidazole-1-yl)pyrimidin-2-yl)amino)piperidine-1-yl)methanone (26c)

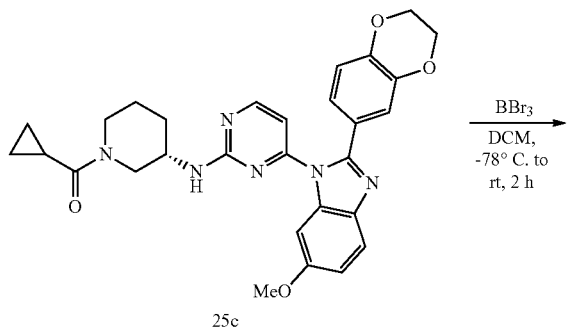

-continued

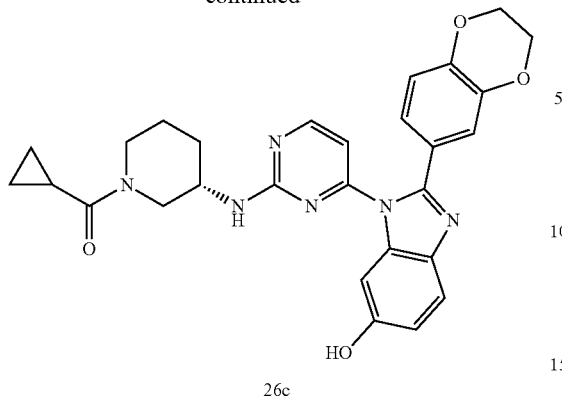

26c

¹H NMR (400 MHz, DMSO) δ 9.47 (s, 1H), 8.51-8.28 (m, 1H), 7.80-7.62 (m, 1H), 7.53 (d, J=8.6 Hz, 1H), 7.01 (m, 1H), 6.90 (m, 2H), 6.79 (dd, J=8.6, 2.1 Hz, 1H), 4.26 (m, 4H), 4.19-4.07 (m, 1H), 3.86 (s, br, 1H), 3.52 (m, 1H), 3.05 (m, 1H), 2.63 (m, 1H), 1.96 (m, 1H), 1.81 (m, 2H), 1.64-1.35 (m, 2H), 1.21 (m, 1H), 0.83 (m, 3H), 0.58-0.01 (m, 2H).

<Example 2-31> (S)-(3-((4-(2-(benzofuran-5-yl)-6-hydroxy-1H-benzo[d]imidazole-1-yl)pyrimidin-2-yl)amino)piperidine-1-yl)(cyclopropyl)methanone (26d)

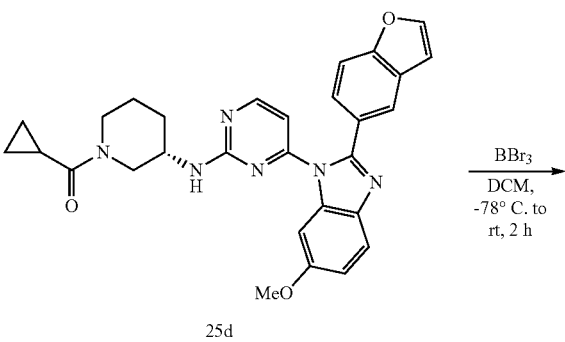

25d

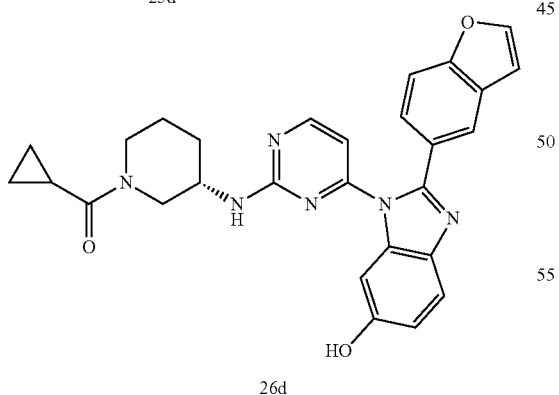

26d

¹H NMR (400 MHz, CD₃OD) δ 8.35 (s, 1H), 7.84 (m, 2H), 7.56 (dd, J=8.4, 3.8 Hz, 2H), 7.42 (d, J=8.1 Hz, 1H), 7.27-7.14 (m, 1H), 7.04 (dd, J=14.9, 8.4 Hz, 1H), 6.89 (d, J=8.2 Hz, 2H), 4.22 (s, br, 1H), 4.02 (s, 1H), 3.17 (m, 1H), 2.84 (m, 2H), 2.10-1.96 (m, 2H), 1.81 (m, 2H), 1.56 (m, 2H), 0.88 (m, 5H).

<Example 2-32> (S)-cyclopropyl(3-((4-(2-(3,4-dichlorophenyl)-6-hydroxy-1H-benzo[d]imidazole-1-yl)pyrimidin-2-yl)amino)piperidine-1-yl)methanone (26e)

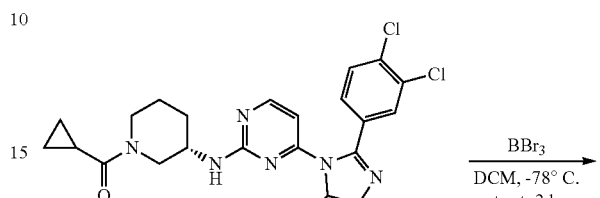

25e

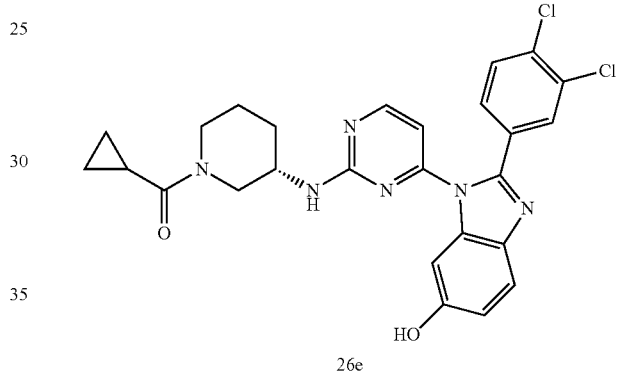

26e

¹H NMR (400 MHz, CD₃OD) δ 8.39 (d, J=57.2 Hz, 1H), 7.75 (s, 1H), 7.58 (t, J=8.2 Hz, 2H), 7.37 (d, J=6.7 Hz, 1H), 7.05 (s, 1H), 6.91 (d, J=8.8 Hz, 1H), 6.42 (d, J=5.3 Hz, 1H), 4.24 (d, J=12.4 Hz, 1H), 3.60 (s, 1H), 3.27-3.13 (m, 1H), 3.09-2.61 (m, 2H), 2.01 (s, 1H), 1.92-1.50 (m, 5H), 1.02-0.81 (m, 3H), 0.66-0.22 (m, 2H).

<Example 2-33> (S)-cyclopropyl(3-((4-(2-(4-fluoro-3-(trifluoromethyl)phenyl)-6-hydroxy-1H-benzo[d]imidazole-1-yl)pyrimidin-2-yl)amino)piperidine-1-yl)methanone (26f)

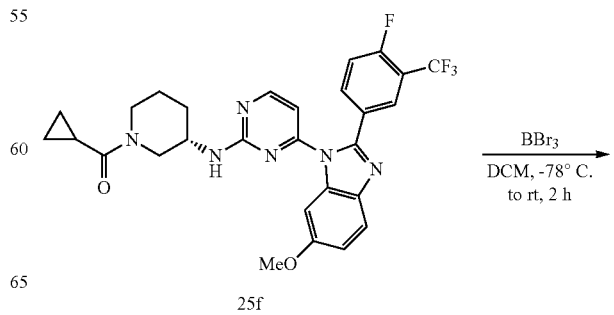

25f

III. Synthesis of benzimidazol-5,6-diol Derivatives

<Preparation Example 3-1>
4,5-dimethoxybezene-1,2-diamine (28)

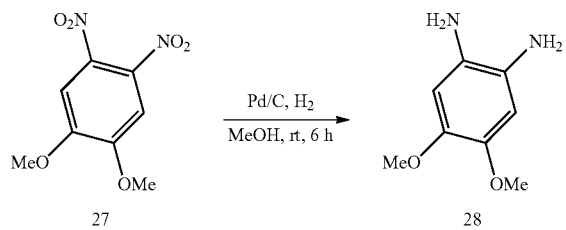 [SMILES: COc1cc([N+](=O)[O-])c([N+](=O)[O-])cc1OC ; COc1cc(N)c(N)cc1OC]

Compound 27 (5 g, 21.9 mmol) was dissolved in methanol (147 ml), then 10% Pd/C (639 mg) was added and stirred at room temperature for 6 hours in the presence of hydrogen gas. After the reaction was completed, the mixture was filtered through celite and the filtrate was distilled under reduced pressure. Compound 28 was obtained from the residue without any purification.

as a dark brown solid (99%); $^1$H NMR (400 MHz, DMSO) δ 6.26 (s, 2H), 4.11 (s, 4H), 3.58 (s, 6H).; LRMS (ESI) calcd for $C_8H_{12}N_2O_2$ [M+H]+: 170, Found 170.

<Preparation Example 3-2> 5,6-dimethoxy-2-(naph-thalenen-2-yl)-1H-benzo[d]imidazole etc. (Compounds 29a to 29e)

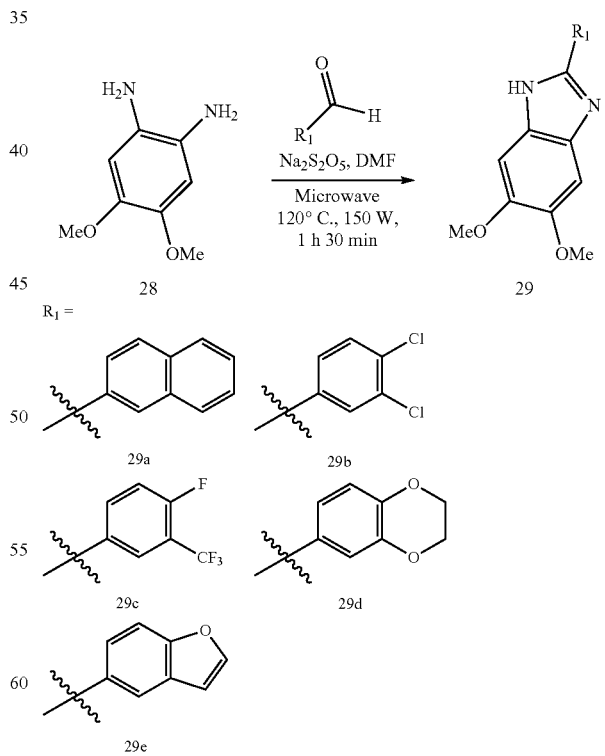

Compound 28 (2.97 mmol), R$_1$CHO (32.7 mmol) and Na$_2$S$_2$O$_5$ (148.5 mmol) were dissolved in DMF (29.7 ml) and stirred at 120° C., 150 W for 1 hour 30 minutes in

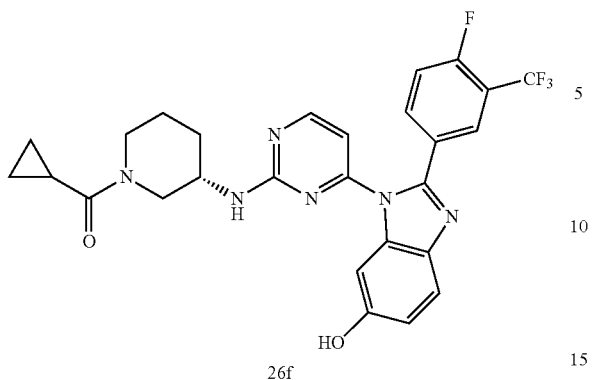

26f $^1$H NMR (400 MHz, CD$_3$OD) δ 8.37 (s, 1H), 7.91 (d, J=4.7 Hz, 1H), 7.77 (s, 1H), 7.67-7.54 (m, 1H), 7.42 (m, 1H), 7.02 (s, 1H), 6.90 (d, J=8.7 Hz, 1H), 6.37 (s, 1H), 4.14 (s, 1H), 3.59 (s, 1H), 2.15-1.95 (m, 2H), 1.59 (m, 3H), 1.28 (m, 4H), 0.93-0.57 (m, 4H), 0.29 (m, 1H).

<Example 2-34> (S)-(3-(4-(2-([1,3]dioxolo[4,5-b]pyridin-5-yl)-6-hydroxy-1H-benzo[d]imidazole-1-yl)pyrimidin-2-ylamino)piperidine-1-yl)(cyclopropyl)methanone (26g)

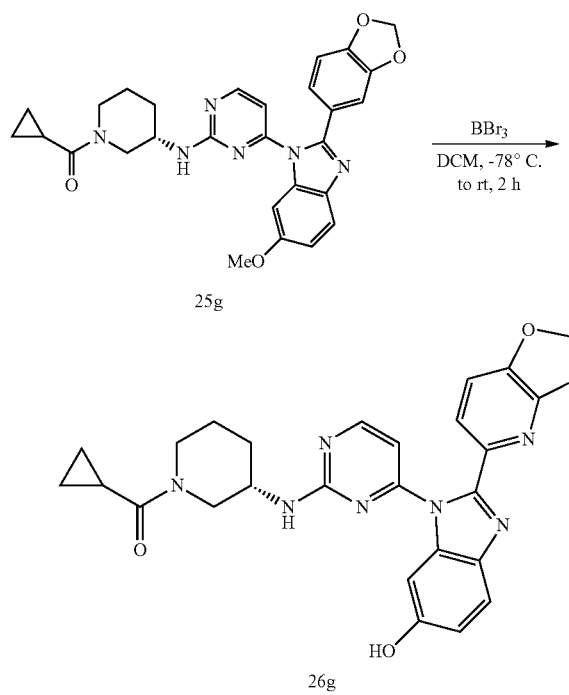

$^1$H NMR (400 MHz, DMSO) δ 9.34 (d, J=46.0 Hz, 2H), 8.48-8.23 (m, 1H), 7.70 (d, J=32.8 Hz, 1H), 7.48 (d, J=8.6 Hz, 1H), 6.96 (s, 1H), 6.76 (d, J=6.1 Hz, 2H), 4.19 (d, J=11.6 Hz, 1H), 3.88 (d, J=68.9 Hz, 1H), 2.87 (d, J=96.9 Hz, 1H), 2.11-1.75 (m, 3H), 1.74-1.37 (m, 3H), 1.20 (d, J=23.5 Hz, 2H), 0.88-0.63 (m, 1H), 0.52 (d, J=37.8 Hz, 1H), 0.14 (d, J=90.2 Hz, 1H).

microwave. After confirming the completion of the reaction, the solvent was poured into iced water to precipitate. After the precipitated reaction was filtered, the filtrate was distilled under reduced pressure, and the crude product was purified by flash column chromatography on silica gel using a mobile phase of EA:HEX (3:1) to obtain Compounds 29a to 29e.

Compound 29a (5,6-dimethoxy-2-(naphthalene-2-yl)-1H-benzo[d]imidazole)

as a yellow solid (50%); $^1$H NMR (400 MHz, DMSO) δ 12.79 (s, 1H), 8.61 (s, 1H), 8.25 (dd, J=8.6, 1.7 Hz, 1H), 8.04 (d, J=8.7 Hz, 1H), 8.02-7.94 (m, 2H), 7.61-7.53 (m, 2H), 7.14 (d, J=76.5 Hz, 2H), 3.83 (s, 6H).; LRMS (ESI) calcd for $C_{19}H_{16}N_2O_2$ [M+H]+: 305, Found 305.

Compound 29b (2-(3,4-dichlorophenyl)-5,6-dimethoxy-1H-benzo[d]imidazole)

as a yellow solid (56%); $^1$H NMR (400 MHz, CDCl$_3$) δ 9.15 (s, 1H), 8.05 (d, J=1.5 Hz, 1H), 7.82 (dd, J=8.4, 1.6 Hz, 1H), 7.35 (d, J=8.4 Hz, 1H), 7.02 (s, 2H), 3.80 (s, 6H).; LRMS (ESI) calcd for $C_{15}H_{12}Cl_2N_2O_2$ [M+H]+: 324, Found 324.

Compound 29c (2-(4-fluoro-3-(trifluoromethyl)phenyl)-5,6-dimethoxy-1H-benzo[d]imidazole)

as a yellow solid (65%); $^1$H NMR (400 MHz, CDCl$_3$) δ 8.23-8.16 (m, 2H), 7.15 (m, 1H), 7.09 (s, 2H), 3.84 (s, 6H).; LRMS (ESI) calcd for $C_{16}H_{12}F_4N_2O_2$[M+H]+: 341, Found 341.

Compound 29d (2-(2,3-dihydrobenzo[b][1,4]dioxin-6-yl)-5,6-dimethoxy-1H-benzo[d]imidazole)

as a white solid (45%); $^1$H NMR (400 MHz, CDCl$_3$) 7.76 (d, J=8.9 Hz, 1H), 7.30 (d, J=2.3 Hz, 1H), 7.13 (d, J=2.1 Hz, 1H), 7.00-6.93 (m, 2H), 4.28 (m, 2H), 4.27-4.23 (m, 2H), 3.87 (s, 6H).; LRMS (ESI) calcd for $C_{17}H_{16}N_2O_4$ [M+H]+: 313, Found 313.

Compound 29e (2-(benzofuran-5-yl)-5,6-dimethoxy-1H-benzo[d]imidazole)

as a yellow solid (67%); $^1$H NMR (400 MHz, CDCl$_3$) δ 8.34 (s, 1H), 8.06 (d, J=8.3 Hz, 1H), 7.58 (s, 1H), 7.45 (d, J=8.5 Hz, 1H), 6.91 (s, 2H), 6.59 (s, 1H), 3.66 (s, 6H).; LRMS (ESI) calcd for $C_{17}H_{14}N_2O_3$ [M+H]+: 295, Found 295.

<Preparation Example 3-3> 5,6-dimethoxy-1-(2-(methylthio)pyrimidin-4-yl)-2-(naphthalene-2-yl)-1H-benzo[d]imidazole etc. (Compounds 30a to 30e)

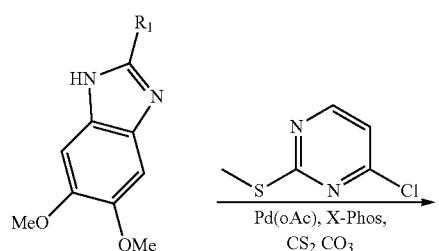

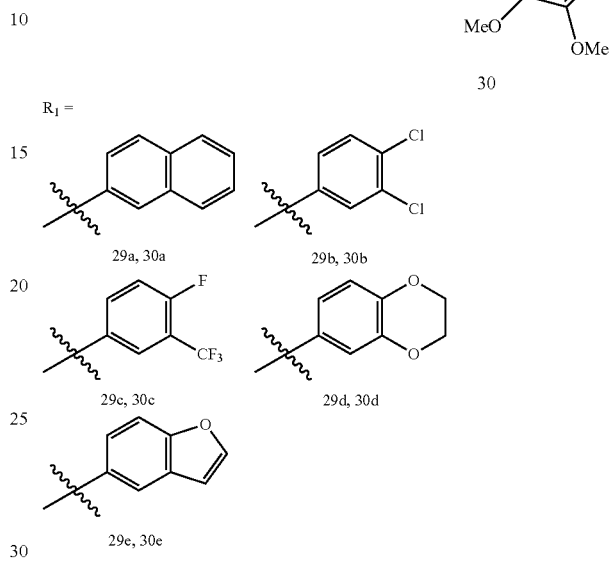

Compound 29a to 29e (1.3 mmol), 4-chloro-2-(methylthio)pyrimidine (320 mg, 1.3 mmol), palladium (II) acetate (Pd(oAc)$_2$) (88 mg, 0.13 mmol), X-Phos (62 mg, 0.13 mmol), and CS$_2$CO$_3$ were purged with nitrogen and then mixed by addition of toluene (13 mL). After sonication under nitrogen for 5 minutes, the mixture was heated to 130° C. under nitrogen and stirred at 130° C. for 3 hours without nitrogen. After cooling to ambient temperature, the reaction mixture is filtered through a celitepad, the solvent is removed in vacuo and purified by flash column chromatography on silica gel using a mobile phase of DCM:MEOH (40:1) to obtain Compound 30a to 30e.

Compound 30a (5,6-dimethoxy-1-(2-(methylthio)pyrimidin-4-yl)-2-(naphthalene-2-yl)-1H-benzo[d]imidazole)

as a yellow solid (27%); $^1$H NMR (400 MHz, CDCl$_3$) δ 8.37 (d, J=5.4 Hz, 1H), 8.22 (s, 1H), 7.88-7.83 (m, 3H), 7.59-7.49 (m, 4H), 7.41 (s, 1H), 6.54 (d, J=5.4 Hz, 1H), 3.99 (s, 3H), 3.96 (s, 3H), 2.56 (s, 3H).; LRMS (ESI) calcd for $C_{24}H_{20}N_4O_2S$ [M+H]+: 429, Found 429.

Compound 30b (2-(3,4-dichlorophenyl)-5,6-dimethoxy-1-(2-(methylthio)pyrimidin-4-yl)-1H-benzo[d]imidazole)

as a yellow solid (35%); $^1$H NMR (400 MHz, CDCl$_3$) δ 8.47 (d, J=5.4 Hz, 1H), 7.73 (d, J=2.0 Hz, 1H), 7.41 (d, J=8.3 Hz, 1H), 7.35 (s, 1H), 7.24 (dd, J=8.5, 2.2 Hz, 2H), 6.57 (d, J=5.4 Hz, 1H), 3.92 (s, 3H), 3.89 (s, 3H), 2.50 (s, 3H).; LRMS (ESI) calcd for $C_{20}H_{16}Cl_2N_4O_2S$ [M+H]+: 448, Found 448.

Compound 30c 2-(4-fluoro-3-(trifluoromethyl)phenyl)-5,6-dimethoxy-1-(2-(methylthio)pyrimidin-4-yl)-1H-benzo[d]imidazole as a yellow solid (37%); $^1$H NMR (400 MHz, CDCl$_3$) δ 8.52 (d, J=5.3 Hz, 1H), 7.92 (d, J=5.0 Hz, 1H), 7.67-7.60 (m, 1H), 7.30 (d, J=6.3 Hz, 2H), 7.21 (t, J=9.2 Hz, 1H), 6.64 (d, J=5.3 Hz, 1H), 3.92 (d, J=9.7 Hz, 6H), 2.46 (s, 3H).; LRMS (ESI) calcd for C$_{21}$H$_{16}$F$_4$N$_4$O$_2$S [M+H]+: 465, Found 465.

Compound 30d (2-(2,3-dihydrobenzo[b][1,4]dioxin-6-yl)-5,6-dimethoxy-1-(2-(methylthio)pyrimidin-4-yl)-1H-benzo[d]imidazole)

as a yellow solid (42%); $^1$H NMR (400 MHz, CDCl$_3$) δ 8.41 (d, J=5.4 Hz, 1H), 7.44 (s, 1H), 7.30 (s, 1H), 7.08 (d, J=2.0 Hz, 1H), 6.96 (dd, J=8.4, 2.1 Hz, 1H), 6.84 (d, J=8.4 Hz, 1H), 6.54 (d, J=5.4 Hz, 1H), 4.29-4.25 (m, 2H), 4.23 (dd, J=3.7, 1.5 Hz, 2H), 3.93 (s, 3H), 3.90 (s, 3H), 2.57 (s, 3H).; LRMS (ESI) calcd for C$_{22}$H$_{20}$N$_4$O$_4$S [M+H]+: 437, Found 437.

Compound 30e (2-(benzofuran-5-yl)-5,6-dioxy-1-(2-(methylthio)pyrimidin-4-yl)-1H-benzo[d]imidazole)

as a yellow solid (58%); $^1$H NMR (400 MHz, DMSO) δ 9.07 (d, J=5.5 Hz, 1H), 8.15 (d, J=2.4 Hz, 1H), 8.03 (d, J=1.7 Hz, 1H), 8.01 (d, J=9.1 Hz, 1H), 7.76 (d, J=8.6 Hz, 1H), 7.56 (dd, J=8.6, 1.7 Hz, 1H), 7.43 (m, 2H), 7.16 (dd, J=9.1, 2.4 Hz, 1H), 7.09 (d, J=1.5 Hz, 1H), 3.88 (s, 6H), 3.36 (s, 3H).; LRMS (ESI) calcd for C$_{22}$H$_{18}$N$_4$O$_5$S [M+H]+: 451, Found 451.

<Preparation Example 3-4> 5,6-dimethoxy-1-(2-(methylsulfonyl)pyrimidin-4-yl)-2-(naphthalene-2-yl)-1H-benzo[d]imidazole etc. (Compound 31a-31e)

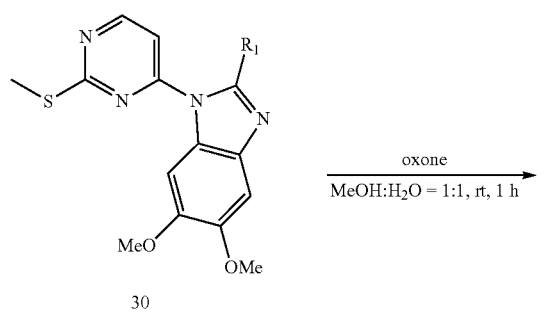

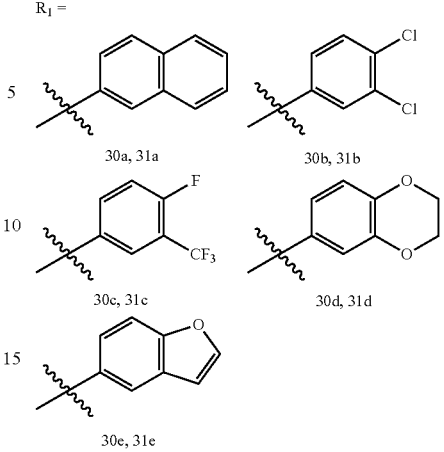

Compound 30a to 30e (1 mmol) and potassium peroxomonosulfate (3.8 g) were dissolved in a mixed solvent of MeOH:H$_2$O=1:1 (5 ml) and stirred at room temperature for 1 hour. When Compound 30a to 30e were disappeared from TLC, methanol was concentrated in vacuo. Water was added to the mixture, diluted and stirred until the product separated to a solid. The solid product was filtered off and washed with water and then the crude product was crystallized to obtain Compound 31a to 31e.

Compound 31a (5,6-dimethoxy-1-(2-(methylsulfonyl)pyrimidin-4-yl)-2-(naphthalene-2-yl)-1H-benzo[d]imidazole)

as a brown solid (68%); $^1$H NMR (400 MHz, DMSO) δ 9.03 (d, J=5.6 Hz, 1H), 8.29 (s, 1H), 8.04-7.99 (m, 3H), 7.80 (s, 1H), 7.64 (m, 3H), 7.47 (d, J=5.6 Hz, 1H), 7.42 (s, 1H), 3.89 (s, 3H), 3.86 (s, 3H), 3.35 (s, 3H).; LRMS (ESI) calcd for C$_{24}$H$_{20}$N$_4$O$_4$S [M+H]+: 461, Found 461.

Compound 31b (2-(3,4-dichlorophenyl)-5,6-dimethoxy-1-(2-(methylsulfonyl)pyrimidin-4-yl)-1H-benzo[d]imidazole)

as a white solid (60%); $^1$H NMR (400 MHz, DMSO) δ 9.12 (d, J=5.5 Hz, 1H), 7.94 (d, J=2.0 Hz, 1H), 7.73-7.69 (m, 2H), 7.61 (d, J=5.5 Hz, 1H), 7.52-7.49 (m, 1H), 7.38 (s, 1H), 3.86 (s, 3H), 3.83 (s, 3H), 3.39 (s, 3H).; LRMS (ESI) calcd for C$_{20}$H$_{16}$C$_{12}$N$_4$O$_4$S [M+H]+: 480, Found 480.

Compound 31c (2-(4-fluoro-3-(trifluoromethyl)phenyl)-5,6-dimethoxy-1-(2-(methylsulfonyl)pyrimidin-4-yl)-1H-benzo[d]imidazole)

as a white solid (70%); 1H NMR (400 MHz, DMSO) δ 9.11 (d, J=5.6 Hz, 1H), 8.07 (dd, J=6.7, 1.9 Hz, 1H), 7.88 (m, 1H), 7.72 (d, J=12.8 Hz, 1H), 7.63 (d, J=5.6 Hz, 1H), 7.59 (d, J=10.3 Hz, 1H), 7.41 (s, 1H), 3.85 (d, J=8.6 Hz, 6H), 3.16 (s, 3H).; LRMS (ESI) calcd for C$_{21}$H$_{16}$F$_4$N$_4$O$_4$S [M+H]+: 497, Found 497.

Compound 31d (2-(2,3-dihydrobenzo[b][1,4]dioxin-6-yl)-5,6-dimethoxy-1-(2-(methylsulfonyl)pyrimidin-4-yl)-1H-benzo[d]imidazole)

as a white solid (65%); $^1$H NMR (400 MHz, DMSO) δ 9.12 (d, J=5.5 Hz, 1H), 7.93 (d, J=9.0 Hz, 1H), 7.51 (d, J=5.5

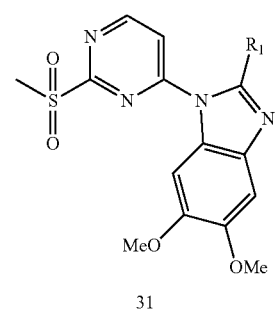

Hz, 1H), 7.37 (d, J=2.4 Hz, 1H), 7.19 (d, J=2.0 Hz, 1H), 7.10 (dd, J=9.0, 2.4 Hz, 1H), 7.02 (dd, J=8.4, 2.0 Hz, 1H), 6.97 (d, J=8.4 Hz, 1H), 4.33 (d, J=4.7 Hz, 2H), 4.30 (d, J=4.7 Hz, 2H), 3.86 (s, 6H), 3.41 (s, 3H).; LRMS (ESI) calcd for C$_{22}$H$_{20}$N$_4$O$_6$S [M+H]+: 469, Found 469.

Compound 31e (2-(benzofuran-5-yl)-5,6-dimethoxy-1-(2-(methylsulfonyl)pyrimidin-4-yl)-1H-benzo[d]imidazole)

as a white solid (70%); $^1$H NMR (400 MHz, CDCl$_3$) δ 8.33 (d, J=5.4 Hz, 1H), 7.83 (d, J=1.4 Hz, 1H), 7.66 (d, J=2.2 Hz, 1H), 7.50 (m, 2H), 7.41 (dd, J=8.6, 1.8 Hz, 1H), 7.32 (s, 1H), 6.77 (dd, J=2.2, 0.9 Hz, 1H), 6.43 (d, J=5.4 Hz, 1H), 3.94 (d, J=7.7 Hz, 6H), 2.55 (s, 3H).; LRMS (ESI) calcd for C$_{22}$H$_{18}$N$_4$O$_3$S [M+H]+: 419, Found 419.

<Preparation Example 3-5> tert-butyl 3-(4-(5,6-dimethoxy-2-(naphthalene-2-yl)-1H-benzo[d]imidazole-1-yl)pyrimidin-2-ylamino)piperidine-1-carboxylate etc. (Compound 32a-32e)

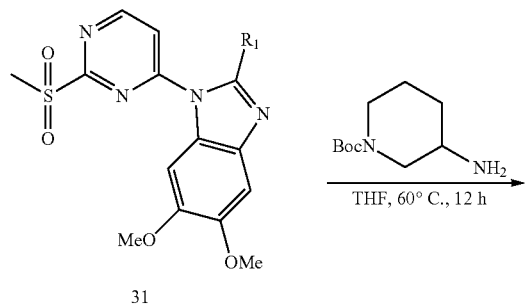

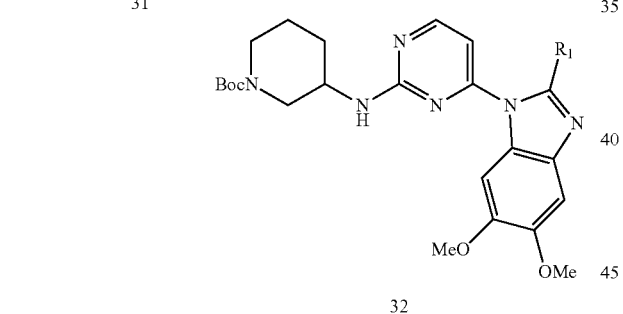

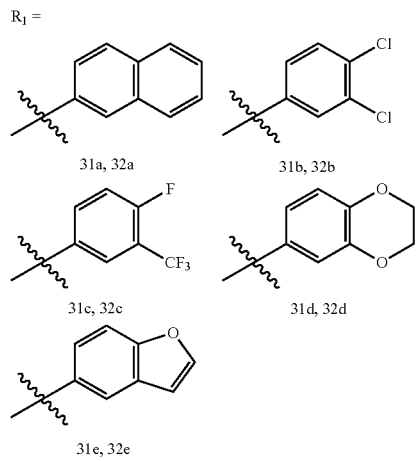

Compound 31a to 31e (1 mmol) and (S)-tert-butyl-3-aminopiperidine-1-carboxylate (2 mmol) were dissolved in THF (10 ml) and stirred at 60° C. for 12 hours. After Compound 31a to 31e disappeared in TLC, the reaction mixture was cooled to ambient temperature and concentrated in vacuo. The crude product was purified by flash column chromatography on silica gel using a mobile phase of HEX:EA (1:1) to obtain Compounds 32a to 32e.

Compound 32a (tert-butyl 3-(4-(5,6-dimethoxy-2-(naphthalene-2-yl)-1H-benzo[d]imidazole-1-yl)pyrimidin-2-ylamino)piperidine-1-carboxylate)

as a yellow solid (37%); $^1$H NMR (400 MHz, MeOD) δ 8.28 (s, 1H), 8.13 (s, 1H), 7.93-7.88 (m, 3H), 7.57 (m, 3H), 7.47 (s, 1H), 7.32 (s, 1H), 6.52 (s, 1H), 3.94 (s, 3H), 3.92 (s, 3H), 3.69-3.58 (s, 1H), 3.20 (m, 1H), 2.79 (m, 2H), 1.45 (s, 9H), 1.12 (m, 4H), 0.91 (m, 2H).; LRMS (ESI) calcd for C$_{33}$H$_{36}$N$_6$O$_4$ [M+H]+: 581, Found 581.

Compound 32b (tert-butyl 3-(4-(2-(3,4-dichlorophenyl)-5,6-dimethoxy-1H-benzo[d]imidazole-1-yl)pyrimidin-2-ylamino)piperidine-1-carboxylate)

as a yellow solid (51%); $^1$H NMR (400 MHz, CDCl$_3$) δ 8.31 (s, 1H), 7.77 (s, 1H), 7.44 (d, J=8.3 Hz, 1H), 7.32 (dd, J=7.5, 2.9 Hz, 2H), 7.28-7.24 (m, 1H), 6.31 (s, 1H), 3.96 (s, 3H), 3.92 (s, 3H), 3.84-3.59 (m, 2H), 3.32 (s, 2H), 1.71 (m, 2H), 1.59-1.47 (m, 2H), 1.42 (m, 8H), 0.90 (m, 1H).; LRMS (ESI) calcd for C$_{29}$H$_{32}$C$_{12}$N$_6$O$_4$S [M+H]+: 617, Found 617.

Compound 32c (tert-butyl 3-(4-(2-(4-fluoro-3-(trifluoromethyl)phenyl)-5,6-dimethoxy-1H-benzo[d]imidazole-1-yl)pyrimidin-2-ylamino)piperidine-1-carboxylate)

as a yellow solid (53%); $^1$H NMR (400 MHz, CDCl$_3$) δ 8.33 (s, 1H), 7.93 (d, J=4.9 Hz, 1H), 7.67 (s, 1H), 7.31 (s, 1H), 7.21 (m, 2H), 6.34 (d, J=3.4 Hz, 1H), 3.93 (d, J=15.5 Hz, 6H), 3.71-3.57 (s, 1H), 3.53-3.36 (m, 1H), 3.30 (m, 2H), 1.69 (m, 2H), 1.46-1.42 (m, 3H), 1.40 (s, 9H), 1.22 (m, 1H).; LRMS (ESI) calcd for C$_{30}$H$_{32}$F$_4$N$_6$O$_4$[M+H]+: 599, Found 599.

Compound 32d (tert-butyl 3-(4-(2-(2,3-dihydrobenzo[b][1,4]dioxin-6-yl)-5,6-dimethoxy-1H-benzo[d]imidazole-1-yl)pyrimidin-2-ylamino)piperidine-1-carboxylate)

as a yellow solid (57%); $^1$H NMR (400 MHz, CDCl$_3$) δ8.23 (d, J=5.0 Hz, 1H), 7.69 (d, J=8.5 Hz, 1H), 7.31 (s, 1H), 7.14 (s, 1H), 7.04 (d, J=7.9 Hz, 1H), 6.96 (d, J=2.0 Hz, 1H), 6.85 (d, J=8.4 Hz, 1H), 6.23 (s, 1H), 4.28 (d, J=4.9 Hz, 2H), 4.24 (d, J=4.9 Hz, 2H), 3.86 (s, 6H), 3.78 (s, 1H), 3.45 (m, 2H), 3.37 (m, 1H), 1.66 (m, 2H), 1.53 (m, 2H), 1.43 (s, 9H), 1.23 (m, 2H); LRMS (ESI) calcd for C$_{31}$H$_{36}$N$_6$O$_6$ [M+H]+: 589, Found 589.

Compound 32e (tert-butyl 3-(4-(2-(benzofuran-5-yl)-5,6-dimethoxy-1H-benzo[d]imidazole-1-yl)pyrimidin-2-ylamino)piperidine-1-carboxylate)

as a yellow solid (65%); $^1$H NMR (400 MHz, CDCl$_3$) δ 8.33 (d, J=5.4 Hz, 1H), 7.83 (d, J=1.4 Hz, 1H), 7.66 (d, J=2.2 Hz, 1H), 7.50 (m, 2H), 7.41 (dd, J=8.6, 1.8 Hz, 1H), 7.32 (s, 1H), 6.77 (dd, J=2.2, 0.9 Hz, 1H), 6.43 (d, J=5.4 Hz, 1H), 3.94 (d, J=7.7 Hz, 6H), 2.55 (s, 3H).; LRMS (ESI) calcd for C$_{22}$H$_{18}$N$_4$O$_5$S [M+H]+: 451, Found 451.

<Preparation Example 3-6> 4-(5,6-dimethoxy-2-(naphthalene-2-yl)-1H-benzo[d]imidazole-1-yl)-N-(piperidine-3-yl)pyrimidin-2-amine etc. (Compounds 33a-33e)

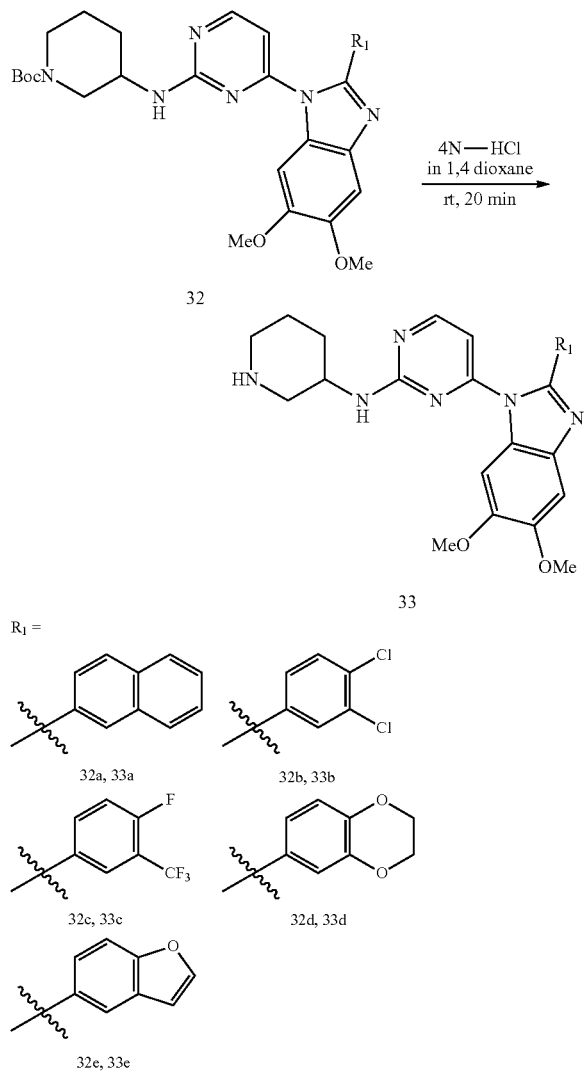

Compound 32a to 32e (0.033 mmol) were dissolved in 1,4-dioxane (0.33 ml) and 4 M–HCl (0.17 ml) containing 1,4-dioxane was treated at room temperature. The reaction mixture was stirred at room temperature for 20 minutes, the mixture was diluted with ether and then stirred until the product separated to a solid. The solid product was filtered off and washed with ether followed by hexane. The crude product was then crystallized to obtain Compound 33a to 33e.

Compound 33a (4-(5,6-dimethoxy-2-(naphthalene-2-yl)-1H-benzo[d]imidazole-1-yl)-N-(piperidine-3-yl)pyrimidin-2-amine)

as a white solid (69%); $^1$H NMR (400 MHz, MeOD) δ 8.38 (s, 1H), 8.10 (s, 1H), 7.95-7.86 (m, 3H), 7.61-7.52 (m, 3H), 7.32 (s, 2H), 6.74 (s, 1H), 3.94 (s, 3H), 3.92 (s, 3H), 3.73-3.46 (s, 1H), 3.19-2.92 (m, 2H), 2.68 (m, 2H), 1.52 (m, 2H), 1.29 (m, 2H), 0.98-0.80 (m, 2H).; LRMS (ESI) calcd for $C_{28}H_{28}N_6O_2$ [M+H]+: 481, Found 481.

Compound 33b (4-(2-(3,4-dichlorophenyl)-5,6-dimethoxy-1H-benzo[d]imidazole-1-yl)-N-(piperidine-3-yl)pyrimidin-2-amine)

as a yellow solid (78%); $^1$H NMR (400 MHz, MeOD) δ 8.63 (s, 1H), 7.98 (s, 1H), 7.81 (d, J=7.6 Hz, 1H), 7.62 (s, 1H), 7.41 (m, 2H), 6.90 (s, 1H), 4.32 (s, 1H), 4.00 (s, 3H), 3.96 (s, 3H), 3.68-3.50 (m, 1H), 3.37 (m, 1H), 3.00 (m, 2H), 2.03 (m, 2H), 1.79 (m, 2H), 1.64 (m, 1H); LRMS (ESI) calcd for $C_{24}H_{24}Cl_2N_6O_2$ [M+H]+: 500, Found 500.

Compound 33c (4-(2-(4-fluoro-3-(trifluoromethyl)phenyl)-5,6-dimethoxy-1H-benzo[d]imidazole-1-yl)-N-(piperidine-3-yl)pyrimidin-2-amine)

as a white solid (80%); $^1$H NMR (400 MHz, CDCl$_3$) δ 8.43 (d, J=21.5 Hz, 1H), 7.93-7.76 (m, 2H), 7.39 (s, 1H), 7.31 (m, 1H), 7.17 (s, 1H), 6.56 (s, 1H), 3.98 (s, 3H), 3.93 (s, 3H), 3.70 (s, 1H), 3.46 (m, 1H), 3.33 (s, 1H), 2.12-1.87 (m, 1H), 1.65 (m, 4H), 1.24 (m, 2H), 0.87 (m, 1H).; LRMS (ESI) calcd for $C_{25}H_{24}F_4N_6O_2$[M+H]+: 517, Found 517.

Compound 33d (4-(2-(2,3-dihydrobenzo[b][1,4]dioxin-6-yl)-5,6-dimethoxy-1H-benzo[d]imidazole-1-yl)-N-(piperidine-3-yl)pyrimidin-2-amine)

as a yellow solid (86%); $^1$H NMR (400 MHz, MeOD) δ 8.49 (s, 1H), 7.30 (d, J=52.5 Hz, 2H), 7.10 (s, 1H), 7.03 (s, 1H), 6.94 (d, J=6.7 Hz, 1H), 6.63 (d, J=131.7 Hz, 1H), 4.30 (d, J=8.5 Hz, 4H), 3.93 (d, J=10.6 Hz, 6H), 3.67 (s, 1H), 3.43-3.26 (m, 4H), 3.03 (s, 2H), 2.19-1.96 (m, 2H), 1.90-1.71 (m, 2H), 1.28 (s, 1H).; LRMS (ESI) calcd for $C_{26}H_{28}N_6O_4$ [M+H]+: 489, Found 489.

Compound 33e (4-(2-(benzofuran-5-yl)-5,6-dimethoxy-1H-benzo[d]imidazole-1-yl)-N-(piperidine-3-yl)pyrimidin-2-amine)

as a yellow solid (89%); $^1$H NMR (400 MHz, DMSO) δ 8.51 (s, 1H), 8.18 (s, 1H), 8.08 (d, J=13.9 Hz, 1H), 7.82 (d, J=8.6 Hz, 1H), 7.57 (d, J=8.6 Hz, 1H), 7.41 (s, 1H), 7.38 (s, 1H), 7.15 (s, 1H), 6.62 (s, 1H), 3.97 (s, 1H), 3.90 (d, J=7.4 Hz, 6H), 3.23-2.99 (m, 2H), 2.74 (s, 3H), 2.02-1.70 (m, 2H), 1.47 (d, J=87.5, 3H).; LRMS (ESI) calcd for $C_{26}H_{26}N_6O_3$ [M+H]+: 471, Found 471.

<Preparation Example 3-7> (R)-cyclopropyl(3-(4-(5,6-dimethoxy-2-(naphthalene-2-yl)-1H-benzo[d]imidazole-1-yl)pyrimidin-2-ylamino)piperidine-1-yl)methanone etc. (34a to 34e)

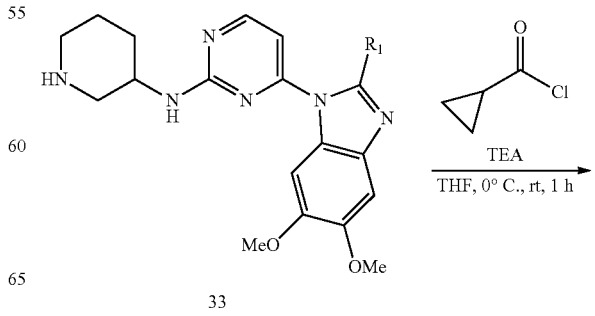

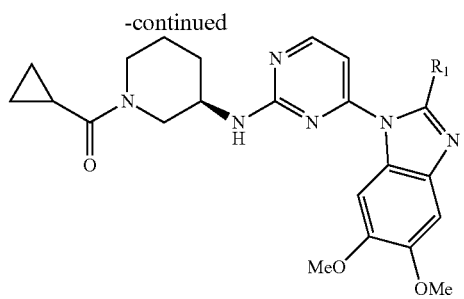

34

R₁ =

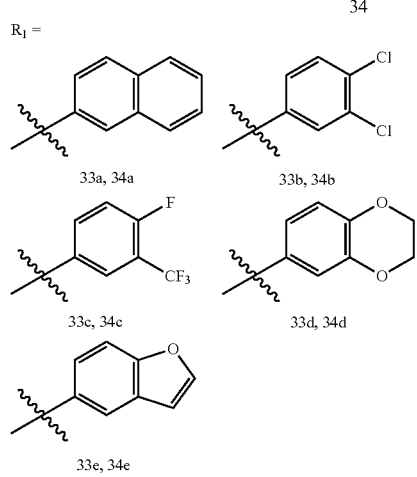

Compound 33a to 33e (0.024 mmol) were dissolved in THF (0.24 ml) and cooled to 0° C., then treated with TEA (5 μL, 0.038 mmol). The mixture was added cyclopropanecarbonyl chloride (6.5 mg, 0.024 mmol) at 0° C., raised to room temperature, and stirred for 1 hour. The reaction mixture was concentrated in vacuo, diluted with methylene chloride and washed with water and saturated aqueous sodium chloride solution. The organic layer was dried over sodium sulfate, filtered, and the filtrate was distilled under reduced pressure, and the residue was purified by column chromatography (silica gel, DCM:MEOH 40:1) to obtain Compound 34a to 34e.

Compound 34a ((R)-cyclopropyl(3-(4-(5,6-dimethoxy-2-(naphthalene-2-yl)-1H-benzo[d]imidazole-1-yl)pyrimidin-2-ylamino)piperidine-1-yl)methanone)

as a yellow solid (74%); $^1$H NMR (400 MHz, MeOD) δ 8.33 (d, J=38.9 Hz, 1H), 8.11 (d, J=7.0 Hz, 1H), 7.95-7.84 (m, 3H), 7.59-7.51 (m, 2H), 7.48 (s, 1H), 7.33 (m, 2H), 6.66 (d, J=42.4 Hz, 1H), 4.13 (s, 1H), 3.94 (s, 3H), 3.90 (s, 3H), 3.35 (s, 1H), 3.15 (m, 1H), 3.01-2.57 (m, 2H), 1.96 (m, 1H), 1.61-1.40 (m, 2H), 1.28 (m, 2H), 0.95-0.76 (m, 3H), 0.60 (m, 1H), 0.32 (m, 1H).; LRMS (ESI) calcd for $C_{32}H_{32}N_6O_3$ [M+H]+: 549, Found 549.

Compound 34b ((R)-cyclopropyl(3-(4-(2-(3,4-dichlorophenyl)-5,6-dimethoxy-1H-benzo[d]imidazole-1-yl)pyrimidin-2-ylamino)piperidine-1-yl)methanone)

as a yellow solid (52%); $^1$H NMR (400 MHz, MeOD) δ 8.51-8.39 (m, 1H), 7.78 (s, 1H), 7.61 (dd, J=8.2, 5.4 Hz, 1H), 7.39 (dd, J=14.6, 8.2 Hz, 1H), 7.32 (d, J=8.7 Hz, 2H), 6.60 (m, 1H), 4.28 (d, J=13.4 Hz, 1H), 4.19-4.04 (s, 1H), 3.93 (d, J=14.9 Hz, 6H), 2.89 (s, 1H), 1.83 (m, 2H), 1.62 (m, 3H), 1.41-1.25 (m, 2H), 0.93-0.75 (m, 3H), 0.67 (m, 1H), 0.34 (m, 1H).; LRMS (ESI) calcd for $C_{28}H_{28}Cl_2N_6O_3$ [M+H]+: 568, Found 568.

Compound 34c ((R)-cyclopropyl(3-(4-(2-(4-fluoro-3-(trifluoromethyl)phenyl)-5,6-dimethoxy-1H-benzo[d]imidazole-1-yl)pyrimidin-2-ylamino)piperidine-1-yl)methanone)

as a yellow solid (38%); $^1$H NMR (400 MHz, MeOD) δ 8.50-8.39 (m, 1H), 7.92 (s, 1H), 7.78 (s, 1H), 7.43 (m, 1H), 7.30 (s, 2H), 6.60 (s, 1H), 4.28 (m, 1H), 4.14 (s, 1H), 3.93 (s, 3H), 3.89 (s, 3H), 2.95-2.74 (m, 1H), 2.06-1.92 (m, 1H), 1.75 (m, 2H), 1.68-1.46 (m, 2H), 1.28 (m, 2H), 0.89 (m, 3H), 0.62 (m, 1H), 0.44-0.10 (m, 1H).; LRMS (ESI) calcd for $C_{29}H_{28}F_4N_6O_3$ [M+H]+: 585, Found 585.

Compound 34d ((R)-cyclopropyl(3-(4-(2-(2,3-dihydrobenzo[b][1,4]dioxin-6-yl)-5,6-dimethoxy-1H-benzo[d]imidazole-1-yl)pyrimidin-2-ylamino)piperidine-1-yl)methanone)

as a yellow solid (38%); $^1$H NMR (400 MHz, MeOD) δ 8.32 (s, 1H), 7.23 (s, 2H), 7.00 (s, 1H), 6.93 (d, J=8.6 Hz, 1H), 6.86 (d, J=8.6 Hz, 1H), 6.51 (s, 1H), 4.29-4.24 (m, 4H), 3.90 (s, 3H), 3.85 (s, 3H), 3.54 (s, 1H), 3.16-2.90 (m, 1H), 1.90-1.74 (m, 2H), 1.72-1.37 (m, 4H), 1.27 (m, 1H), 0.93-0.75 (m, 3H), 0.63 (s, 1H), 0.43-0.07 (m, 1H).; LRMS (ESI) calcd for $C_{30}H_{32}N_6O_5$ [M+H]+: 557, Found 557.

Compound 34e ((R)-(3-(4-(2-(benzofuran-5-yl)-5,6-dimethoxy-1H-benzo[d]imidazole-1-yl)pyrimidin-2-ylamino)piperidine-1-yl)(cyclopropyl)methanone)

as a yellow solid (38%); $^1$H NMR (400 MHz, MeOD) δ 8.30 (s, 1H), 7.94-7.77 (m, 2H), 7.57 (d, J=8.6 Hz, 1H), 7.42 (m, 2H), 7.29 (s, 1H), 6.91 (s, 1H), 6.56 (s, 1H), 4.10-3.97 (s, 1H), 3.93 (s, 3H), 3.89 (s, 3H), 3.68-3.56 (m, 1H), 2.93 (m, 1H), 1.88-1.73 (m, 2H), 1.63-1.51 (m, 2H), 1.29 (m, 2H), 0.92-0.83 (m, 5H).; LRMS (ESI) calcd for $C_{30}H_{30}N_6O_4$ [M+H]+: 539, Found 539.

<Example 3-1> (R)-cyclopropyl(3-(4-(5,6-dihydroxy-2-(naphthalene-2-yl)-1H-benzo[d]imidazole-1-yl)pyrimidin-2-ylamino)piperidine-1-yl)methanone (35a)

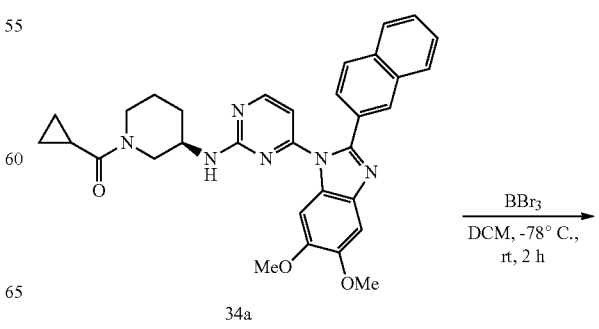

34a

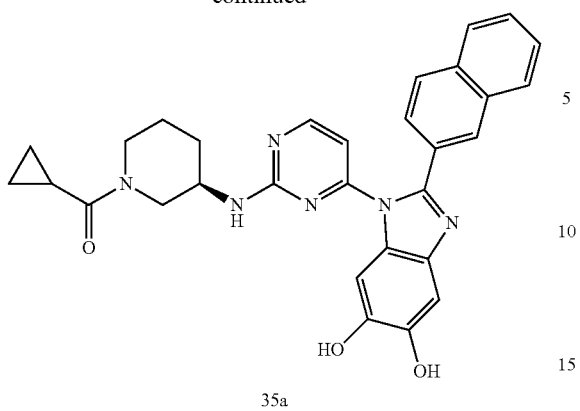

35a

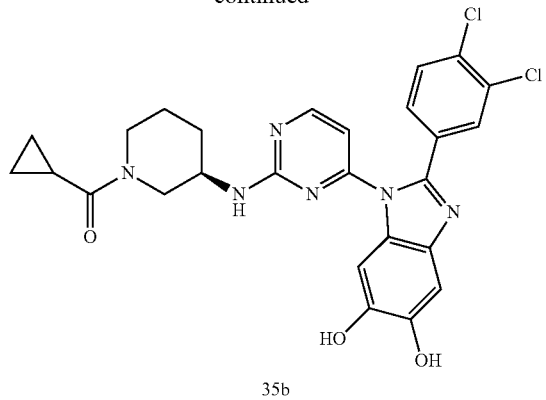

35b

Compound 34a (0.053 mmol) was dissolved in methylene chloride (0.53 ml), BBr$_3$ (25 μl) was added at −78° C., stirred for about 1 hour, and again at room temperature for about 2 hours Was stirred. The mixture was quenched with methanol (0.2 ml) at 0° C. and again stirred at rt for 1 h. The mixture was diluted and extracted with methylene chloride (5 ml), washed three times with saturated aqueous NaHCO$_3$ solution (3 ml), twice with 5 ml of water and twice with saturated sodium chloride solution (5 ml). The organic phase was dried over sodium sulfate and concentrated in vacuo to obtain the product as a white solid. The crude product was purified by flash column chromatography on silica gel using a mobile phase of CH$_2$Cl$_2$:MeOH (40: 1-5:1) to obtain Compound 35a.

as a yellow solid (62%); $^1$H NMR (400 MHz, DMSO) δ 8.24 (s, 1H), 8.12 (s, 1H), 7.93 (m, 3H), 7.61-7.52 (m, 3H), 7.49 (s, 1H), 7.09 (s, 1H), 6.26 (d, J=4.7 Hz, 1H), 3.83 (s, 1H), 3.41 (m, 2H), 3.17 (m, 2H), 2.94 (m, 2H), 1.99 (s, 1H), 1.43 (m, 4H), 0.89-0.66 (m, 4H), 0.57 (m, 1H); LRMS (ESI) calcd for C$_{30}$H$_{28}$N$_6$O$_3$ [M+H]+: 521, Found 521.

In the same manner as in Example 3-1, the compounds of Examples 3-2 to 3-5 were obtained (Compound 35b, 35c, 35d, 35e).

<Example 3-2> (R)-cyclopropyl(3-(4-(2-(3,4-di-chlorophenyl)-5,6-dihydroxy-1H-benzo[d]imidazole-1-yl)pyrimidin-2-ylamino)piperidin-1-yl)methanone (35b)

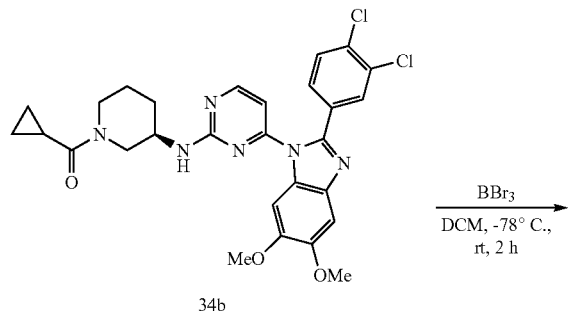

34b as a yellow solid (58%); $^1$H NMR (400 MHz, DMSO) δ 9.16 (s, 1H), 8.44 (d, J=44.8 Hz, 1H), 7.74 (s, 2H), 7.30 (d, J=39.1 Hz, 1H), 7.08 (s, 1H), 6.57 (m, 1H), 4.26 (s, 1H), 3.91 (s, 1H), 2.99 (s, 1H), 2.84-2.53 (m, 1H), 2.08-1.86 (m, 1H), 1.66 (m, 2H), 1.51 (m, 2H), 1.23 (m, 3H), 0.88-0.65 (m, 3H), 0.57 (m, 1H), 0.25 (m, 1H).; LRMS (ESI) calcd for C$_{26}$H$_{24}$C$_{12}$N$_6$O$_3$ [M+H]+: 540, Found 540.

<Example 3-3> (R)-cyclopropyl(3-(4-(2-(4-fluoro-3-(trifluoromethyl)phenyl)-5,6-dihydroxy-1H-benzo[d]imidazole-1-yl)pyrimidin-2-ylamino)piperidin-1-yl)methanone (35c)

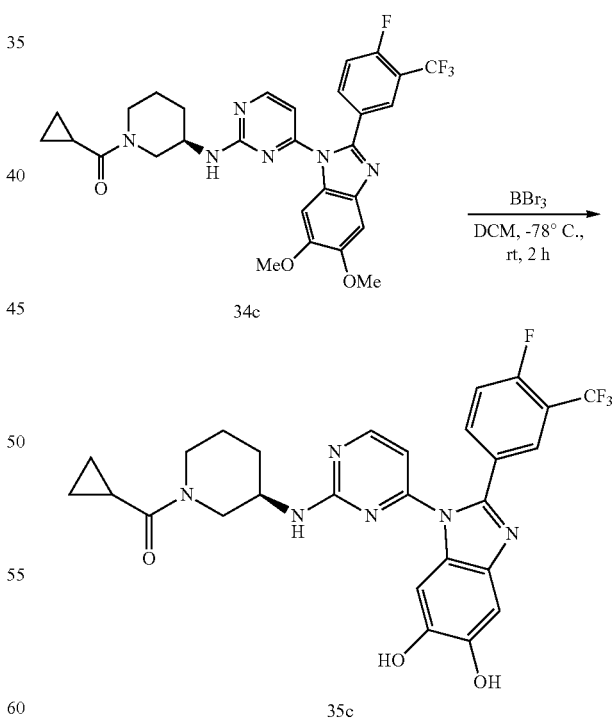

as a yellow solid (60%); $^1$H NMR (400 MHz, MeOD) δ 8.36 (d, J=68.0 Hz, 1H), 7.88 (d, J=4.4 Hz, 1H), 7.75 (s, 1H), 7.48-7.37 (m, 1H), 7.13 (d, J=6.5 Hz, 1H), 6.88 (d, J=147.6 Hz, 1H), 6.34 (s, 1H), 4.60 (s, 1H), 4.31-3.82 (s, 2H), 3.13 (m, 1H), 2.76 (m, 1H), 2.06-1.70 (m, 3H), 1.60 (m, 2H), 1.29

(m, 2H), 1.01-0.54 (m, 4H), 0.32 (m, 1H).; LRMS (ESI) calcd for C$_{27}$H$_{24}$F$_4$N$_6$O$_3$[M+H]+: 557, Found 557.

<Example 3-4> (R)-cyclopropyl(3-(4-(2-(2,3-dihydrobenzo[b][1,4]dioxin-6-yl)-5,6-dihydroxy-1H-benzo[d]imidazole-1-yl)pyrimidin-2-ylamino)piperidine-1-yl)methanone (35d)

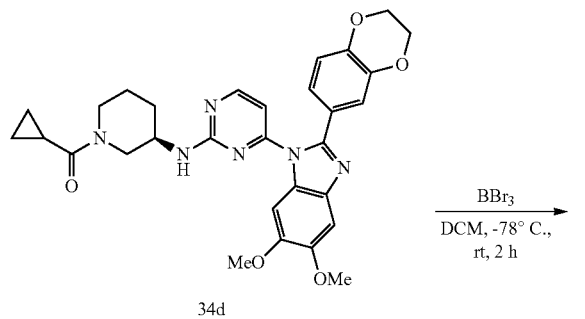

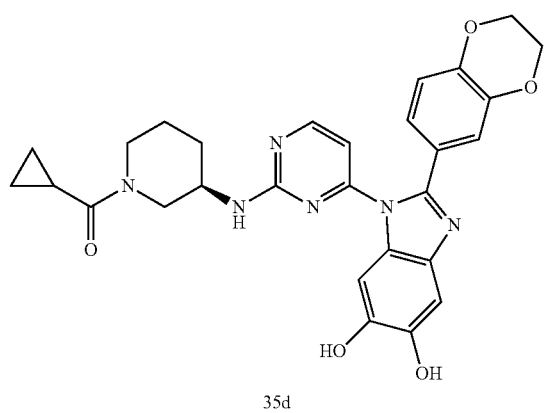

as a yellow solid (42%); $^1$H NMR (400 MHz, MeOD) δ 8.30 (s, 1H), 7.51 (s, 1H), 7.12 (d, J=5.9 Hz, 1H), 7.02 (s, 1H), 6.95 (d, J=2.9 Hz, 1H), 6.93-6.85 (m, 1H), 6.20 (d, J=5.0 Hz, 1H), 4.69 (s, 1H), 4.29 (m, 4H), 3.93 (s, 1H), 3.57 (s, 1H), 3.22 (m, 1H), 2.87 (m, 1H), 1.96 (m, 3H), 1.61 (m, 3H), 1.31 (m, 1H), 1.06-0.62 (m, 4H), 0.34 (m, 1H).; LRMS (ESI) calcd for C$_{28}$H$_{28}$N$_6$O$_5$ [M+H]+: 529, Found 529.

<Example 3-5> (R)-(3-(4-(2-(benzofuran-5-yl)-5,6-dihydroxy-1H-benzo[d]imidazole-1-yl)pyrimidin-2-ylamino)piperidine-1-yl)(cyclopropyl)methanone (35e)

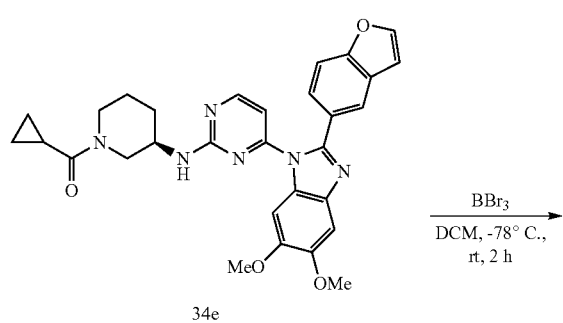

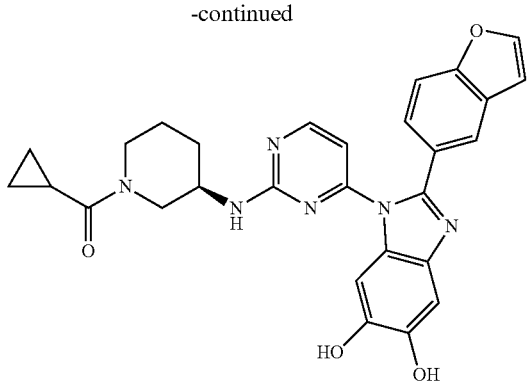

as a white solid (42%); $^1$H NMR (400 MHz, MeOD) δ 8.36-8.07 (m, 1H), 7.84 (d, J=1.9 Hz, 1H), 7.80 (s, 1H), 7.56 (m, 2H), 7.41 (d, J=7.7 Hz, 1H), 7.13 (d, J=7.1 Hz, 1H), 6.90 (d, J=4.7 Hz, 1H), 6.11 (m, 1H), 4.22 (s, 1H), 3.96 (s, 1H), 3.23 (s, 1H), 2.92 (m, 1H), 2.06-1.72 (m, 3H), 1.59 (m, 3H), 1.15 (m, 2H), 0.86 (m, 3H), 0.67-0.20 (m, 2H).; LRMS (ESI) calcd for C$_{28}$H$_{26}$N$_6$O$_4$ [M+H]+: 511, Found 511.

Experimental Example 1. Measurement of JNK3 Enzymatic Activity

Changes in JNK3 enzymatic activity due to treatment with benzimidazole derivatives (Formula 1) according to the present invention were confirmed through IC$_{50}$.

First, a substrate was added to a prepared base reaction buffer solution (20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO), a human JNK3 enzyme was added into the prepared substrate solution, and the resulting solution was mixed. ATP (10 μM) and ATF2 (3 μM) were used as substrates, and among them, ATP was used as a common substrate. Next, the compound according to the present invention dissolved in 100% DMSO was added to an enzyme reaction solution, and incubated at room temperature for 20 minutes. Subsequently, $^{33}$P-ATP was added to the mixed reaction solution to initiate the reaction, followed by incubation at room temperature for 2 hours, and enzymatic activity was detected by a filter-binding method. Specifically, 25 al per resulting solution was slowly spotted on P81 paper and placed in a scintillation vial, and then the paper was washed four times with 0.75% phosphoric acid for 10 minutes each and washed once with acetone for 5 minutes. 5 ml of a scintillation cocktail was added to the scintillation vial and signals were read using a scintillation counter.

As a result, IC$_{50}$ values of the benzimidazole derivatives according to the present invention for JNK3 enzymatic activity are shown in Tables 1 to 3 below, from which it was confirmed that the benzimidazole derivatives according to the present invention exhibited excellent JNK3 inhibitory activity. In particular, it was confirmed that, the benzimidazole derivatives of Formula 1 wherein 1,3-benzodioxolyl, 2,3-dihydro-1,4-benzodioxinyl, quinolinyl, or benzofuranyl was introduced into R$_1$, cyclopropyl methanone piperidinyl was introduced into R$_4$, and a hydroxy group was introduced into both R$_2$ and R$_3$ exhibited further enhanced JNK3 inhibitory activity.

TABLE 1
| No | R₁ | R₂ | R₃ | R₄ | JNK3 (IC$_{50}$, nM) |
|---|---|---|---|---|---|
| 9a | 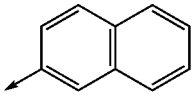 | H | OH | 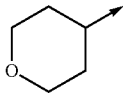 | + |
| 10a | | H | OH | 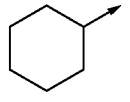 | + |
| 13a | | H | OH | 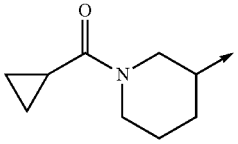 | ++ |
| 9b | 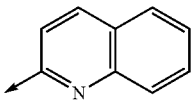 | H | OH | 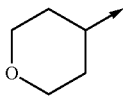 | − |
| 13b | | H | OH | 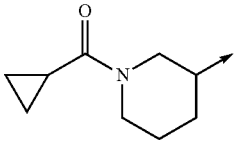 | ++ |
| 9c | 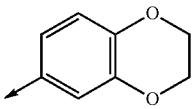 | H | OH | 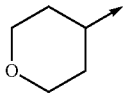 | + |
| 10c | | H | OH | 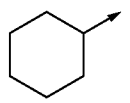 | + |
| 13c | | H | OH | 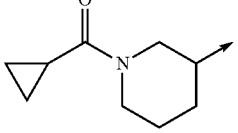 | ++ |
| 9d | 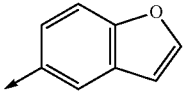 | H | OH | 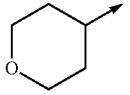 | + |
| 10d | | H | OH | 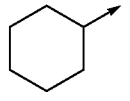 | + |
| 13d | | H | OH | 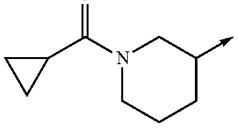 | +++ |
| 9e | 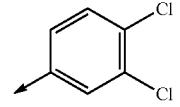 | H | OH | 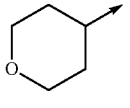 | ++ |

TABLE 1-continued

| No | R₁ | R₂ | R₃ | R₄ | JNK3 (IC$_{50}$, nM) |
|---|---|---|---|---|---|
| 10e | | H | OH | cyclohexyl | + |
| 13e | | H | OH | cyclopropyl-C(O)-N-piperidinyl | +++ |
| 9f | 4-fluoro-3-(trifluoromethyl)phenyl | H | OH | tetrahydropyran-4-yl | ++ |
| 10f | | H | OH | cyclohexyl | + |
| 13f | | H | OH | cyclopropyl-C(O)-N-piperidinyl | ++ |
| 13g | benzo[d][1,3]dioxol-5-yl | H | OH | tetrahydropyran-4-yl | ++ |
| | SP600125 | | | | ++ |

+: IC$_{50}$ > 100 nM
++: IC$_{50}$ = 30~100 nM
+++: IC$_{50}$ < 30 nM

TABLE 2

| No | R₁ | R₂ | R₃ | R₄ | JNK3 (IC$_{50}$, nM) |
|---|---|---|---|---|---|
| 22a | naphthalen-2-yl | OH | H | tetrahydropyran-4-yl | ++ |
| 23a | | OH | H | cyclohexyl | + |
| 26a | | OH | H | cyclopropyl-C(O)-N-piperidinyl | ++ |
| 22b | quinolin-2-yl | OH | H | tetrahydropyran-4-yl | ++ |
| 23b | | OH | H | cyclohexyl | + |

TABLE 2-continued
| No | R₁ | R₂ | R₃ | R₄ | JNK3 (IC₅₀, nM) |
|---|---|---|---|---|---|
| 26b | | OH | H | 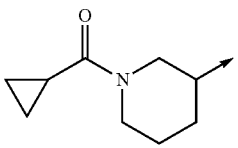 | ++ |
| 22c | 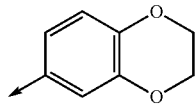 | OH | H | 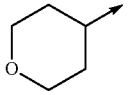 | ++ |
| 23c | | OH | H | 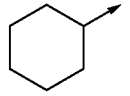 | + |
| 26c | | OH | H | 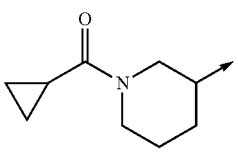 | ++ |
| 22d | 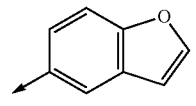 | OH | H | 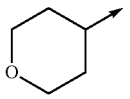 | ++ |
| 23d | | OH | H | 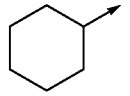 | + |
| 26d | | OH | H | 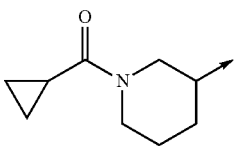 | +++ |
| 23e | 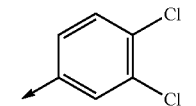 | OH | H | 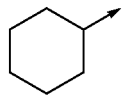 | ++ |
| 26e | | OH | H | 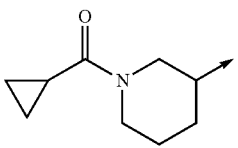 | +++ |
| 23f | 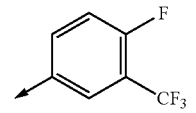 | OH | H | 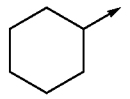 | + |
| 26f | | OH | H | 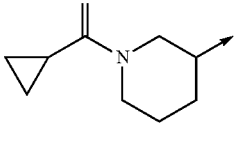 | ++ |
| | SP600125 | | | | ++ |
+: IC₅₀ > 100 nM
++: IC₅₀ = 30~100 nM
+++: IC₅₀ < 30 nM

TABLE 3

| No | R₁ | R₂ | R₃ | R₄ | JNK3 (IC$_{50}$, nM) |
|---|---|---|---|---|---|
| 35a | 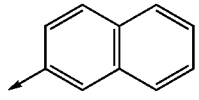 | OH | OH | 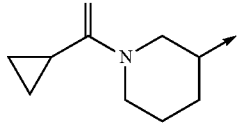 | +++ |
| 35b | 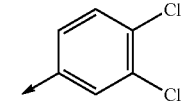 | OH | OH | 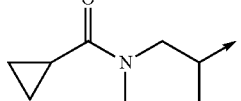 | +++ |
| 35c | 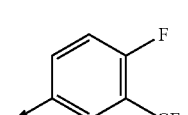 | OH | OH | 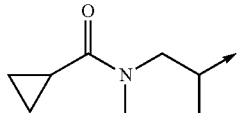 | +++ |
| 35d | 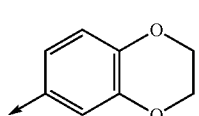 | OH | OH | 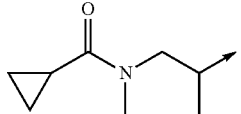 | +++ |
| 35e | 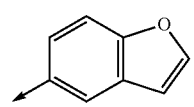 | OH | OH | 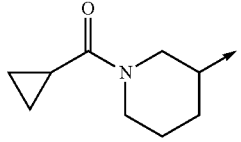 | +++ |
| SP600125 | | | | | ++ |

+: IC$_{50}$ > 100 nM
++: IC$_{50}$ = 30~100 nM
+++: IC$_{50}$ < 30 nM

Experimental Example 2. Confirmation of Effect of Reducing Concentration of Beta-Amyloid Oligomer in Brain Tissue Using Animal Model JNK3 is known to phosphorylate and activate amyloid precursor protein (APP), which is the main cause of Alzheimer's disease, to thus allow the APP to be located in a cell membrane, and promotes the conversion of APP to beta-amyloid, and it has been reported that, even in a case in which, after beta-amyloid is formed, the apoptosis of neurons is induced by toxicity thereof, the activation of JNK3 acts as a main cause. Based on these facts, in the present experimental example, the derivative of the present invention (compound 35d) was administered via intravenous injection (IV) to Alzheimer's disease transgenic mice in a dose of 15 mg/kg/day three times per 1 week for a total of 2 weeks, and then changes in the concentration of APP and beta-amyloid oligomer in the frontal lobe cortex were confirmed through western blotting. Meanwhile, normal mice (WT(veh)) were used as a control, and non-treated Alzheimer's disease transgenic mice (2×TG(veh)) were used as a comparative group.

As a result, as illustrated in FIG. 1, it was confirmed that, when treated with the derivative according to the present invention, the expression level of APP and the concentration of beta-amyloid oligomer were significantly reduced compared to the comparative group. Taken together, the results of Experimental Example 1 indicate that the derivatives according to the present invention having excellent JNK3 inhibitory activity inhibit the formation of beta-amyloid, and thus are able to be effectively used for the treatment of neurodegenerative brain diseases such as Alzheimer' disease.

Experimental Example 3. Evaluation of Migration of Blood-Brain Barrier

Figure 2:
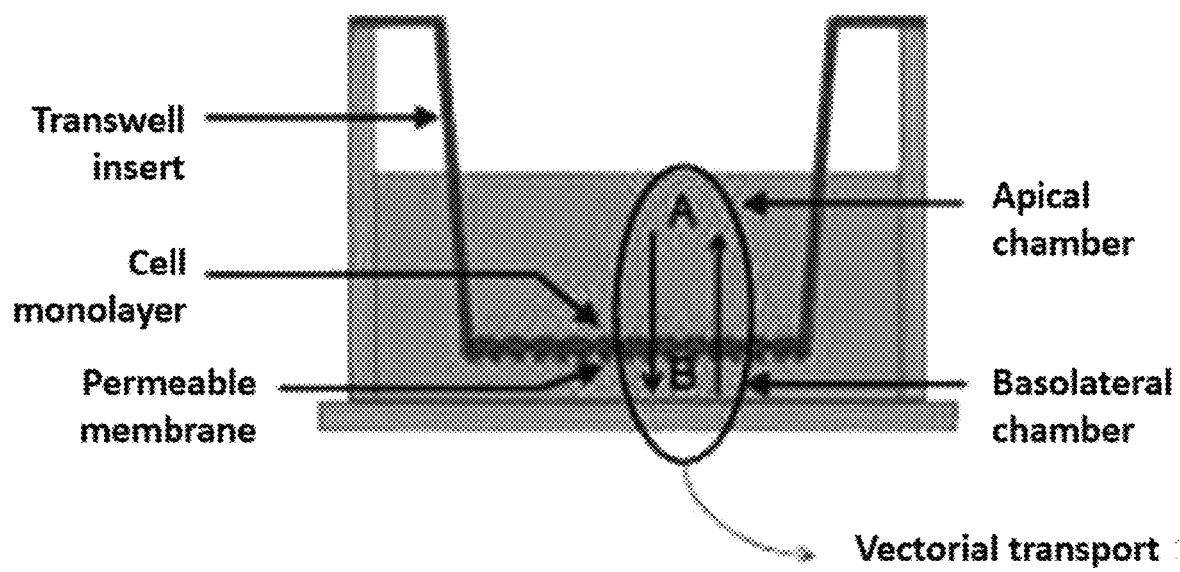
FIG. 2 is a schematic view illustrating a migration evaluation system of the blood-brain barrier (BBB).

The blood-brain barrier (BBB) functions as a primary barrier to prevent the invasion of foreign substances, but acts as an obstacle to treatment in pathological circumstances. That is, therapeutics for the treatment of brain diseases or maintaining the condition thereof are very unlikely to permeate the blood-brain barrier, and thus are unable to be effectively used, and accordingly, the selection of drugs for the treatment of brain diseases is limited. Therefore, in the present experimental example, the possibility of an actual use of the derivatives according to the present invention (Compounds 26c and 35d) as drugs for the treatment of brain diseases was examined by confirming whether the derivatives were able to effectively permeate the blood-brain barrier. First, P-gp(MDR1)-overexpressing Caco-2-MDR1 cells were plated on a BBB migration evaluation system constructed as illustrated in FIG. 2, and then the derivative according to the present invention and the like were added thereto, followed by incubation for a certain period of time. Subsequently, the concentration of derivative present in an apical chamber (A) and a basolateral chamber (B) was measured and a permeability coefficient ($P_{app}$) was calculated by Equation 1 below. Meanwhile, caffeine and atenolol were used as comparative materials.

$$P_{aap} = dQ/dt/C_0 A \quad \text{[Equation 1]}$$

(dQ/dt: the amount of material permeating into mebrain, A: area, and $C_0$: initial concentration of material)

As a result, as shown in Table 4 below, the derivative according to the present invention exhibited higher permeability than that of other drugs, as an effect due to heterosubstituents introduced into the $R_1$ group, and thus may be anticipated to be highly effective in being used as a therapeutic material for neurological brain diseases.

TABLE 4

| Test | A to B | B to A | Efflux Ratio | Permeability |
|---|---|---|---|---|
| Caffein | 5.15 | 6.161 | 1.20 | High |
| Atenolol | 0.023 | 0.040 | 1.71 | Limited |
| Compound 26c | 1.919 | 1.985 | 1.03 | High |
| Compound 35d | 1.728 | 1.956 | 1.13 | High |

The preferred embodiments of the present invention are provided to aid in understanding the present invention. However, the examples are merely provided to more easily understand the present invention, and the contents of the present invention are not limited by the examples.

The invention claimed is:

1. A benzimidazole derivative of Formula 1 or a pharmaceutically acceptable salt thereof:

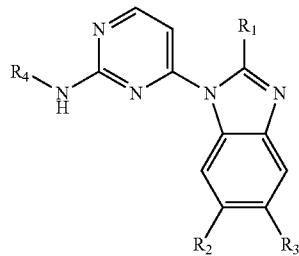

[Formula 1]

wherein, in Formula 1, $R_1$ is selected from the group consisting of benzooxazolyl, benzodioxazolyl, 1,3-benzodioxolyl, 1,4-benzodioxinyl, dihydrobenzodioxinyl, benzothiazolyl, benzothiophenyl, quinolinyl, isoquinolinyl, indolyl, benzofuranyl, purinyl, and indolizinyl;

$R_2$ and $R_3$ are each independently hydrogen or hydroxy;

$R_4$ represents a $C_3$-$C_{10}$ cycloalkyl or a $C_4$-$C_{10}$ heterocycloalkyl wherein the $C_4$-$C_{10}$ heterocycloalkyl is selected from the group consisting of tetrahydrofuranyl, tetrahydrothiophenyl, pyrrolidinyl, tetrahydropyranyl, tetrahydrothiopyranyl, and piperidinyl; and $R_4$ may be substituted or unsubstituted with a $C_4$-$C_{10}$ cycloalkylcarbonyl.

2. The benzimidazole derivative of Formula 1 or a pharmaceutically acceptable salt thereof, of claim 1, wherein, $R_1$ represents 1,3-benzodioxolyl, 2,3-dihydro-1,4-benzodioxinyl, quinolinyl, or benzofuranyl;

$R_2$ and $R_3$ are each independently hydrogen or hydroxyl;

$R_4$ is cyclohexyl, tetrahydropyranyl, or piperidinyl; and $R_4$ may be substituted or unsubstituted with a $C_4$-$C_{10}$ cycloalkylcarbonyl.

3. The benzimidazole derivative of Formula 1 or a pharmaceutically acceptable salt thereof, of claim 1, $R_1$ represents 1,3-benzodioxolyl, 2,3-dihydro-1,4-benzodioxinyl, quinolinyl, or benzofuranyl;

wherein, $R_2$ and $R_3$ are each independently hydrogen or hydroxyl; and $R_4$ is cyclohexyl, tetrahydropyranyl, or cyclopropyl methanone piperidinyl.

4. The benzimidazole derivative of Formula 1 or a pharmaceutically acceptable salt thereof, of claim 1, wherein the benzimidazole derivative of Formula 1 is selected from the group consisting of the following:

2-(quinoline-2-yl)-1-(2-((tetrahydro-2H-pyran-4-yl)amino)pyrimidin-4-yl)-1H-benzo[d]imidazole-5-ol;

2-(2,3-dihydrobenzo[b][1,4]dioxin-6-yl)-1-(2-((tetrahydro-2H-pyran-4-yl)amino)pyrimidin-4-yl)-1H-benzo[d]imidazole-5-ol;

2-(benzofuran-5-yl)-1-(2-((tetrahydro-2H-pyran-4-yl)amino)pyrimidin-4-yl)-1H-benzo[d]imidazole-5-ol;

1-(2-(cyclohexylamino)pyrimidin-4-yl)-2-(2,3-dihydrobenzo[b][1,4]dioxin-6-yl)-1H-benzo[d]imidazole-5-ol;

2-(benzofuran-5-yl)-1-(2-(cyclohexylamino)pyrimidin-4-yl)-1H-benzo[d]imidazole-5-ol;

(S)-cyclopropyl(3-((4-(5-hydroxy-2-(quinoline-2-yl)-1H-benzo[d]imidazole-1-yl)pyrimidin-2-yl)amino)piperidine-1-yl)methanone;

(S)-cyclopropyl(3-((4-(2-(2,3-dihydrobenzo[b][1,4]dioxin-6-yl)-5-hydroxy-1H-benzo[d]imidazole-1-yl)pyrimidin-2-yl)amino)piperidine-1-yl)methanone;

(S)-(3-(4-(2-(benzofuran-5-yl)-5-hydroxy-1H-benz[d]imidazole-1-yl)pyrimidin-2-ylamino)piperidine-1-yl)(cyclopropyl)methanone;

(S)-(3-(4-(2-(benzo[d][1,3]dioxol-5-yl)-5-hydroxy-1H-benz[d]imidazole-1-yl)pyrimidin-2-ylamino)piperidine-1-yl)(cyclopropyl)methanone;

2-(quinoline-2-yl)-1-(2-((tetrahydro-2H-pyran-4-yl)amino)pyrimidin-4-yl)-1H-benzo[d]imidazole-6-ol;

2-(2,3-dihydrobenzo[b][1,4]dioxin-6-yl)-1-(2-((tetrahydro-2H-pyran-4-ylamino)pyrimidin-4-yl)-1H-benzo[d]imidazole-6-ol; 2-(benzofuran-5-yl)-1-(2-((tetrahydro-2H-pyran-4-yl)amino)pyrimidin-4-yl)-1H-benzo[d]imidazole-6-ol;

3-(2-(cyclohexylamino)pyrimidin-4-yl)-2-(quinoline-2-yl)-3H-benz[d]imidazole-5-ol;

1-(2-(cyclohexylamino)pyrimidin-4-yl)-2-(2,3-dihydrobenzo[b][1,4]dioxin-6-yl)-1H-benzo[d]imidazole-6-ol;

2-(benzofuran-5-yl)-1-(2-(cyclohexyl amino)pyrimidin-4-yl)-1H-benzo[d]imidazole-6-ol;

(S)-cyclopropyl(3-(4-(6-hydroxy-2-(quinoline-2-yl)-1H-benzo[d]imidazole-1-yl)pyrimidin-2-ylamino)piperidine-1-yl)methanone;

(S)-cyclopropyl(3-((4-(2-(2,3-dihydrobenzo[b][1,4]dioxin-6-yl)-6-hydroxy-1H-benzo[d]imidazole-1-yl)pyrimidin-2-yl)amino)piperidine-1-yl)methanone;

(S)-(3-((4-(2-(benzofuran-5-yl)-6-hydroxy-1H-benzo[d]imidazole-1-yl)pyrimidin-2-yl)amino)piperidine-1-yl)(cyclopropyl)methanone;

(R)-cyclopropyl(3-(4-(2-(2,3-dihydrobenzo[b][1,4]dioxin-6-yl)-5,6-dihydroxy-1H-benzo[d]imidazole-1-yl)pyrimidin-2-ylamino)piperidine-1-yl)methanone; and (R)-(3-(4-(2-(benzofuran-5-yl)-5,6-dihydroxy-1H-benzo[d]imidazole-1-yl)pyrimidin-2-ylamino)piperidine-1-yl)(cyclopropyl)methanone.

5. A method of treating a degenerative neurological disease selected from the group consisting of Alzheimer's disease, Parkinson's disease, Huntington's disease, multiple sclerosis and stroke, comprising administering to a subject a therapeutically effective amount of a benzimidazole derivative or a pharmaceutically acceptable salt thereof, according to claim 1.

* * * * *